(12) United States Patent
Adams et al.

(10) Patent No.: US 9,475,806 B2
(45) Date of Patent: Oct. 25, 2016

(54) COMPLEMENT FACTOR B INHIBITORS AND USES THERE OF

(71) Applicants: Christopher Michael Adams, Somerville, MA (US); Charles Babu, Arlington, TX (US); Michael Paul Capparelli, Cambridge, MA (US); Jian Ding, Bedford, MA (US); Takeru Ehara, Arlington, MA (US); Keith Jendza, Boston, MA (US); Nan Ji, Arlington, MA (US); Rajeshri Ganesh Karki, Somerville, MA (US); Toshio Kawanami, Boston, MA (US); Liang Xue, Arlington, TX (US); Nello Mainolfi, Boston, MA (US); James J. Powers, Waltham, MA (US); Michael H. Serrano-Wu, Belmont, MA (US); Chun Zhang, Waltham, MA (US)

(72) Inventors: Christopher Michael Adams, Somerville, MA (US); Charles Babu, Arlington, TX (US); Michael Paul Capparelli, Cambridge, MA (US); Jian Ding, Bedford, MA (US); Takeru Ehara, Arlington, MA (US); Keith Jendza, Boston, MA (US); Nan Ji, Arlington, MA (US); Rajeshri Ganesh Karki, Somerville, MA (US); Toshio Kawanami, Boston, MA (US); Liang Xue, Arlington, TX (US); Nello Mainolfi, Boston, MA (US); James J. Powers, Waltham, MA (US); Michael H. Serrano-Wu, Belmont, MA (US); Chun Zhang, Waltham, MA (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 14/774,430

(22) PCT Filed: Mar. 13, 2014

(86) PCT No.: PCT/US2014/026875
§ 371 (c)(1),
(2) Date: Sep. 10, 2015

(87) PCT Pub. No.: WO2014/143638
PCT Pub. Date: Sep. 18, 2014

(65) Prior Publication Data
US 2016/0024079 A1 Jan. 28, 2016

Related U.S. Application Data

(60) Provisional application No. 61/782,750, filed on Mar. 14, 2013.

(51) Int. Cl.
*C07D 401/14* (2006.01)
*A61K 31/4353* (2006.01)
*A61K 31/437* (2006.01)
*C07D 471/04* (2006.01)

(52) U.S. Cl.
CPC .................... *C07D 471/04* (2013.01)

(58) Field of Classification Search
CPC  C07D 401/02; C07D 401/10; C07D 401/14; A61K 31/437; A61K 31/4353
USPC .......................... 546/119, 121; 514/300, 303
See application file for complete search history.

(56) References Cited

U.S. PATENT DOCUMENTS

| 4,859,684 A | 8/1989 | Raeymaekers et al. |
| 5,342,957 A | 8/1994 | Van Wauwe et al. |

(Continued)

FOREIGN PATENT DOCUMENTS

| CN | 1285557 | 11/2006 |
| EP | 0426225 | 5/1991 |

(Continued)

OTHER PUBLICATIONS

Barnes et al., European Respiratory journal, 25(6):1084-1106 (2005).

(Continued)

*Primary Examiner* — Niloofar Rahmani
(74) *Attorney, Agent, or Firm* — John B. Alexander

(57) ABSTRACT

The present invention provides a compound of formula (I): wherein X is N or CH, Y is NH, O or S, methods for manufacturing these compounds, and their uses as Factor B inhibitors for the treatment of conditions and diseases associated with complement alternative pathway activation such as age-related macular degeneration, diabetic retinopathy and related ophthalmic diseases. The present invention further provides pharmaceutical compositions and combinations of pharmacologically active agents.

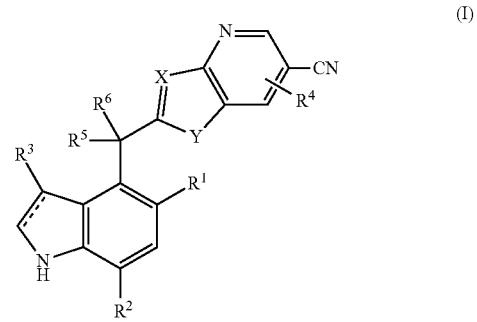

14 Claims, No Drawings

(56) References Cited

U.S. PATENT DOCUMENTS

| | | |
|---|---|---|
| 5,409,929 A | 4/1995 | Ciganek |
| 5,763,688 A | 6/1998 | Ikariya et al. |
| 8,012,682 B2 | 9/2011 | Lukyanov et al. |
| 2007/0259936 A1 | 11/2007 | Player et al. |
| 2008/0146501 A1 | 6/2008 | Hageman et al. |
| 2008/0255000 A1 | 10/2008 | Dogulu et al. |
| 2008/0280825 A1 | 11/2008 | Hageman et al. |
| 2009/0111708 A1 | 4/2009 | Seddon et al. |
| 2009/0214538 A1 | 8/2009 | Fung et al. |
| 2009/0221665 A1 | 9/2009 | Earnest |
| 2010/0069468 A1 | 3/2010 | Hess et al. |
| 2010/0120665 A1 | 5/2010 | Kaleko et al. |
| 2010/0166862 A1 | 7/2010 | Francois et al. |
| 2010/0273720 A1 | 10/2010 | Hageman et al. |
| 2011/0114888 A1 | 5/2011 | Akino |
| 2011/0117557 A1 | 5/2011 | Canter et al. |
| 2011/0229439 A1 | 9/2011 | Humphnes et al. |
| 2012/0071356 A1 | 3/2012 | Allikmets et al. |

FOREIGN PATENT DOCUMENTS

| | | |
|---|---|---|
| JP | 2010037511 | 4/2010 |
| WO | 95/04052 | 2/1995 |
| WO | 97/07097 | 2/1997 |
| WO | 99/40072 | 8/1999 |
| WO | 2004/069256 | 8/2004 |
| WO | 2006/041872 | 4/2006 |
| WO | 2006/084338 | 8/2006 |
| WO | 2006/099379 | 9/2006 |
| WO | 2006/125324 | 11/2006 |
| WO | 2007/056111 | 5/2007 |
| WO | 2007/095185 | 8/2007 |
| WO | 2007095287 | 8/2007 |
| WO | 2008/003703 | 1/2008 |
| WO | 2008/106644 | 9/2008 |
| WO | 2008/140793 | 11/2008 |
| WO | 2009/105757 | 8/2009 |
| WO | 2009/157429 | 12/2009 |
| WO | 2010/029162 | 3/2010 |
| WO | 2010/066684 | 6/2010 |
| WO | 2010/085542 | 7/2010 |
| WO | 2010/127152 | 11/2010 |
| WO | 2011/0017229 | 2/2011 |
| WO | 2009/073564 | 6/2011 |
| WO | 2013/016197 | 1/2013 |
| WO | 2013/164802 | 11/2013 |

OTHER PUBLICATIONS

Doan et al., The Journal of Clinical Pharmacology, 45:751-762 (2005).
Qian et al., Journal of Neural Transmission, 117(8):971-979 (2010).
Guttman et al., Canadian medical Association Journal, 168(3):293-301 (2003).
Knaryan et al., Journal of Neurochemistry, 118:326-338 (2011).
Le et al., The Journal of Biological Chemistry, 282(48):34809-34816 (2007).
Ruiz-Gomez et al., J. Med. Chem., 52:6042-6052 (2009).

COMPLEMENT FACTOR B INHIBITORS AND USES THERE OF

The application is a U.S. National Phase filing of International Application No. PCT/US2014/026875filed 13 Mar. 2014, which claims priority to U.S. Application No. 61/782,750 filed 14 Mar. 2013, the contents of which are incorporated herein by reference in their entirety.

RELATED APPLICATIONS

This application claims priority to U.S. Provisional Application No. 61/782,750 filed on Mar. 18, 2013, the contents of which are incorporated herein by reference in their entirety.

FIELD OF THE INVENTION

The invention relates to the inhibition of the complement alternative pathway and particularly to inhibition of Factor B, in patients suffering from conditions and diseases associated with complement alternative pathway activation such as age-related macular degeneration, diabetic retinopathy and related ophthalmic diseases.

BACKGROUND OF THE INVENTION

The complement system is a crucial component of the innate immunity system and comprises a group of proteins that are normally present in an inactive state. These proteins are organized in three activation pathways: the classical, the lectin, and the alternative pathways (V. M. Holers, In Clinical Immunology: Principles and Practice, ed. R. R. Rich, Mosby Press; 1996, 363-391). Molecules from microorganisms, antibodies or cellular components can activate these pathways resulting in the formation of protease complexes known as the C3-convertase and the C5-convertase. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The alternative pathway is a magnesium-dependent cascade which is activated by deposition and activation of C3 on certain susceptible surfaces (e.g., cell wall polysaccharides of yeast and bacteria, and certain biopolymer materials).

Factor B may be a suitable target for the inhibition of this amplification of the complement pathways because its plasma concentration in humans is typically about 200 µg/mL (or about 2 µM), and it has been shown to be a critical enzyme for activation of the alternative complement pathway (P. H. Lesavre and H. J. Müller-Eberhard. J. Exp. Med., 1978; 148: 1498-1510; J. E. Volanakis et al., New Eng. J. Med., 1985; 312:395-401).

Macular degeneration is a clinical term that is used to describe a family of diseases that are characterized by a progressive loss of central vision associated with abnormalities of Bruch's membrane, the choroid, the neural retina and/or the retinal pigment epithelium. In the center of the retina is the macula lutea, which is about ⅓ to ½ cm in diameter. The macula provides detailed vision, particularly in the center (the fovea), because the cones are higher in density and because of the high ratio of ganglion cells to photoreceptor cells. Blood vessels, ganglion cells, inner nuclear layer and cells, and the plexiform layers are all displaced to the side (rather than resting above the photoreceptor cells), thereby allowing light a more direct path to the cones. Under the retina is the choroid, a part of the uveal tract, and the retinal pigmented epithelium (RPE), which is between the neural retina and the choroid. The choroidal blood vessels provide nutrition to the retina and its visual cells.

Age-related macular degeneration (AMD), the most prevalent form of macular degeneration, is associated with progressive loss of visual acuity in the central portion of the visual field, changes in color vision, and abnormal dark adaptation and sensitivity. Two principal clinical manifestations of AMD have been described as the dry, or atrophic, form and the neovascular, or exudative, form. The dry form is associated with atrophic cell death of the central retina or macula, which is required for fine vision used for activities such as reading, driving or recognizing faces. About 10-20% of these AMD patients progress to the second form of AMD, known as neovascular AMD (also referred to as wet AMD).

Neovascular AMD is characterized by the abnormal growth of blood vessels under the macula and vascular leakage, resulting in displacement of the retina, hemorrhage and scarring. This results in a deterioration of sight over a period of weeks to years. Neovascular AMD cases originate from intermediate or advanced dry AMD. The neovascular form accounts for 85% of legal blindness due to AMD. In neovascular AMD, as the abnormal blood vessels leak fluid and blood, scar tissue is formed that destroys the central retina.

The new blood vessels in neovascular AMD are usually derived from the choroid and are referred to as choroidal neovascularizaton (CNV). The pathogenesis of new choroidal vessels is poorly understood, but such factors as inflammation, ischemia, and local production of angiogenic factors are thought to be important. A published study suggests that CNV is caused by complement activation in a mouse laser model (Bora P. S., J. Immunol. 2005; 174; 491-497).

Human genetic evidence implicates the involvement of the complement system, particularly the alternative pathway, in the pathogenesis of Age-related Macular Degeneration (AMD). Significant associations have been found between AMD and polymorphisms in complement factor H (CFH) (Edwards A O, et al. Complement factor H polymorphism and age-related macular degeneration. Science. 2005 Apr. 15; 308(5720):421-4; Hageman G S, et al A common haplotype in the complement regulatory gene factor H (HF1/CFH) predisposes individuals to age-related macular degeneration. Proc Natl Acad Sci USA. 2005 May 17; 102(20):7227-32; Haines J L, et al. Complement factor H variant increases the risk of age-related macular degeneration. Science. 2005 Apr. 15; 308(5720):419-21; Klein R. J, et al Complement factor H polymorphism in age-related macular degeneration. Science. 2005 Apr. 15; 308(5720): 385-9; Lau L I, et al. Association of the Y402H polymorphism in complement factor H gene and neovascular age-related macular degeneration in Chinese patients. Invest Ophthalmol Vis Sci. 2006 August; 47(8):3242-6; Simonelli F, et al. Polymorphism p.402Y>H in the complement factor H protein is a risk factor for age related macular degeneration in an Italian population. Br J Ophthalmol. 2006 September; 90(9):1142-5; and Zareparsi S, et al Strong association of the Y402H variant in complement factor H at 1q32 with susceptibility to age-related macular degeneration. Am J Hum Genet. 2005 July; 77(1):149-53.), complement factor B (CFB) and complement C2 (Gold B, et al. Variation in factor B (BF) and complement component 2 (C2) genes is associated with age-related macular degeneration. Nat Genet. 2006 April; 38(4):458-62 and Jakobsdottir J, et al. C2 and CFB genes inage-related maculopathy and joint action with CFH and LOC387715 genes. PLoS One. 2008 May 21; 3(5):e2199), and most recently in complement C3 (Despriet D D, et al Complement component C3 and risk of age-related macular degeneration. Ophthalmology. 2009 March; 116(3):474-480.e2; Maller J B, et al Variation in complement factor 3 is associated with risk of age-related macular degeneration. Nat Genet. 2007 October; 39(10):1200-1 and Park K H, et al Complement component 3 (C3) haplotypes and risk of advanced age-related macular degeneration. Invest Ophthalmol Vis Sci. 2009 July; 50(7):3386-93. Epub 2009 Feb. 21.). Taken together, the genetic variations in the alternative pathway components CFH, CFB, and C3 can predict clinical outcome in nearly 80% of cases.

Currently there is no proven medical therapy for dry AMD and many patients with neovascular AMD become legally blind despite current therapy with anti-VEGF agents such as Lucentis. Thus, it would be desirable to provide therapeutic agents for the treatment or prevention of complement mediated diseases and particularly for the treatment of AMD.

SUMMARY OF THE INVENTION

The present invention provides compounds that modulate, and preferably inhibit, activation of the alternative complement pathway. In certain embodiments, the present invention provides compounds that modulate, and preferably inhibit, Factor B activity and/or Factor B mediated complement pathway activation. Such Factor B modulators are preferably high affinity Factor B inhibitors that inhibit the catalytic activity of complement Factor B, such as primate Factor B and particularly human Factor B.

The compounds of the present invention inhibit or suppress the amplification of the complement system caused by C3 activation irrespective of the initial mechanism of activation (including for example activation of the classical, lectin or alternative pathways).

Various embodiments of the invention are described herein. It will be recognized that features specified in each embodiment may be combined with other specified features to provide further embodiments.

Within certain aspects, Factor B modulators provided herein are compounds of Formula I and salts and tautomers thereof:

In another embodiment, the invention provides a pharmaceutical composition comprising a therapeutically effective amount of a compound according to the definition of formula (I) or subformulae thereof and one or more pharmaceutically acceptable carriers.

In another embodiment, the invention provides a combination, in particular a pharmaceutical combination, comprising a therapeutically effective amount of the compound according to the definition of formula (I) or subformulae thereof and one or more additional therapeutically active agents.

The invention further provides methods of treating or preventing complement mediated diseases, the method comprising the steps of identifying a patient in need of complement modulation therapy and administering a compound of Formula (I) or a subformulae thereof. Complement mediated diseases include ophthalmic diseases (including early or neovascular age-related macular degeneration and geographic atrophy), autoimmune diseases (including arthritis, rheumatoid arthritis), Respiratory diseases, cardiovascular diseases.

Other aspects of the invention are discussed infra.

DETAILED DESCRIPTION OF THE INVENTION

As noted above, the present invention provides compounds that modulate Factor B activation and/or Factor B-mediated signal transduction of the complement system. Such compounds may be used in vitro or in vivo to modulate (preferably inhibit) Factor B activity in a variety of contexts.

In a first embodiment, the invention provides compounds of Formula I and salts and tautomers thereof, which modulate the alternative pathway of the complement system. Compounds of Formula I are represented by the structure:

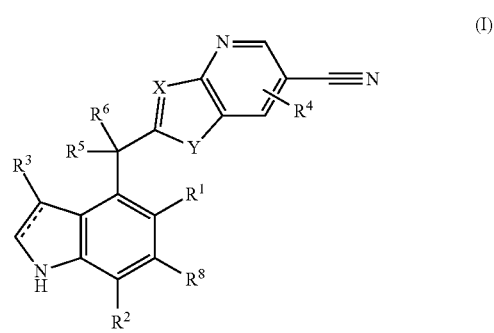

Wherein

⫽ is a single or double bond;

X is N or CH;

p is 0, 1, or 2;

Y is N(H), O or S;

$R^1$ is halogen, hydroxyl, $C_1$-$C_6$alkyl, $C_2$-$C_6$alkenyl, $C_3$-$C_6$cycloalkyl, $C_1$-$C_6$alkoxy, halo$C_1$-$C_6$alkyl, hydroxy$C_1$-$C_6$alkyl, amino$C_1$-$C_6$alkyl, $C_1$-$C_6$alkoxy$C_1$-$C_6$alkyl, $C_1$-$C_6$alkoxy$C_1$-$C_6$alkoxy, $C_3$-$C_6$cycloalkyl$C_1$-$C_6$alkoxy, halo$C_1$-$C_6$alkoxy, $S(O)_pC_1$-$C_6$alkyl, $CH_2NHC(O)C_1$-$C_4$alkyl or $OCH_2C(O)R^7$, $R^2$ is $C_1$-$C_6$alkyl, $C_1$-$C_6$alkoxy, hydroxy$C_1$-$C_6$alkyl or halogen;

$R^3$ is hydrogen, halogen, cyano, $C_1$-$C_4$alkyl, halo$C_1$-$C_4$alkyl, $CH_2C(O)R^7$, phenyl or 5 or 6 member heteroaryl having 1, 2 or 3 ring heteroatoms independently selected from N, O or S, wherein the phenyl or heteroaryl is optionally substituted with 0, 1, or 2 $C_1$-$C_4$alkyl groups, and wherein alkyl and haloalkyl optionally substituted with 0 or 1 hydroxy;

$R^4$ is 0, 1, or 2 substitutents independently selected at each occurrence from halogen and $C_1$-$C_6$alkyl;

$R^5$ is hydrogen, $C_1$-$C_6$alkyl, halo$C_1$-$C_6$alkyl, $C_3$-$C_6$cycloalkyl, phenyl or 5 or 6 member heteroaryl having 1, 2 or 3 ring heteroatoms independently selected from N, O or S; or $R^3$ and $R^5$ taken in combination form a divalent —$CH_2$—$CH_2$— or —$CH_2$—N(H)— group;

$R^6$ is hydrogen, hydroxy, amino, $C_1$-$C_6$alkyl, $C_1$-$C_6$alkoxy, $C_1$-$C_6$alkoxy$C_1$-$C_6$alkoxy, mono- and di-$C_1$-$C_4$alkylamino, amino $C_1$-$C_6$alkylamino, $[CR^A{}_2]_nR^{10}$, $O[CR^A{}_2]_nR^7$, $NHC(O)C_1$-$C_6$alkyl, $NHS(O_2)C_1$-$C_6$alkyl, $(CH_2)_nR^9$, $O(CH_2)_nR^9$, $O[CR^A{}_2]_nR^7$, $N(H)[CR^A{}_2]_nR^7$, $C(O)R^7$, $O[CR^A{}_2]_nC(O)R^7$, $N(H)$ $[CR^A{}_2]_nC(O)R^7$ or tetrazolyl;

or $CR^5R^6$, taken in combination, form a divalent carbonyl group, a divalent =$CH_2$ group or cyclopropyl which cyclopropyl is optionally substituted by $CO_2H$ or $CH_2OH$;

or when $R^5$ is hydrogen, then $R^6$ may also be selected from $[CR^A{}_2]_nR^7$ or $[CR^A{}_2]nC(O)R^7$;

n is 1, 2, 3 or 4;

$R^A$ is independently selected at each occurrence from hydrogen, halogen or $C_1$-$C_4$alkyl;

$R^7$ is hydroxy, $C_1$-$C_4$alkoxy, amino, or mono- and di-$C_1$-$C_4$alkylamino;

$R^8$ is hydrogen or halogen;

$R^9$ is a 5 member heteroaryl having 1 to 4 ring heteroatoms selected from N, O or S and optionally substituted with 0, 1, or 2 $C_1$-$C_4$alkyl groups; and $R^{10}$ is amino or mono- and di-$C_1$-$C_4$alkylamino.

In a second embodiment, the invention provides compounds, salts thereof and tautomers thereof of the first embodiment, according to Formula (Ia):

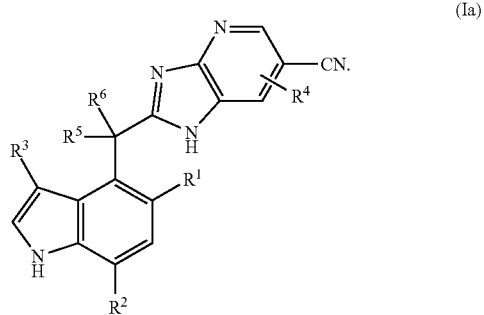

(Ia)

Compounds of Formula Ia (and Formula I when X is N and Y is NH) exist as a mixture of tautomers in which the hydrogen of the imidazole ring may tautomerize between the two nitrogen atoms of the imidazole ring, as follows:

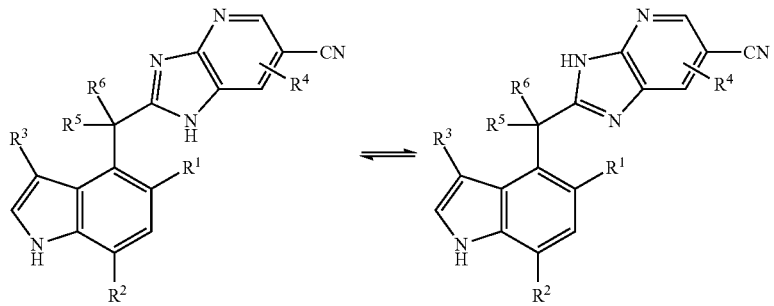

In a third embodiment, the invention provides compounds, salts thereof and tautomers thereof of the first or second embodiment in which $R^4$ is absent.

In a fourth embodiment, the invention provides compounds, salts thereof and tautomers thereof of any one of embodiments 1 to 3 in which $R^3$ is hydrogen, chloro or phenyl.

In a fifth embodiment, the invention provides compounds, salts thereof and tautomers thereof of any one of embodiments 1 to 4 in which $R^3$ is hydrogen.

In a sixth embodiment, the invention provides compounds, salts thereof and tautomers thereof of any one of embodiments 1 to 5 in which $R^2$ is methyl.

In a seventh embodiment, the invention provides compounds, salts thereof and tautomers thereof of any one of embodiments 1 to 6 in which $R^1$ is halogen, $C_1$-$C_4$alkyl, vinyl, cyclopropyl, $C_1$-$C_4$alkoxy, hydroxy$C_1$-$C_4$alkyl, $C_1$-$C_4$alkoxy$C_1$-$C_4$alkyl, $C_1$-$C_4$alkoxy$C_1$-$C_4$alkoxy, cyclopropyl$C_1$-$C_4$alkoxy, halo$C_1$-$C_4$alkoxy or $S(O)_2C_1$-$C_4$alkyl.

In a eighth embodiment, the invention provides compounds, salts thereof and tautomers thereof of any one of embodiments 1 to 8 in which $R^1$ is $C_1$-$C_4$alkyl, $C_1$-$C_4$alkoxy, cyclopropyl, bromo or difluoromethoxy.

In a ninth embodiment, the invention provides compounds, salts thereof and tautomers thereof of any one of embodiments 1 to 8 in which $R^5$ is hydrogen, methyl, ethyl. cyclopropyl or trifluoromethyl.

In a tenth embodiment, the invention provides compounds, salts thereof and tautomers thereof of any one of embodiments 1 to 9 in which $R^6$ is hydrogen, hydroxy, methoxy, amino, mono- and di-methylamino or $CH_2R^{10}$;

or when $R^5$ is hydrogen, then $R^6$ may also be selected from $CH_2R^7$ or $CH_2C(O)R^7$, $[CH_2]_2R^7$ or $[CH_2]_2C(O)R^7$;

$R^7$ is hydroxy, amino, $N(H)CH_3$ or $N(CH_3)_2$; and $R^{10}$ is amino, $N(H)CH_3$ or $N(CH_3)_2$.

In an eleventh embodiment, the invention provides compounds, salts thereof and tautomers thereof of any one of embodiments 1 to 10 in which $R^5$ is methyl or trifluoromethyl;

$R^6$ is hydroxy, methoxy, amino, methylamino or $CH_2R^7$; and $R^7$ is amino, $N(H)CH_3$ or $N(CH_3)_2$.

In a twelfth embodiment, the invention provides compounds, salts thereof and tautomers thereof of any one of embodiments 1 to 11 in which $R^1$ is $C_1$-$C_4$alkyl, $C_1$-$C_4$alkoxy, or cyclopropyl;

$R^2$ is methyl;

$R^3$ and $R^4$ are hydrogen;

$R^5$ is hydroxyl, amino, mono- and di-$C_1$-$C_2$alkylamino, $C_1$-$C_2$alkyl, or $C_1$-$C_2$alkoxy; and $R^6$ is hydrogen, amino, $C_1$-$C_2$alkyl, or trifluoromethyl.

In a thirteenth embodiment, the invention provides compounds, salts or tautomers thereof of any one of embodiments 1 to 11 in $R^5$ is methyl or trifluoromethyl; $R^6$ is hydroxy, methoxy, amino or, methylamino.

In a fourteenth embodiment, the invention provides compounds of embodiment 1 in which compound is selected from the group consisting of (+)-2-(1-amino-2,2,2-trifluoro-1-(5-methoxy-7-methyl-1H-indol-4-yl)ethyl)-3H-imidazo[4,5-b]pyridine-6-carbonitrile;

(−)-2-(1-amino-2,2,2-trifluoro-1-(5-methoxy-7-methyl-1H-indol-4-yl)ethyl)-3H-imidazo[4,5-b]pyridine-6-carbonitrile;

(+)-2-(hydroxy(5-methoxy-7-methyl-1H-indol-4-yl)methyl)-1H-imidazo[4,5-b]pyridine-6-carbonitrile;

(−)-2-(hydroxy(5-methoxy-7-methyl-1H-indol-4-yl)methyl)-1H-imidazo[4,5-b]pyridine-6-carbonitrile;

(+)-2-(1-hydroxy-1-(5-methoxy-7-methyl-1H-indol-4-yl)
ethyl)-3H-imidazo[4,5-b]pyridine-6-carbonitrile;
(−)-2-(1-hydroxy-1-(5-methoxy-7-methyl-1H-indol-4-yl)
ethyl)-3H-imidazo[4,5-b]pyridine-6-carbonitrile
(+)-2-(1-methoxy-1-(5-methoxy-7-methyl-1H-indol-4-yl)
ethyl)-3H-imidazo[4,5-b]pyridine-6-carbonitrile
(−)-2-(1-methoxy-1-(5-methoxy-7-methyl-1H-indol-4-yl)
ethyl)-3H-imidazo[4,5-b]pyridine-6-carbonitrile;
(+)-2-(2,2,2-trifluoro-1-(5-methoxy-7-methyl-1H-indol-4-
yl)-1-(methylamino)ethyl)-3H-imidazo[4,5-b]pyridine-6-
carbonitrile;
(−)-2-(2,2,2-trifluoro-1-(5-methoxy-7-methyl-1H-indol-4-
yl)-1-(methylamino)ethyl)-3H-imidazo[4,5-b]pyridine-6-
carbonitrile;
(+)-2-(1-amino-1-(5-methoxy-7-methyl-1H-indol-4-yl)
ethyl)-3H-imidazo[4,5-b]pyridine-6-carbonitrile;
(−)-2-(1-amino-1-(5-methoxy-7-methyl-1H-indol-4-yl)
ethyl)-3H-imidazo[4,5-b]pyridine-6-carbonitrile;
(+)-2-(1-(5-methoxy-7-methyl-1H-indol-4-yl)-1-(methyl-
amino)ethyl)-3H-imidazo[4,5-b]pyridine-6-carbonitrile;
(−)-2-(1-(5-methoxy-7-methyl-1H-indol-4-yl)-1-(methyl-
amino)ethyl)-3H-imidazo[4,5-b]pyridine-6-carbonitrile;
2-(2-(5-methoxy-7-methyl-1H-indol-4-yl)propan-2-yl)-3H-
imidazo[4,5-b]pyridine-6-carbonitrile;
(+)-2-(1-(5-ethyl-7-methyl-1H-indol-4-yl)-2,2,2-trifluoro-
1-hydroxyethyl)-3H-imidazo[4,5-b]pyridine-6-carboni-
trile;
(−)-2-(1-(5-ethyl-7-methyl-1H-indol-4-yl)-2,2,2-trifluoro-
1-hydroxyethyl)-3H-imidazo[4,5-b]pyridine-6-carboni-
trile;
(±)-2-(1-(5-ethyl-7-methyl-1H-indol-4-yl)-1-(methylamino)
ethyl)-3H-imidazo[4,5-b]pyridine-6-carbonitrile;
(±)-2-((5-cyclopropyl-7-methyl-1H-indol-4-yl)(hydroxy)
methyl)-3H-imidazo[4,5-b]pyridine-6-carbonitrile
(±)-2-(1-(5-cyclopropyl-7-methyl-1H-indol-4-yl)-1-hy-
droxyethyl)-3H-imidazo[4,5-b]pyridine-6-carbonitrile;
and
(±)-2-(1-amino-1-(5-cyclopropyl-7-methyl-1H-indol-4-yl)-
2,2,2-trifluoroethyl)-3H-imidazo[4,5-b]pyridine-6-carbo-
nitrile; and salts and tautomers thereof.

In another embodiment, pharmaceutical compositions are provided which comprise one or more pharmaceutically acceptable carriers and a therapeutically effective amount of a compound of any one of formulae (I) or (Ia), or a subformulae thereof.

In another embodiment, combinations, in particular pharmaceutical combinations, are provided which comprise a therapeutically effective amount of the compound of any one of formulae (I) or (Ia), or a subformulae thereof.

In another embodiment, methods of modulating complement alternative pathway activity in a subject are provided which methods comprise administering to the subject a therapeutically effective amount of any one of formulae (I) or (Ia), or a subformulae thereof.

In yet other embodiments, methods of treating a disorder or a disease in a subject mediated by complement activation, in particular mediated by activation of the complement alternative pathway, are provided, which methods comprise administering to the subject a therapeutically effective amount of the compound of any one of formulae (I) or (Ia), or a subformulae thereof.

In another embodiment, methods of treating age related macular degeneration in a subject are provided which methods comprise administering to the subject a therapeutically effective amount of the compound of any one of formulae (I) or (Ia), or a subformulae thereof.

In another aspect, the invention provides for the use of compounds of any one of formulae (I) or (Ia), or a subformulae thereof for use in the preparation of a medicament and more particularly for use in the manufacture of a medicament for the treatment of a disorder or disease in a subject mediated by complement activation or activation of the complement alternative pathway. In certain other aspects, the invention provides for the use of a compound according of any one of formulae (I) or (Ia), or a subformulae thereof in the treatment of age-related macular degeneration.

In one embodiment, the invention provides a combination, in particular a pharmaceutical combination, comprising a therapeutically effective amount of the compound according to the definition of formula (I), (Ia) or subformulae thereof or any one of the specifically disclosed compounds of the invention and one or more therapeutically active agents (preferably selected from those listed infra).

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of the following:
  (a) alkyl;
  (b) hydroxy (or protected hydroxy);
  (c) halo;
  (d) oxo, i.e., =O;
  (e) amino, alkylamino or dialkylamino;
  (f) alkoxy;
  (g) cycloalkyl;
  (h) carboxyl;
  (i) heterocyclooxy, wherein heterocyclooxy denotes a heterocyclic group bonded through an oxygen bridge;
  (j) alkyl-O—C(O)—;
  (k) mercapto;
  (l) nitro;
  (m) cyano;
  (n) sulfamoyl or sulfonamido;
  (o) aryl;
  (p) alkyl-C(O)—O—;
  (q) aryl-C(O)—O—;
  (r) aryl-S—;
  (s) aryloxy;
  (t) alkyl-S—;
  (u) formyl, i.e., HC(O)—;
  (v) carbamoyl;
  (w) aryl-alkyl-; and
  (x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryloxy" refers to both an —O-aryl and an 0-O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 8 heteroatoms selected from N, O or S.

Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The asterisk (*) indicated in the name of a compound designate a racemic mixture. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

All tautomeric forms are also intended to be included. In particular, the cyano substituted benzimidazoles of the invention may exist as a mixture of tautomeric forms, e.g., the 5-cyano-benzimidazole and 6-cyano-benzimidazole forms. Thus the N—H hydrogen may exchange between the ring nitrogens of the benzimidazole ring. These forms may interconvert at or above temperatures of about 0° C. For example, compounds of Formula (II) exist as a mixture of tautomeric forms which may readily interconvert at therapeutically relevant temperatures. For convenience, only one tautomeric form of the compounds are depicted in the instant application. However, one of ordinary skill in the art will recognize and appreciate that both tautomeric forms are contemplated to be within the scope of the invention.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, benzenesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (−)-2-(Hydroxy(5-methoxy-7-methyl-1H-indol-4-yl)methyl)-1H-imidazo[4,5-b]pyridine-6-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (+)-2-(1-Hydroxy-1-(5-methoxy-7-methyl-1H-indol-4-yl)ethyl)-3H-imidazo[4,5-b]pyridine-6-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (−)-2-(1-Methoxy-1-(5-methoxy-7-methyl-1H-indol-4-yl)ethyl)-3H-imidazo[4,5-b]pyridine-6-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (+2-(2,2,2-Trifluoro-1-(5-methoxy-7-methyl-1H-indol-4-yl)-1-(methylamino)ethyl)-3H-imidazo[4,5-b]pyridine-6-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (−)-2-(1-Amino-1-(5-methoxy-7-methyl-1H-indol-4-yl)ethyl)-3H-imidazo[4,5-b]pyridine-6-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides 2-(2-(5-Methoxy-7-methyl-1H-indol-4-yl)propan-2-yl)-3H-imidazo[4,5-b]pyridine-6-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (±)-2-(1-(5-Cyclopropyl-7-methyl-1H-indol-4-yl)-1-hydroxyethyl)-3H-imidazo[4,5-b]pyridine-6-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (±)-2-(1-Amino-1-(5-cyclopropyl-7-methyl-1H-indol-4-yl)-2,2,2-trifluoroethyl)-3H-imidazo[4,5-b]pyridine-6-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{124}$I, $^{125}$I respectively. The invention includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and salts thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In certain embodiments, selective deuteration of compounds of Formula (I) include deuteration of $R^1$, $R^3$, $R^5$ and/or $R^6$, for example when any of $R^1$, $R^3$, $R^5$ and/or $R^6$ are methyl, methoxy, or ethoxy, the alkyl residue is preferably deuterated, e.g. $CD_3$, $OCD_3$ or $OC_2D_5$. when $R^3$ is alkanoyl, e.g., $C(O)CD_3$.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (e.g., tissue regeneration and reproduction) (i) mediated by Factor B, or (ii) associated with Factor B activity, or (iii) characterized by activity (normal or abnormal) of the complement alternative pathway; or (2) reducing or inhibiting the activity of Factor B; or (3) reducing or inhibiting the expression of Factor B; or (4) reducing or inhibiting activation of the complement system and particularly reducing or inhibiting generation of C3a, iC3b, C5a or the membrane attack complex generated by activation of the complement alternative pathway. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Factor B and/or the complement alternative pathway; or at least partially reducing or inhibiting the expression of Factor B and/or the complement alternative pathway. The meaning of the term "a therapeutically effective amount" as illustrated in the above embodiment for Factor B and/or the complement alternative pathway.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis- (Z)- or trans- (E)- form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 250° C., including, for example, from approximately −80° C. to approximately 250° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

The following Examples serve to illustrate the invention without limiting the scope thereof.

General Synthetic Aspects

The following Examples serve to illustrate the invention without limiting the scope thereof.

Typically, the compounds of formula (I) can be prepared according to the Schemes provided below.

Compounds such as 5, wherein PG is a protecting group (preferably Boc or Ts), $R^a$ is halo or alkyl, and $R^b$ is alkoxyl, and $F^a$ is hydrogen of fluoro can be prepared by the general method outlined in Scheme 1.

Scheme 1

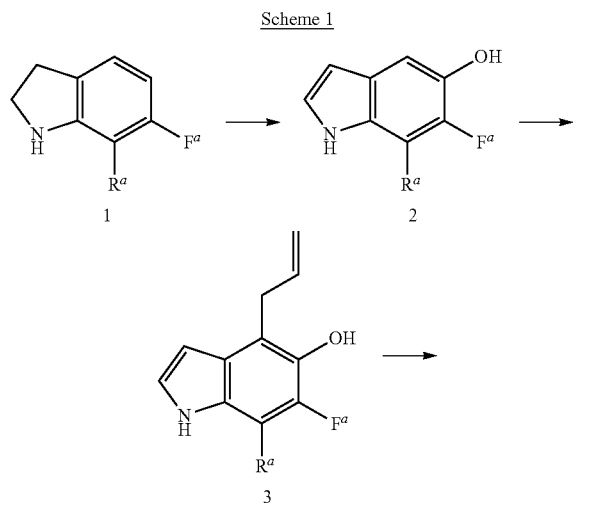

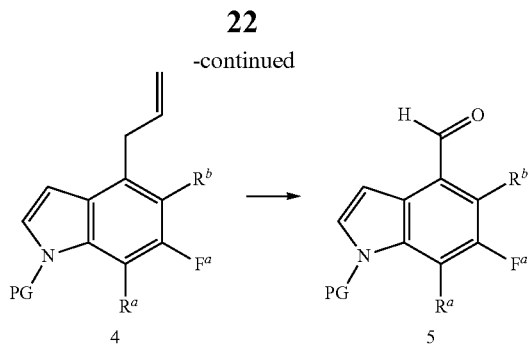

Transformation of indoline 1 to the corresponding 5-hydroxyindole 2 can be accomplished by treatment with potassium nitrosodisulfonate preferably in a solvent mixture of acetone/aq. buffer at pH=7 either at 0° C. or room temperature. The hydroxyl group of 2 can then be alkylated with allyl alcohol utilizing a Mitsunobu type reaction in a suitable solvent such as toluene. The product can then be converted to C-allyl derivatives such as 3 by thermally promoted sigmatropic rearrangement at temperatures between 200° C. and 250° C. without the use of solvent. Compound 3 can then be reacted with alcohols (e.g. MeOH, BnOH) utilizing Mitsunobu-type conditions permitting differentiation at $R^b$. Subsequent protection of the nitrogen of the indole employing TsCl and an appropriate base, preferably NaH, or alternatively with Boc$_2$O in the presence of a catalytic amount of DMAP can afford compounds such as 4. Isomerization of the double bond of 4 can be accomplished via treatment with Pd(OAc)$_2$ in hexafluoroisopropyl alcohol (HFIPA). Cleavage of the olefin can then be effected by reaction with osmium tetraoxide and sodium periodate to afford 5.

Compounds such as 5, wherein PG is a protecting group (preferably Boc), $R^a$ is alkyl, $R^b$ is alkoxyl, and $F^a$ is hydrogen can be also prepared by formylation of indole 5a using Vilsmeier-type reagents such as N-(chloromethylene)-N-methylbenzenaminium chloride in acetonitrile at temperatures between 0° C. and room temperature as shown in Scheme 1a.

Scheme 1a

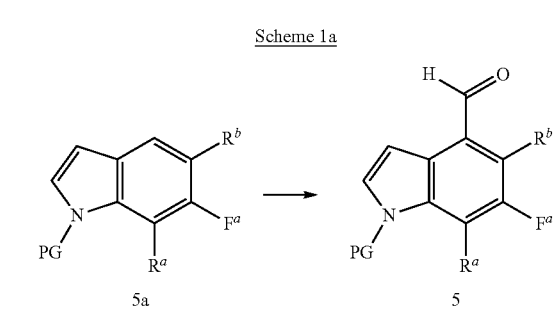

Compounds such as 10, wherein is $X^a$ is —Cl, —Br, or —SMe, can be prepared according to Scheme 2.

Scheme 2

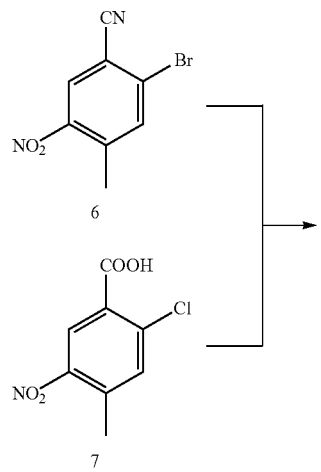

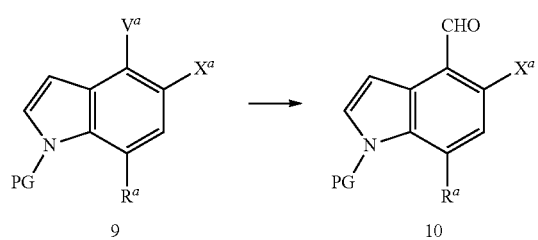

Scheme 3

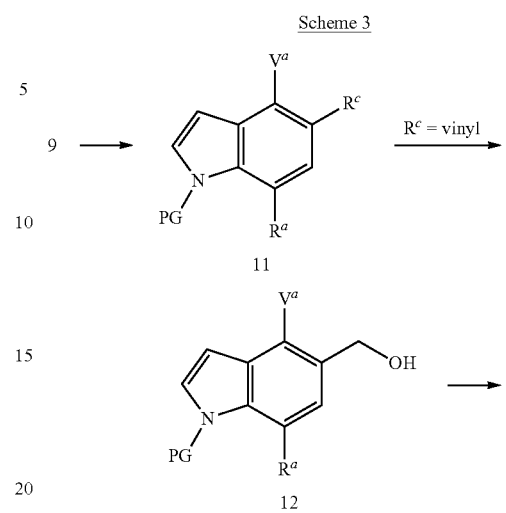

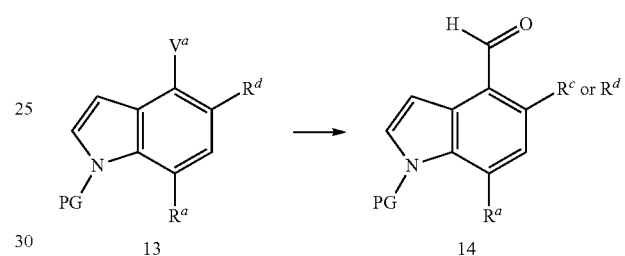

Nucleophilic aromatic substitution of 6 (CAS#1202858-65-8) can be achieved by sodium thiomethoxide in DMF at 60° C. to afford 8 ($X^a$=SMe). Alternatively, 7 (CAS#101580-96-5) can be transformed into 8 ($X^a$=Cl, $V^a$=CH$_2$OTHP) by reduction employing 1,1,1-trichloro-2-methylpropan-2-yl carbonochloridate and NaBH$_4$, followed by protection of the resulting hydroxyl with 3,4-dihydro-2H-pyran in the presence of TsOH. Transformation of 8 ($V^a$ is either —CN or —CH$_2$—OTHP) to the indole 9 can be achieved by Bartoli reaction using vinylmagnesium bromide in THF at temperatures ranging from −78° C. to room temperature, followed by protection of the indole. Protection can be effected by employing TsCl and an appropriate base preferably NaH, or alternatively protection can be accomplished with Boc$_2$O in the presence of a catalytic amount of DMAP. The aldehyde 10 can be accessed by when $V^a$=CN by reduction with DIBAL followed by acid hydrolysis preferably employing aq. HCl. Alternatively when $V^a$=CH$_2$OTHP 10 can be accessed by deprotection of the THP protecting group via acid mediated hydrolysis preferably employing TsOH in EtOH, followed by oxidation preferably using MnO$_2$ or SO$_2$-pyridine complex.

Compounds such as 14, wherein $R^c$ is alkyl and $R^d$ is —CH$_2$O-alkyl, or —CH$_2$— phthaloyl, can be prepared according to Scheme 3.

Indole 9 ($X^a$=Cl or Br, $V^a$=CN or CH$_2$OTHP) can be transformed to 11 wherein $R^c$=alkyl or vinyl utilizing a Suzuki-coupling with an appropriate boronate (such as alkyl trifluoroborates, or 2,4,6-trivinylcyclotriboroxane-pyridine complex). Alternatively a Negishi-type coupling employing an alkylzinc halide can be used in place of the Suzuki reaction. When $R^c$=vinyl 11 can be further transformed into 12 by a dihydroxylation preferably employing ADmix-α, followed by oxidative cleavage using NaIO$_4$ and reduction of the resulting aldehyde with NaBH$_4$. Alkylation of the hydroxyl group of 12 can be achieved by deprotonation with an appropriate base, preferably NaH, and reaction with an appropriate electrophile such as MeI or SEM-Cl to afford 13. Alternatively 12 can undergo Mitsunobu reaction with phthalimide. Lastly, indoles of type 13 can be converted to 14 in accordance with Scheme 2 (i.e. 9→10).

Aldehydes such as 18 or 19 can be prepared as described in Scheme 4.

Scheme 4

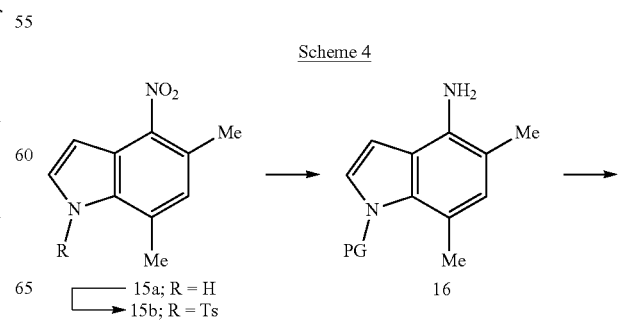

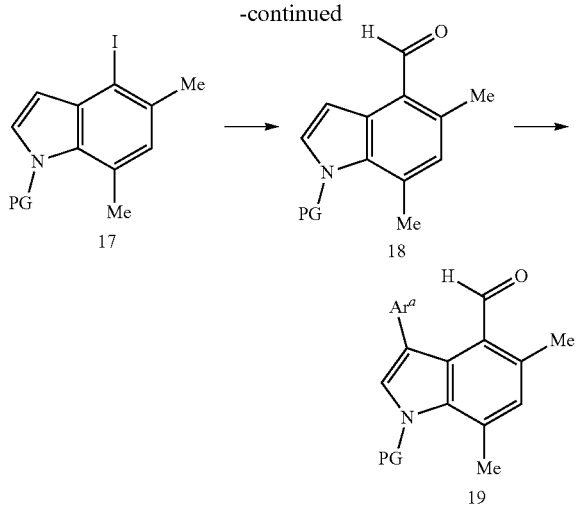

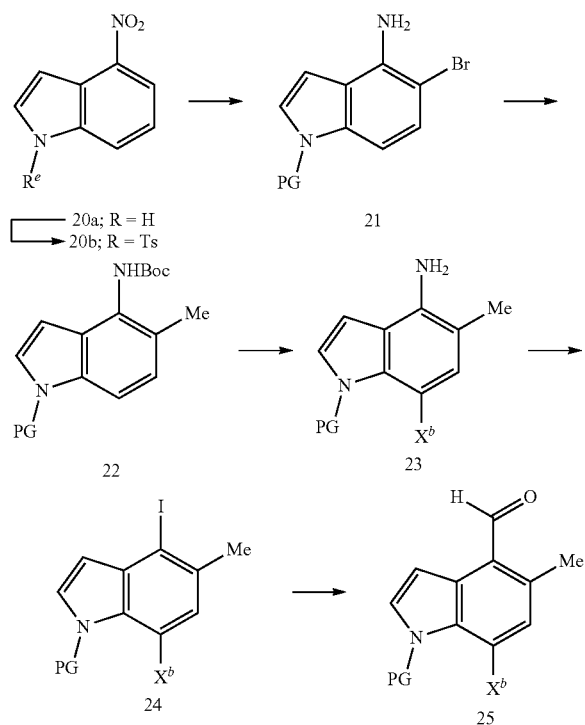

Indole 15a (CAS#1190314-35-2) can be protected by employing TsCl and an appropriate base preferably NaH to afford 15b. Reduction of the nitro functionality preferably by employing zinc metal in a solvent mixture of EtOAc/MeOH can afford aniline 16, which can be converted to iodide 17 upon treatment with NaNO$_2$, followed by I$_2$. Treatment of 17 with butyl lithium in the presence of DMF can provide the aldehyde 18. Further elaboration can be accomplished by employing NBS to effect bromination of the indole, followed by Suzuki-coupling with an appropriate aryl or heteroaryl boronate.

Compounds such 25 where $X^b$=Cl, Br can be prepared by the sequence described in Scheme 5.

Indole 20a (CAS#4769-97-5) can be protected by employing TsCl and an appropriate base preferably NaH to afford 20b. Reduction of the nitro functionality of 20b preferably employing zinc metal in a solvent mixture of EtOAc/MeOH followed by bromination preferably with NBS can afford 21. Boc protection of the aniline 21 followed by Suzuki-coupling using potassium methyltrifluoroborate can afford 22. Acid mediated deprotection of the Boc group of 22, followed by halogenation using NBS or NCS can yield halides of type 23. Transformation of the aniline 23 to aldehyde 25 can be accomplished in accordance with Scheme 4 (i.e. 17→18).

Heterocycles of type 26 wherein: $W^a$ is N-SEM, O, or S; $Y^a$ can be H, halo; $R^f$ is halo or alkyl; and Q=N or CH, can be employed to access compounds such as 28 as outlined in Scheme 6.

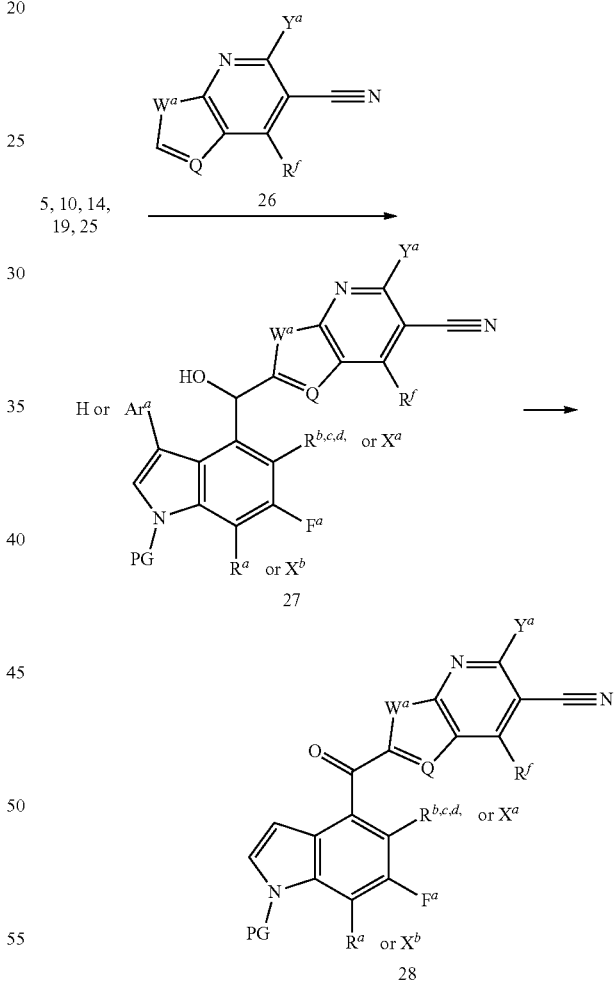

Nucleophilic addition of 26 into aldehydes of type 5, 10, 14, 19, 25 can be achieved with an appropriate base preferably LDA at temperatures between 0° C. and −78° C. Oxidation of the resulting hydroxyl group of 27 can be achieved by using an oxidant such as MnO$_2$ to afford ketones of type 28.

Compounds such as 30, wherein $R^g$ is alkyl, aryl or —CF$_3$ and $R^h$ is -alkyl, or substituted alkyl, can be prepared by the general method outlined in Scheme 7.

Scheme 7

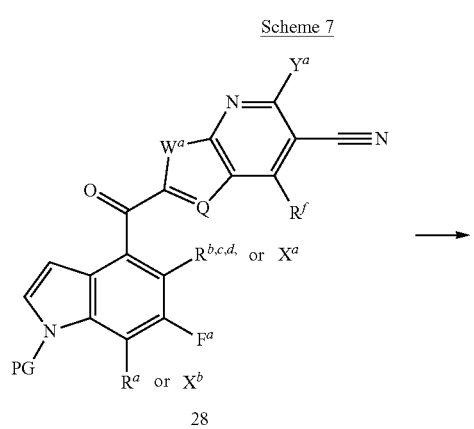

Scheme 8

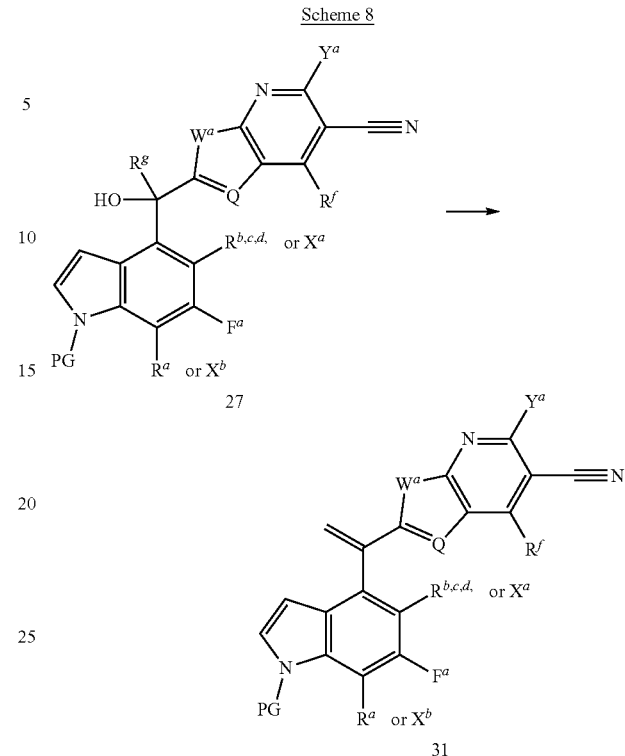

Compounds such as 32 ($R^b$=alkoxy) can be prepared by hydrogenolysis of compounds of type 29a where in $R^b$=OBn in Scheme 7, followed by alkylation with an appropriate electrophile (e.g. MeI or BrCH$_2$COOMe) in the presence of a suitable base such as Cs$_2$CO$_3$ as shown in Scheme 9.

Scheme 9

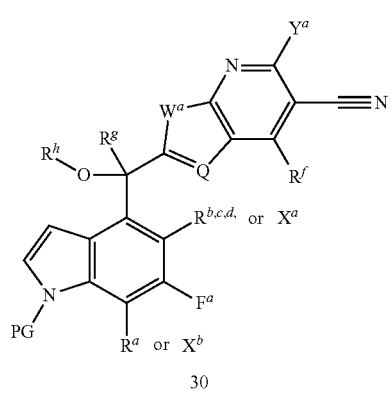

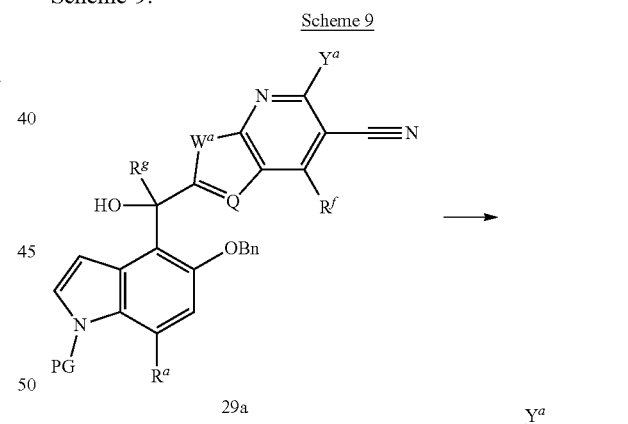

Ketones of type 28 can afford alcohols of type 29 by addition of an appropriate nucleophile, preferably a Grignard reagent. Alternatively, CF$_3$-TMS can be employed in the presence of a fluoride source such as TBAF. 29 can be further elaborated via alkylation of the hydroxyl with an appropriate electrophile such as MeI or methyl bromoacetate in the presence of strong base preferably NaH to furnish compounds of type 30.

Alkenes of type 31 can be prepared by treatment of the tertiary alcohol 29 ($R^g$=Me) with MsCl in the presence of base such as Et$_3$N and catalytic amount of DMAP at 0° C., followed by warming to room temperature as shown in Scheme 8.

Compound such as 34, wherein $R^g$ is equal to H or alkyl or CF$_3$, can be prepared as described in Scheme 10.

Scheme 10

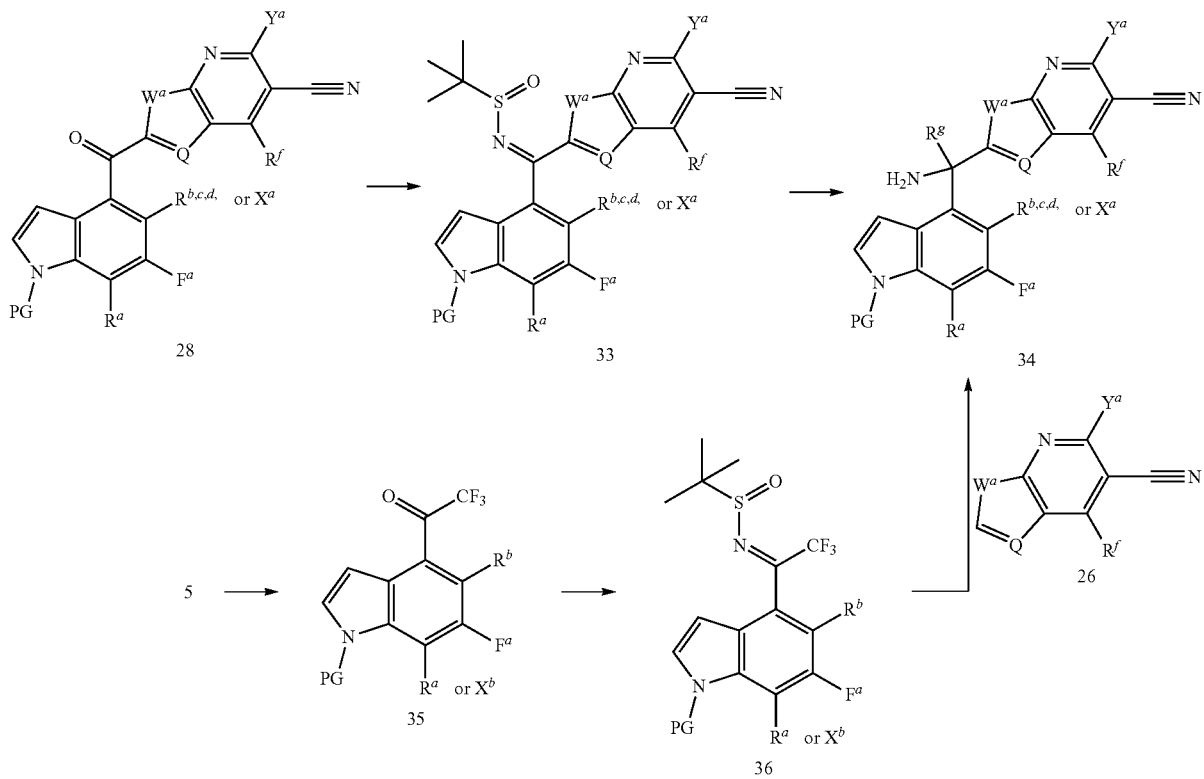

The ketone 28 can be transformed into the sulfinyl imine 33 by employing a dehydrating reagent such Ti(O-i-Pr$_4$) in the presence of tert-butyl sulfinamide without the need for additional solvent. Alternatively, the dehydration can be achieved by utilizing Zr(O-t-Bu)$_4$ in a suitable solvent such as toluene. The sulfinyl imine 33 can be reacted with a suitable organometallic nucleophile such as MeMgI, followed by treatment with HCl in MeOH to furnish 34. Alternatively, 33 can be reduced with NaBH$_4$ in MeOH to afford compounds wherein R$^g$=H, and the resulted sulfinyl group can then be removed by treatment with HCl in MeOH to afford 34. Compounds such as 34 wherein R$^g$=CF$_3$, especially when W$^a$=O and Q=N can be accessed by reacting 33 with trifluoromethyltriethylsilane in presence of tetramethylammonium fluoride in THF at temperatures between 0° C. and room temperature, followed by removal of the sulfinyl group by treatment with HCl in MeOH.

Compounds such 34, wherein R$^g$ is CF$_3$, can also be prepared starting from aldehydes such as 5. For example, treating 5 with trifluoromethyltrimethylsilane in presence of TBAF in THF at temperatures between 0° C. and room temperature, followed by oxidation using for example Dess-Martin Periodinane (CAS#87413-09-0) in DCM can afford ketone 35. Ketone 35 can be transformed into the sulfinyl imine 36 by employing a dehydrating reagent such Ti(O-i-Pr$_4$) in the presence of tert-butyl sulfinamide without the need for additional solvent. Alternatively, the dehydration can be achieved by utilizing Zr(O-t-Bu)$_4$ in a suitable solvent such as toluene. Nucleophilic addition of 26 into sulfinyl imine 36 can be achieved, especially when Q=N and W$^a$=N-SEM, with an appropriate base preferably LDA at temperatures between 0° C. and −78° C. Removal of sulfinyl group to provide 34 can be accomplished by treatment with HCl in MeOH.

Compound such as 37 wherein R$^h$ is Me, —Ac, or -Ms can be prepared according to Scheme 11.

Scheme 11

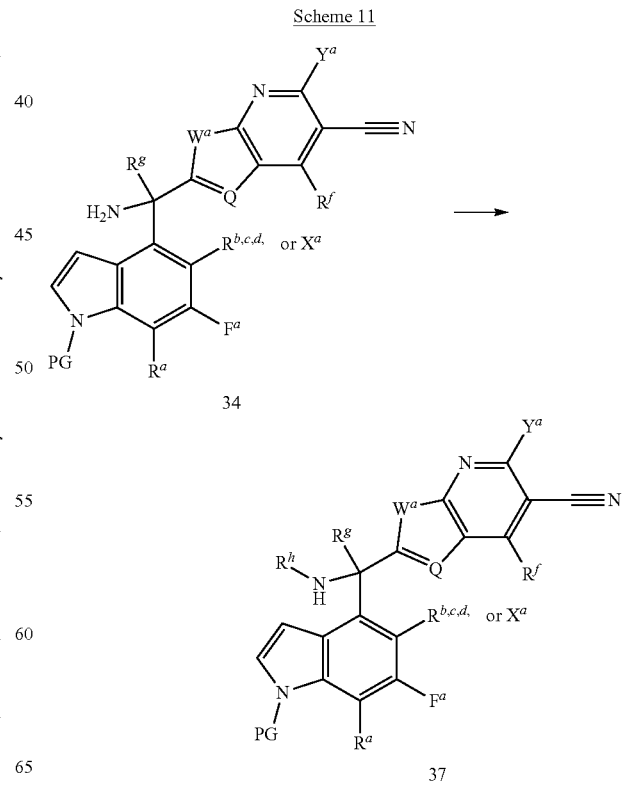

Amine 34 ($R^g$=H) can be reacted with a variety of electrophiles such as MeI, MsCl, AcCl in the presence of an appropriate base (e.g. DIPEA) to furnish 37 wherein $R^g$=H. Alternatively, when $R^g$=Me the amine in 34 can be first protected utilizing neat Boc$_2$O at 60° C.

Compounds such as 41, especially when Q=N and wherein $R^g$ is equal to methyl or $C_1$-$C_4$alkyl and $R^d$ is equal to H, methyl or $C_1$-$C_4$alkyl, and can be prepared according to Scheme 12.

Scheme 12

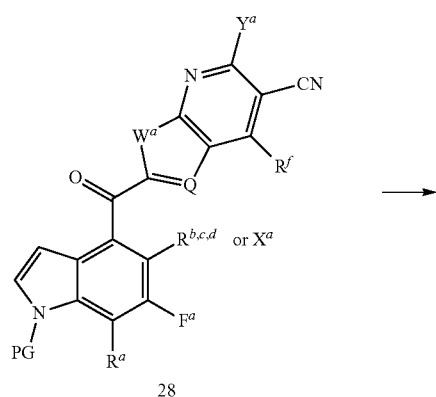
28

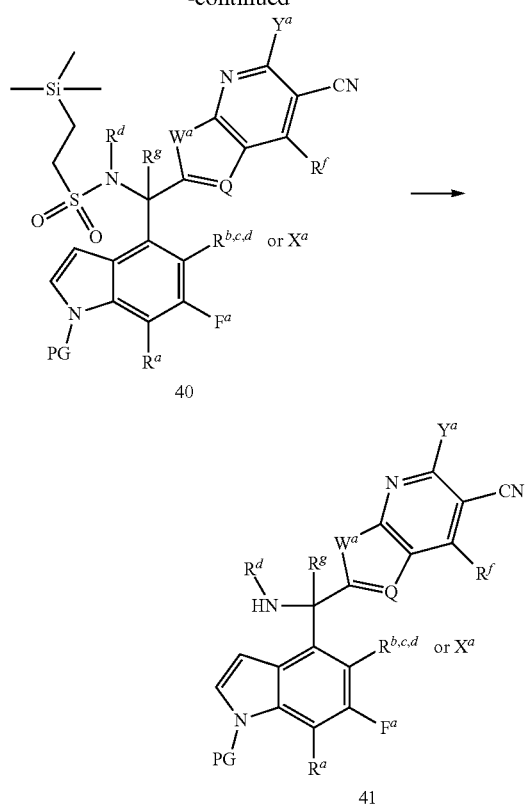
40

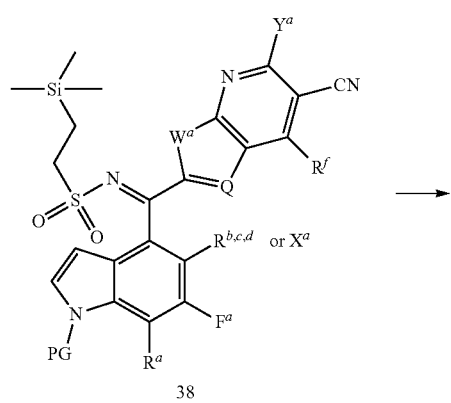
38

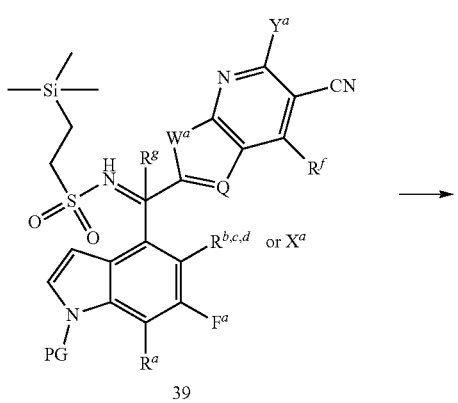
39

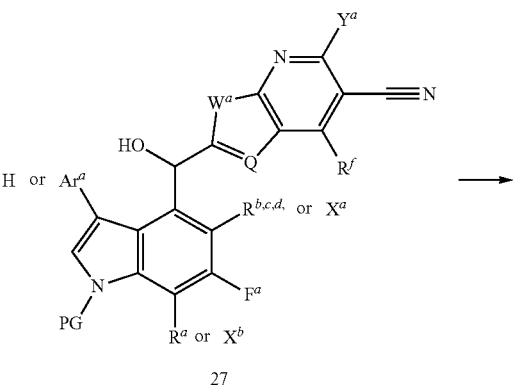
41

Ketones of type 28, can be reacted with 2-(trimethylsilyl)ethanesulfonamide in the presence of a Lewis Acid, preferably Zr(OtBu)$_4$ to afford imines of type 38. The imine can be reacted with alkyl Grignards such as methylmagensium iodide to afford sulfonamides of type 39. The resulting sulfonamide can be alkylated by reaction with a base in the presence of an alkyl halide, preferably K$_2$CO$_3$ in the presence of MeI to furnish compounds of type 40. Compounds such 39 and 40 can undergo global be deprotection via treatment of TBAF in THF to afford compounds of type 41.

Compound such as 42, can be prepared by the general method outlined in Scheme 13.

Scheme 13

27

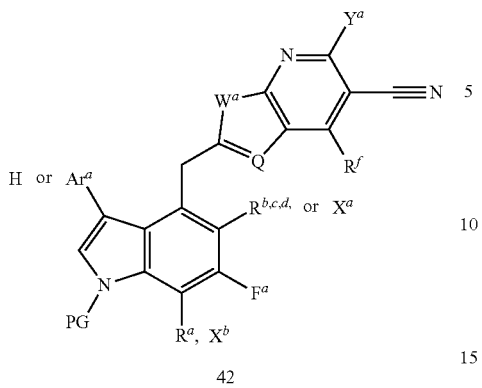

42

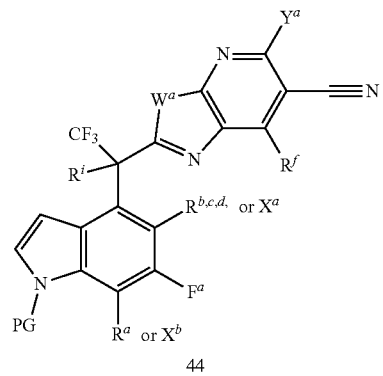

44

Compounds of the type 42 can be obtained by reaction compound type 27 with MsCl in the presence of a mild base such as triethylamine in aprotic solvents such as DCM at rt followed by reaction of the product with Zn in acetic acid at rt.

Compounds such as 44, especially when $W^a$=NSEM and wherein $R^i$ is $NH_2$ or N-alkyl, can be prepared as described in Scheme 14.

Removal of the SEM group from 29 ($W^a$=N-SEM, $R^g$=$CF_3$) to provide 43 can be accomplished by treatment with HCl in MeOH at 60° C., or by employing TBAF in the presence of ethylenediamine in THF at temperatures between room temperature and 70° C. preferably 60° C. Treatment of 43 with $SOCl_2$ in the presence of a catalytic amount of DMF in $CH_3Cl$ at 60° C. followed by reaction with alcoholic solutions of amines such 2M ammonia in EtOH or 33% methylamine in EtOH can furnish amines of type 44.

Compounds of type 47, wherein: $R^j$ is equal to H or $R^g$; $R^k$ is OH, $OR^h$, $NH_2$, $NHR^h$ or $R^i$; or $R^j$ and $R^k$ taken together to give =$CH_2$ or =O; or $R^j$=$R^k$=H: can be obtained by deprotections outlined in Scheme 15.

Scheme 14

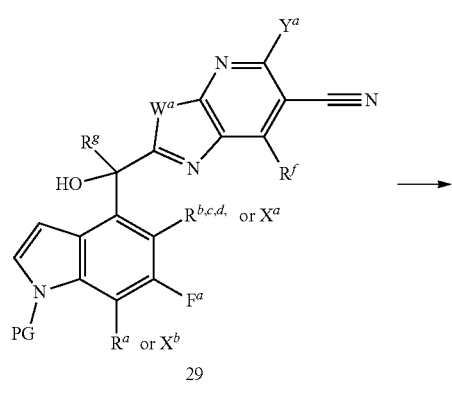

29

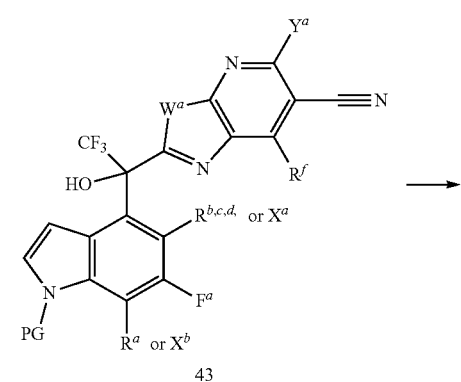

43

Scheme 15

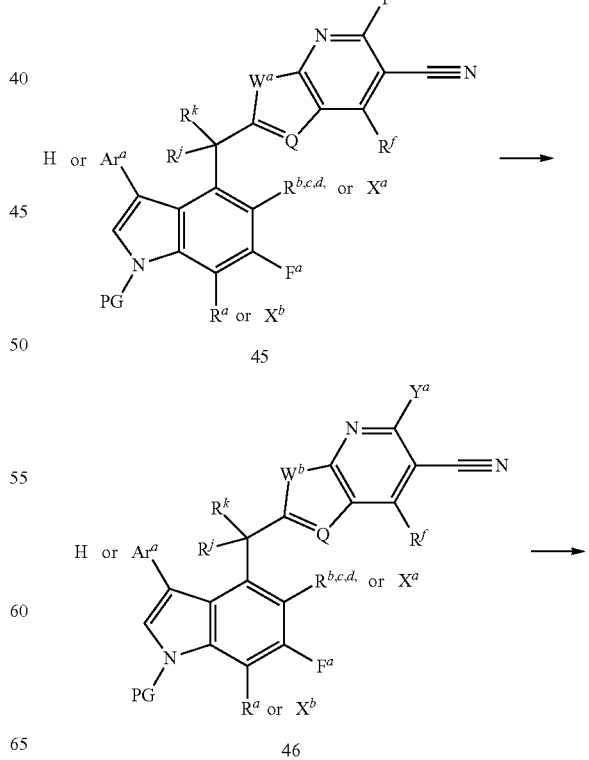

45

46

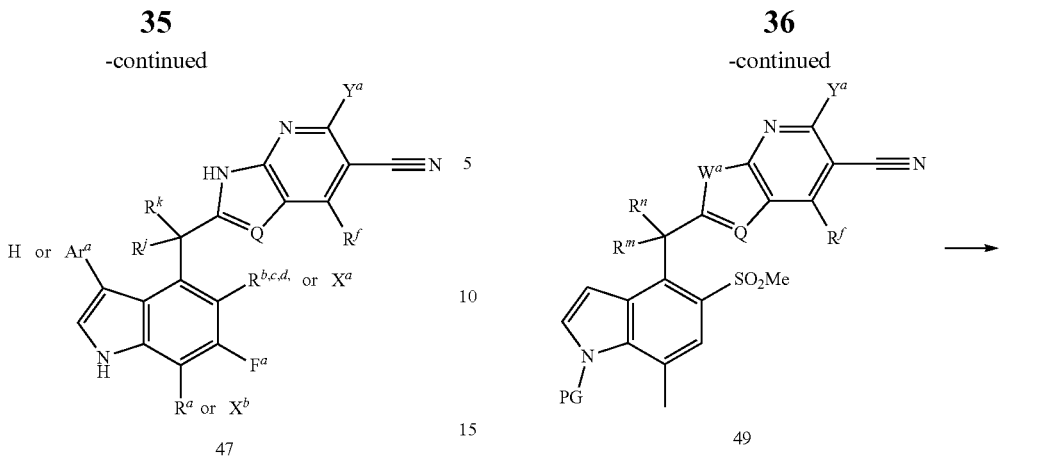

47

Deprotection of 48 (which process is also suitable for deprotection of other compounds of the invention such as 28, 30, 31, 32, 34, 37, 41, 42, 44 supra) is shown here. Removal of the SEM group of 45 when $W^a$=N-SEM can be achieved by employing an appropriate acid solution preferably HCl in MeOH, $BF_3$-$Et_2O$ in $CH_2Cl_2$, or $LiBF_4$ in aqueous $CH_3CN$ at the temperatures between 0° C. to 70° C. Alternatively, TBAF preferably in the presence of ethylenediamine at temperatures between 50° C. to 70° C. in THF can be used to remove the SEM group of 45. Finally, deprotection of PG in indole 46 wherein $W^b$=NH, O, or S, can be achieved by treatment with KOH in the presence of primary amine preferably isoamylamine in alcholic solvent such as EtOH at temperatures between 80° C. to 100° C. to afford 47 when PG=Ts. Alternatively $Cs_2CO_3$ in alcoholic solvents such as MeOH at elevated temperature preferably 60° C. can provide 47 when PG=Boc. Alternatively HCl in anhydrous solvent such as dioxane can be employed when PG=Boc to afford compounds such as 47.

Compound 50, wherein $W^b$=NH, 0 or S and especially when $W^a$=NSEM ($W^b$=NH) and Q=N and $R^m$ is H or Me and $R^n$ is OH, or OMe in Scheme 6 and Scheme 7, can be obtained as outlined in Scheme 16.

Sulfide 48 can be oxidized by ammonium molybdate tetrahydrate in the presence of hydrogen peroxide to provide sulfone 49. Removal of SEM group and then PG in accordance with Scheme 15 can afford compound of type 50.

Compounds such as 53, wherein: $R^p/R^q$ taken in combination can be H and $NH_2$, Me and $NH_2$, $CF_3$ and OH, $CF_3$ and $NH_2$, or $CF_3$ and NH-alkyl especially when $W^a$=NSEM ($W^b$=NH) and Q=N: can be obtained as outlined in Scheme 17.

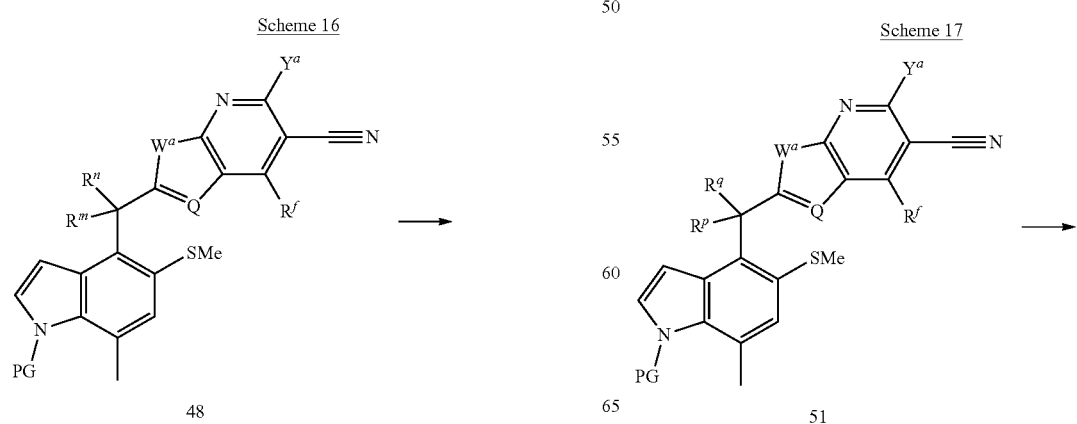

-continued

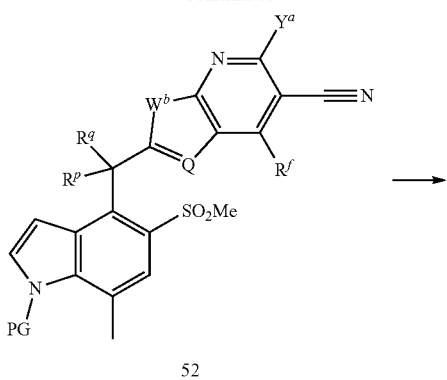

52

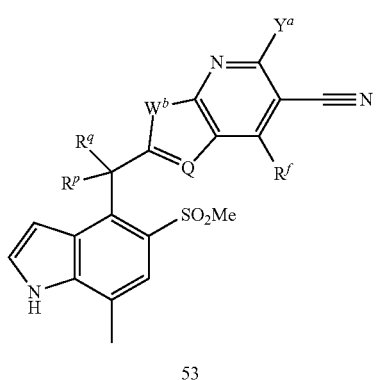

53

52 can be obtained by removal of the SEM group of 51 by treatment with HCl in MeOH at 60° C., followed by oxidation of the sulfide by employing ammonium molybdate tetrahydrate in the presence of hydrogen peroxide. Removal of PG can afford 53 according to Scheme 15.

Compounds such as 55, wherein R$^r$ is halo, —CF$_3$, —CN, methyl, 2,2,2-trifluoro-1-hydroxyethyl) especially when W$^b$=NH can be prepared as shown in Scheme 18.

Scheme 18

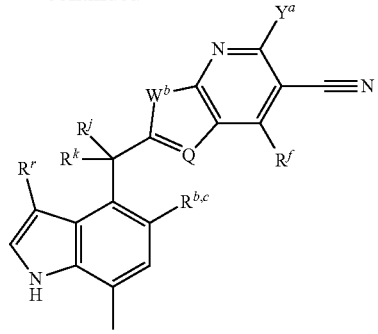

54

-continued

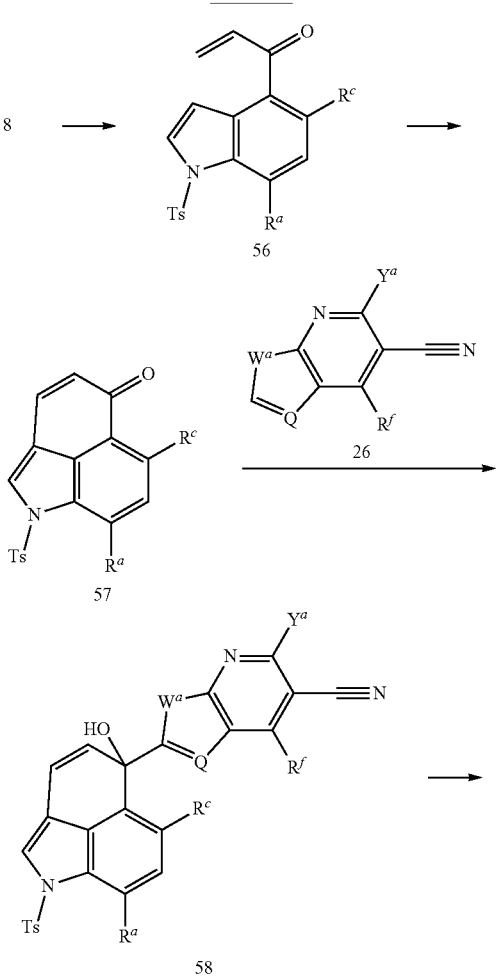

55

Indole 54 can be reacted with an appropriate electrophile such as NCS, chlorosulfonyl isocyanate, in suitable solvent such as DMF to furnish 55 (e.g. R$^r$=Cl, CN). Alternatively, 50 can be reacted with anhydrides and chloro-imminium ions followed by reductions with LiBH$_4$ in THF to afford compounds of type 55 wherein R$^r$ is equal to alkyl or hydroxy substituted alkyls.

Compound such as 60 especially when W$^a$=NSEM (W$^b$=NH) and Q=N can be prepared according to Scheme 19.

Scheme 19

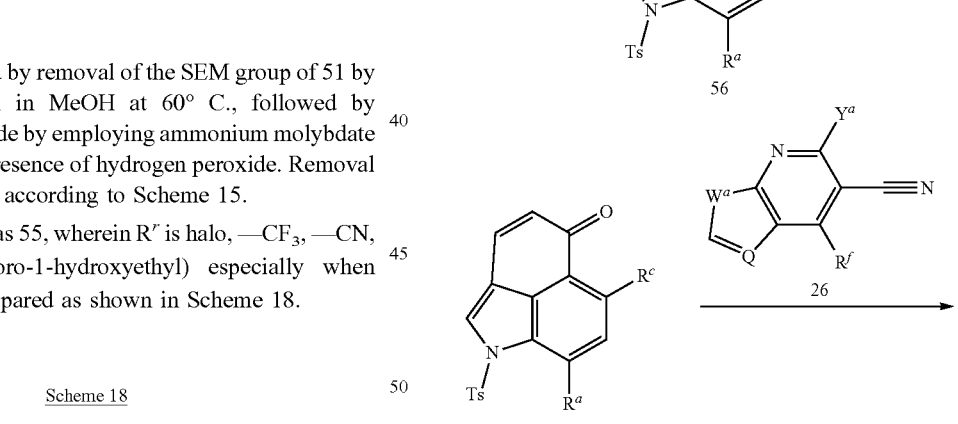

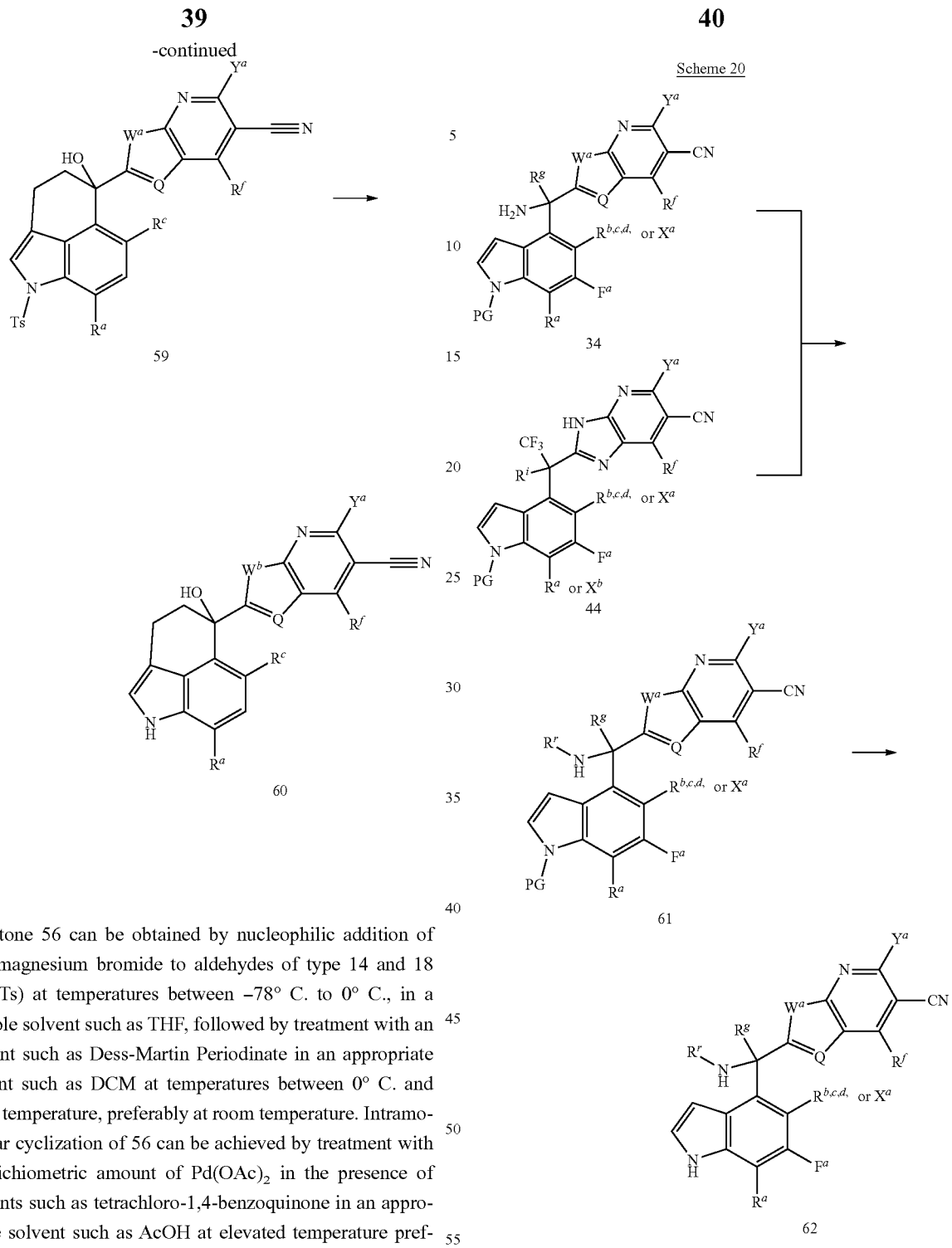

Ketone 56 can be obtained by nucleophilic addition of vinylmagnesium bromide to aldehydes of type 14 and 18 (PG=Ts) at temperatures between −78° C. to 0° C., in a suitable solvent such as THF, followed by treatment with an oxidant such as Dess-Martin Periodinate in an appropriate solvent such as DCM at temperatures between 0° C. and room temperature, preferably at room temperature. Intramolecular cyclization of 56 can be achieved by treatment with a stoichiometric amount of Pd(OAc)$_2$ in the presence of oxidants such as tetrachloro-1,4-benzoquinone in an appropriate solvent such as AcOH at elevated temperature preferably 100° C. to afford 57. Nucleophilic addition of 26 ($W^a$=N-SEM, Q=N) can be achieved to provide 58 similarly to the examples in Scheme 6. 58 can be hydrogenated in the presence of Pd/C in a suitable solvent such as MeOH under H$_2$ atmosphere to provide 59. Deprotection of SEM and Ts groups as shown in Scheme 15 can afford 60.

Compound such as 62 where $R^r$ is -alkyl, or substituted alkyl, can be prepared by the general method outlined in Scheme 20.

Indole 34 and 44 (where $R^i$=NH$_2$), prepared as shown in Scheme 10 and 14 can be reacted with the appropriate aldehyde (such as ethyl glyoxylate) in the presence of a mild reducing agent such as NaBH$_4$ or sodium triacetoxyborohydride, in alcoholic solvents, such as MeOH to give compound 61. Indole 62 can be obtained after deprotection of the protecting groups as shown in Scheme 15.

Compound such as 65 and 66 where $R^s$ and $R^t$ can be -alkyl, substituted alkyl or carboxy, and especially when $W^a$ is N-SEM or O ($W^b$ is N—H or O) and Q=N can be accessed by the general method outlined in Scheme 20.

Scheme 21

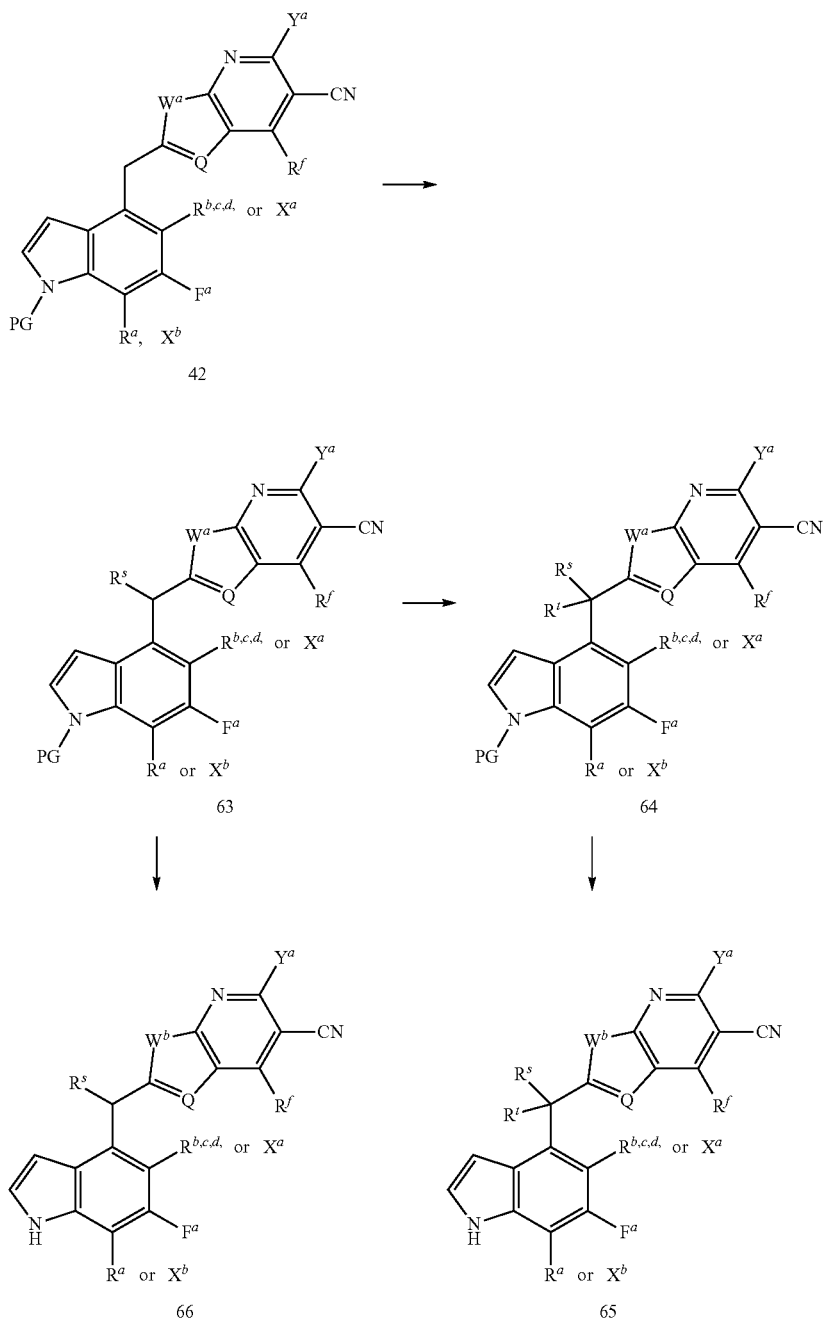

Indole 42 can be deprotonated with a suitable base such as NaH (especially when using MeI as the electrophile), LiHMDS or potassium tert-butoxide (with 18-crown-6) in a suitable solvent, such as THF (for LiHMDS and potassium tert-butoxide) and DMF (for NaH) and the anion quenched with the appropriate electrophiles such as: MeI, methyl bromoacetate, ethyl chloroformate, methyl acrylate to obtain compound 63. 63 can be further functionalized to introduce further benzylic substitutions ($R^t$) to give compound 64 using similar deprotonation/quench strategy as of 63. 63 and 64 can be deprotected using sequences presented in Scheme 15. When $R^s$ and/or $R^t$ bear an ester moiety, this can be hydrolyzed to the carboxylic acid using bases such as NaOH or $Cs_2CO_3$ in protic solvents such as MeOH and/or water at temperatures that range from room temperature to 60° C. In other examples where $R^s$ and/or $R^t$ bear an ester moiety and especially when $W^b$=O, 63 or 64 can be reacted with $SnCl_4$ in dichloromethane at temperatures between 0° C. and room temperature to allow for deprotection of protecting groups.

Compound such as 69, especially when $W^a$ is N-SEM or O ($W^b$ is N—H or O) and Q=N can be accessed by the general method outlined in Scheme 22.

Scheme 22

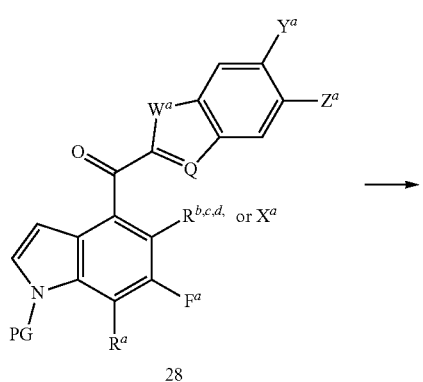

28

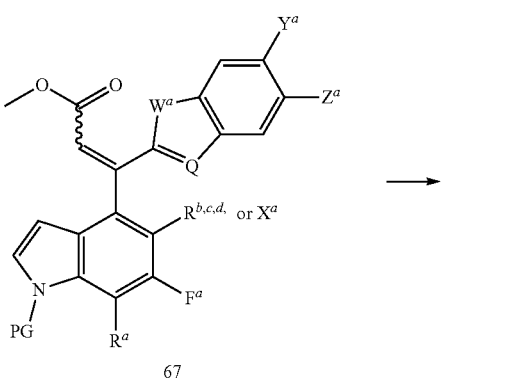

67

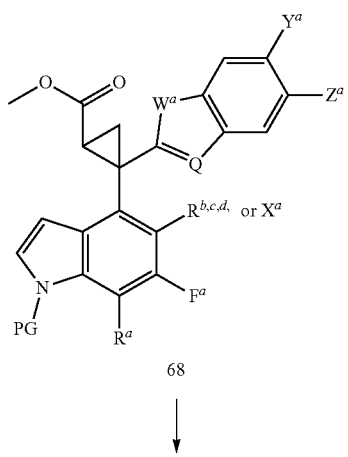

68

↓

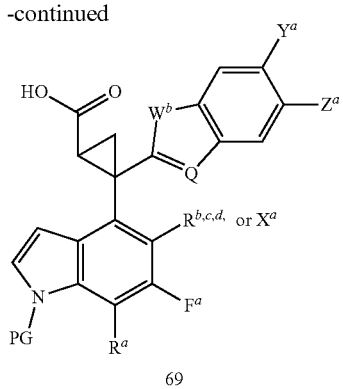

69

Ketone 28 can be reacted with methyl(triphenylphosphoranylidene)acetate in an appropriate solvent, such as toluene, at 110° C. to afford compound of type 67. 67 can be reacted with trimethylsulfoxonium iodide and a base such as NaH in the presence of DMSO at room temperature to afford compound 68. 68 can be reacted with $SnCl_4$ in dichloromethane at temperatures between 0° C. and room temperature to allow deprotection of Boc and SEM groups whilst lithium iodine in pyridine can hydrolyze the ester moiety to the wanted carboxylic acid of compound of type 69.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

Compounds of the invention and intermediates can also be converted into each other according to methods generally known to those skilled in the art.

All tautomeric forms are also intended to be included. In particular, the cyano substituted imidazo[4,5-b]pyridines of the invention may exist as a mixture of tautomeric forms, e.g., the 1H-imidazo[4,5-b]pyridine and 3H-imidazo[4,5-b]pyridine forms. Thus the N—H hydrogen may exchange between the ring nitrogens of the benzimidazole ring. These forms may interconvert at or above temperatures of about 0° C. For example, compounds of Formula (I) exist as a mixture of tautomeric forms which may readily interconvert at therapeutically relevant temperatures. For convenience, only one tautomeric form of the compounds are depicted in the instant application. However, one of ordinary skill in the art will recognize and appreciate that both tautomeric forms are contemplated to be within the scope of the invention.

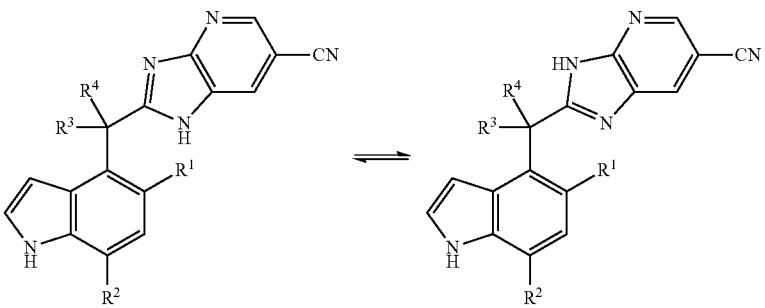

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Ophthalmic formulations, eye ointments, powders, solutions, suspensions and the like, for topical administration are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (a g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds of formula I in free form or in pharmaceutically acceptable salt form, exhibit valuable pharmacological properties, e.g. Factor B modulating properties, complement pathway modulating properties and modulation of the complement alternative pathway properties, e.g. as indicated in in vitro and in vivo tests as provided in the next sections and are therefore indicated for therapy.

The present invention provides methods of treating a disease or disorder associated with increased complement activity by administering to a subject in need thereof an effective amount of the compounds of Formula (I) of the invention. In certain aspects, methods are provided for the treatment of diseases associated with increased activity of the C3 amplification loop of the complement pathway. In certain embodiments, methods of treating or preventing compelment mediated diseases are provided in which the complement activation is induced by antibody-antigen interactions, by a component of an autoimmune disease, or by ischemic damage.

In a specific embodiment, the present invention provides a method of treating or preventing age-related macular degeneration (AMD) by administering to a subject in need thereof an effective amount of the compound of Formula (I) of the invention. In certain embodiments, patients who are currently asymptomatic but are at risk of developing a symptomatic macular degeneration related disorder are suitable for administration with a compound of the invention. The methods of treating or preventing AMD include, but are not limited to, methods of treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macular degeneration, diabetic retinopathy, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides methods of treating a complement related disease or disorder by administering to a subject in need thereof an effective amount of the compounds of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides methods of treating a complement related disease or disorder by administering to a subject in need thereof an effective amount of the compounds of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, anca vasculitis, cryoglobulinemia, systemic lupus, lupus erythematosus, psoriasis, multiple sclerosis, transplantation, diseases of the central nervous system such as Alzheimer's disease and other neurodegenerative conditions, atypically hemolytic uremic syndrome (aHUS), glomerulonephritis (including membrane proliferative glomerulonephritis), dense deposit disease, blistering cutaneous diseases (including bullous pemphigoid, pemphigus, and epidermolysis bullosa), ocular cicatrical pemphigoid or MPGN II.

In a specific embodiment, the present invention provides methods of treating glomerulonephritis by administering to a subject in need thereof an effective amount of a composition comprising a compound of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitant administration of a complement C5 inhibitor or C5 convertase inhibitor such as Soliris.

In a specific embodiment, the present invention provides methods of reducing the dysfunction of the immune and/or hemostatic systems associated with extracorporeal circulation by administering to a subject in need thereof an effective amount of a composition comprising an compound of the present invention. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In other embodiments, the compounds of the invention are suitable for use in the treatment of diseases and disorders associated with fatty acid metabolism, including obesity and other metabolic disorders.

In another embodiment, the compounds of the invention may be used in blood ampules, diagnostic kits and other equipment used in the collection and sampling of blood. The use of the compounds of the invention in such diagnostic kits may inhibit the ex vivo activation of the complement pathway associated with blood sampling.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by alternative complement pathway. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the complement alternative pathway, wherein the medicament is prepared for administration with another therapeutic agent. The invention also provides the use of another therapeutic agent for treating a disease or condition mediated by the complement alternative pathway, wherein the medicament is administered with a compound of formula (I).

The invention also provides a compound of formula (I) for use in a method of treating a disease or condition mediated by the complement alternative pathway, wherein the compound of formula (I) is prepared for administration with another therapeutic agent. The invention also provides another therapeutic agent for use in a method of treating a disease or condition mediated by the complement alternative pathway and/or Factor B, wherein the other therapeutic agent is prepared for administration with a compound of formula (I). The invention also provides a compound of formula (I) for use in a method of treating a disease or condition mediated by the complement alternative pathway and/or Factor B, wherein the compound of formula (I) is administered with another therapeutic agent. The invention also provides another therapeutic agent for use in a method of treating a disease or condition mediated by the complement alternative pathway and/or Factor B, wherein the other therapeutic agent is administered with a compound of formula (I).

The invention also provides the use of a compound of formula (I) for treating a disease or condition mediated by the complement alternative pathway and/or Factor B, wherein the patient has previously (e.g. within 24 hours) been treated with another therapeutic agent. The invention also provides the use of another therapeutic agent for treating a disease or condition mediated by the complement alternative pathway and/or Factor B wherein the patient has previously (e.g. within 24 hours) been treated with a compound of formula (I).

The pharmaceutical compositions can be administered alone or in combination with other molecules known to have a beneficial effect on retinal attachment or damaged retinal tissue, including molecules capable of tissue repair and regeneration and/or inhibiting inflammation. Examples of useful, cofactors include complement inhibitors (such as inhibitors of Factor D, C5a receptor and antibody or Fabs against C5, C3, properidin, factor H, and the like), anti-VEGF agents (such as an antibody or FAB against VEGF, e.g., Lucentis or Avastin), basic fibroblast growth factor (bFGF), ciliary neurotrophic factor (CNTF), axokine (a mutein of CNTF), leukemia inhibitory factor (LIF), neurotrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics. Suitable agents for combination treatment with the compounds of the invention include agents known in the art that are able to modulate the activities of complement components.

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related ocular disease as described above with a compound of the invention and an anti-angiogenic, such as anti-VEGF agent (including Lucentis and Avastin) or photodynamic therapy (such as verteporfin).

In some embodiments, the present invention provide a combination therapy for preventing and/or treating autoimmune disease as described above with a compound of the invention and a B-Cell or T-Cell modulating agent (for example cyclosporine or analogs thereof, rapamycin, RAD001 or analogs thereof, and the like). In particular, for multiple sclerosis therapy may include the combination of a compound of the invention and a second MS agent selected from fingolimod, cladribine, tysarbi, laquinimod, rebif, avonex and the like.

In one embodiment, the invention provides a method of modulating activity of the complement alternative pathway in a subject, wherein the method comprises administering to the subject a therapeutically effective amount of the compound according to the definition of formula (I). The invention further provides methods of modulating the activity of the complement alternative pathway in a subject by modulating the activity of Factor B, wherein the method comprises administering to the subject a therapeutically effective amount of the compound according to the definition of Formula (I).

In one embodiment, the invention provides a compound according to the definition of formula (I), (Ia), or any subformulae thereof, for use as a medicament.

In one embodiment, the invention provides the use of a compound according to the definition of formula (I), (Ia), or any subformulae thereof, for the treatment of a disorder or disease in a subject mediated by complement activation. In particular, the invention provides the use of a compound according to the definition of formula (I), (Ia), or any subformulae thereof, for the treatment of a disorder or disease mediated by activation of the complement alternative pathway.

In one embodiment, the invention provides the use of a compound according to the definition of formula (I), (Ia), or a subformulae thereof in the manufacture of a medicament for the treatment of a disorder or disease in a subject characterized by activation of the complement system. More particularly in the manufacture of a medicament for the treatment of a disease or disorder in a subject characterized by over activation of the complement alternative pathway.

In one embodiment, the invention provides the use of a compound according to the definition of formula (I), (Ia), or subformulae thereof for the treatment of a disorder or disease in a subject characterized by activation of the complement system. More particularly, the invention provides uses of the compounds provided herein in the treatment of a disease or disorder characterized by over activation of the complement alternative pathway or the C3 amplification loop of the alternative pathway. In certain embodiments, the use is in the treatment of a disease or disorder is selected from retinal diseases (such as age-related macular degeneration).

The present invention provides use of the compounds of the invention for treating a disease or disorder associated with increased complement activity by administering to a subject in need thereof an effective amount of the compounds of Formula (I) of the invention. In certain aspects, uses are provided for the treatment of diseases associated with increased activity of the C3 amplification loop of the complement pathway. In certain embodiments, uses of treating or preventing compelment mediated diseases are provided in which the complement activation is induced by antibody-antigen interactions, by a component of an autoimmune disease, or by ischemic damage.

In a specific embodiment, the present invention provides use of the compounds of the invention for treating or preventing age-related macular degeneration (AMD). In certain embodiments, patients who are currently asymptomatic but are at risk of developing a symptomatic macular degeneration related disorder are suitable for administration with a compound of the invention. The use in treating or preventing AMD include, but are not limited to, uses in treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macular degeneration, diabetic retinopathy, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides uses for treating a complement related disease or disorder. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides use of the compounds of the invention for treating a complement related disease or disorder, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypically hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatricial pemphigoid or MPGN II.

In a specific embodiment, the present invention provides use of the compounds of the invention for treating glomerulonephritis. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitant administration of a complement C5 inhibitor or C5 convertase inhibitor such as Soliris.

In a specific embodiment, the present invention provides use of the compounds of the invention for reducing the dysfunction of the immune and/or hemostatic systems associated with extracorporeal circulation. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In one embodiment of the present invention, there is provided (−)-2-(Hydroxy(5-methoxy-7-methyl-1H-indol-4-yl)methyl)-1H-imidazo[4,5-b]pyridine-6-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is provided (+)-2-(1-Hydroxy-1-(5-methoxy-7-methyl-1H-indol-4-yl)ethyl)-3H-imidazo[4,5-b]pyridine-6-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is provided (+2-(1-Methoxy-1-(5-methoxy-7-methyl-1H-indol-4-yl)ethyl)-3H-imidazo[4,5-b]pyridine-6-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is provided (−)-2-(2,2,2-Trifluoro-1-(5-methoxy-7-methyl-1H-indol-4-yl)-1-(methylamino)ethyl)-3H-imidazo[4,5-b]pyridine-6-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is provided (+2-(1-Amino-1-(5-methoxy-7-methyl-1H-indol-4-yl)ethyl)-3H-imidazo[4,5-b]pyridine-6-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is provided 2-(2-(5-Methoxy-7-methyl-1H-indol-4-yl)propan-2-yl)-3H-imidazo[4,5-b]pyridine-6-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is provided (±)-2-(1-(5-Cyclopropyl-7-methyl-1H-indol-4-yl)-1-hydroxyethyl)-3H-imidazo[4,5-b]pyridine-6-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is provided (±)-2-(1-Amino-1-(5-cyclopropyl-7-methyl-1H-indol-4-yl)-2,2,2-trifluoroethyl)-3H-imidazo[4,5-b]pyridine-6-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retinochorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

The following examples are intended to illustrate the invention and are not to be construed as being limitations thereon. Temperatures are given in degrees centigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Inter Alia the following in vitro tests may be used

BIOLOGICAL EXAMPLE 1

Human Complement Factor B ELISA Assay

CVF-Bb complex prepared from purified cobra venom factor (1 µM), recombinant human complement factor B (expressed in *drosophila* cells and purified using standard methods) and human complement factor D (expressed in *E. Coli*, refolded and purified using standard methods). CVF-Bb complex at 3 nM concentration was incubated with test compound at various concentrations for 1 hour at room temperature in PBS pH 7.4 containing 10 mM $MgCl_2$ and 0.05% (w/v) CHAPS. Human complement C3 substrate purified from plasma was added to a final concentration of 1 µM. After 1 hour incubation at room temperature, the enzyme reaction was stopped by addition of a cocktail of concentrated pan-protease inhibitors. The product of the reaction, C3a, was quantified by means of an enzyme-linked-immunosorbent assay. $IC_{50}$ values were calculated from percentage of inhibition of CVF-Bb activity as a function of test compound concentration.

BIOLOGICAL EXAMPLE 2

Human Complement Factor B TR-FRET Assay

BIOLOGICAL EXAMPLE 2.1

(+) or (−)-tert-Butyl 3-(3-hydroxyphenyl)piperazine-1-carboxylate

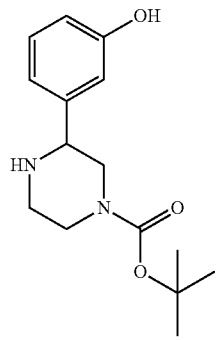 [SMILES: CC(C)(C)OC(=O)N1CCNC(c2cccc(O)c2)C1]

Resolution of the enantiomers of (±)-tert-butyl 3-(3-hydroxyphenyl)piperazine-1-carboxylate (CAS#889956-76-7) was achieved by chiral HPLC using a CHIRALPAK AD column with heptane/EtOAc/MeOH 90/5/5+0.1 diethylamine to give (+) or (−)-tert-butyl 3-(3-hydroxyphenyl)piperazine-1-carboxylate ($t_r$=9.7 min) and (−) or (−)-tert-butyl 3-(3-hydroxyphenyl)piperazine-1-carboxylate ($t_r$=15.7 min).

BIOLOGICAL EXAMPLE 2.2

(+) or (−)-tert-Butyl 3-(3-(2-(((benzyloxy)carbonyl)amino)ethoxy)phenyl)piperazine-1-carboxylate

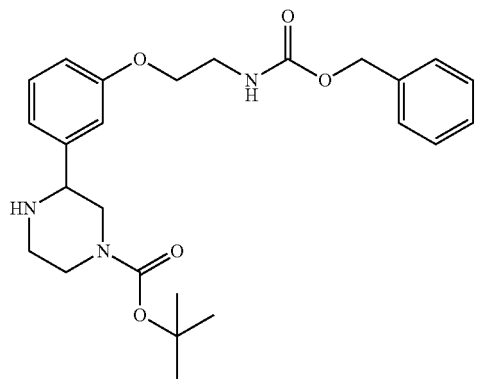 [SMILES: CC(C)(C)OC(=O)N1CCNC(c2cccc(OCCNC(=O)OCc3ccccc3)c2)C1]

(+) or (−)-tert-butyl 3-(3-hydroxyphenyl)piperazine-1-carboxylate ($t_r$=9.7 min) (Biological Example 2.1) (300 mg, 1.078 mmol) and benzyl 2-hydroxyethylcarbamate (210 mg, 1.078 mmol) were dissolved in THF (10 ml). Tributylphosphine (0.404 ml, 1.617 mmol) was added, and after cooling to 0° C., DEAD 40% in toluene (0.640 ml, 1.617 mmol) was added dropwise. The reaction was stirred for 2 h at 0° C., then overnight at rt. The reaction mixture was diluted with aqueous NaHCO$_3$. The layers were separated and the aqueous layer was extracted with AcOEt. The organic phase dried over MgSO$_4$ and concentrated in vacuum. The crude residue was purified by preparative HPLC (Macherey-Nagel Nucleosil 100-10 C18, CH$_3$CN/H$_2$O (0.1% TFA)) to give the title compound. MS (ESI+) m/z 455.2 (M+H).

BIOLOGICAL EXAMPLE 2.3

(+) or (−)-tert-Butyl 4-(4-amino-6,7-dimethoxyquinazolin-2-yl)-3-(3-(2-(((benzyloxy)carbonyl)amino)ethoxy)phenyl)piperazine-1-carboxylate

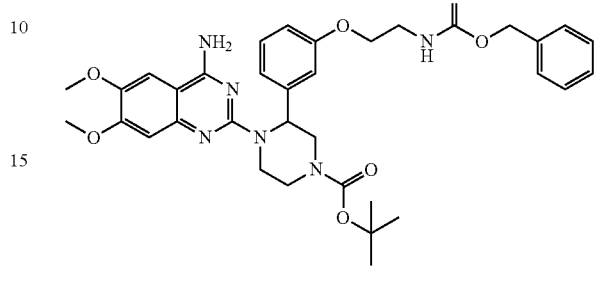

A solution of 2-chloro-6,7-dimethoxyquinazolin-4-amine (CAS#23680-84-4) (105 mg, 0.439 mmol) and (+) or (−)-tert-butyl 3-(3-(2-(((benzyloxy)carbonyl)amino)ethoxy)phenyl)piperazine-1-carboxylate (100 mg, 0.220 mmol) in isoamyl alcohol (5 ml) was stirred for 16 hr at 135° C. After evaporation, the crude was purified by preparative HPLC (Macherey-Nagel Nucleosil® 100-10 C18, CH$_3$CN/H$_2$O (0.1% TFA)) to give the title compound. MS (ESI+) m/z 659.2 (M+H).

BIOLOGICAL EXAMPLE 2.4

(+) or (−)-tert-Butyl ((1R)-3-(4-(4-amino-6,7-dimethoxyquinazolin-2-yl)-3-(3-(2-(((benzyloxy)carbonyl)amino)ethoxy)phenyl)piperazin-1-yl)-3-oxo-1-phenylpropyl)carbamate

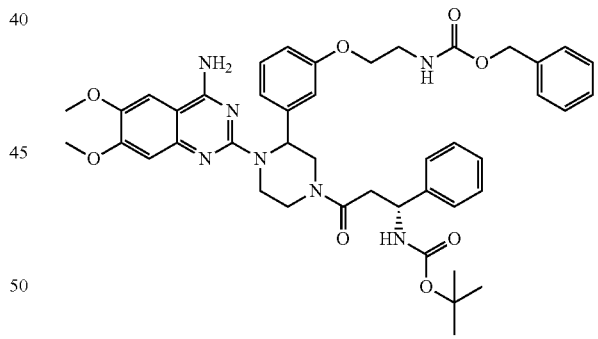

(+) or (−)-tert-Butyl 4-(4-amino-6,7-dimethoxyquinazolin-2-yl)-3-(3-(2-(((benzyloxy)carbonyl)amino)ethoxy)phenyl)piperazine-1-carboxylate (60 mg, 0.078 mmol) was dissolved in 4N HCl in dioxane (5 ml) and stirred for 1 hr at rt. The reaction mixture was evaporated. The crude residue was dissolved in DMF (3 ml), and (R)-3-((tert-butoxycarbonyl)amino)-3-phenylpropanoic acid (21.0 mg, 0.079 mmol), DIPEA (0.041 ml, 0.238 mmol) and HATU (60.2 mg, 0.158 mmol) were added. The solution was stirred for 16 hr at rt. The reaction mixture was filtrated and evaporated in vacuum. The crude residue was purified by preparative HPLC (Waters SunFire™ Prep C18 OBD, CH$_3$CN/H$_2$O (0.1% TFA)) to give the title compound. MS (ESI+) m/z 806.2 (M+H).

BIOLOGICAL EXAMPLE 2.5

(+) or (−)-2-((1E,3E,5E)-5-(1-(6-((2-(3-(1-(4-amino-6,7-dimethoxyquinazolin-2-yl)-4-((R)-3-((tert-butoxycarbonyl)amino)-3-phenylpropanoyl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium 14-1) (13.32 mg, 0.020 mmol), DIPEA (0.018 ml, 0.101 mmol) and HATU (15.40 mg, 0.040 mmol) were added. The solution stirred for 16 hr at rt. The reaction mixture evaporated in vacuum and purified by preparative HPLC (Macherey-Nagel Nucleosil® 100-10 C18, $CH_3CN/H_2O$ (0.1% TFA)) to give the title compound. MS (ESI+) m/z 656.1 (M/2).

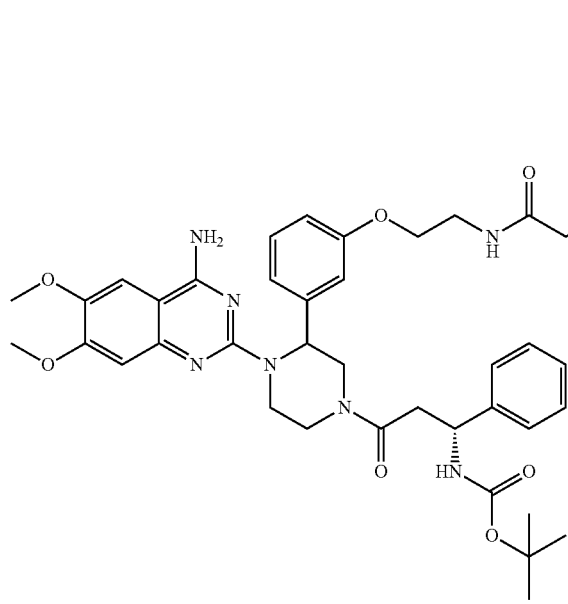

(+) or (−)-tert-Butyl ((1R)-3-(4-(4-amino-6,7-dimethoxyquinazolin-2-yl)-3-(3-(2-(((benzyloxy)carbonyl)amino)ethoxy)phenyl)piperazin-1-yl)-3-oxo-1-phenylpropyl)carbamate (17 mg, 0.021 mmol) was dissolved in EtOH (5 ml), and added Pd/C (2.24 mg, 2.109 μmol). The reaction was stirred under $H_2$ for 16 hr at room temperature. The reaction mixture was filtered and evaporated. The resulting residue was dissolved in DMF (2 ml), and 2-((1E,3E,5E)-5-(1-(6-((2,5-dioxopyrrolidin-1-yl)oxy)-6-oxohexyl)-3,3-dimethyl-5-sulfoindolin-2-ylidene)penta-1,3-dien-1-yl)-1-ethyl-3,3-dimethyl-3H-indol-1-ium-5-sulfonate (Cy-5, CAS#146368-

BIOLOGICAL EXAMPLE 2.6

(+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium

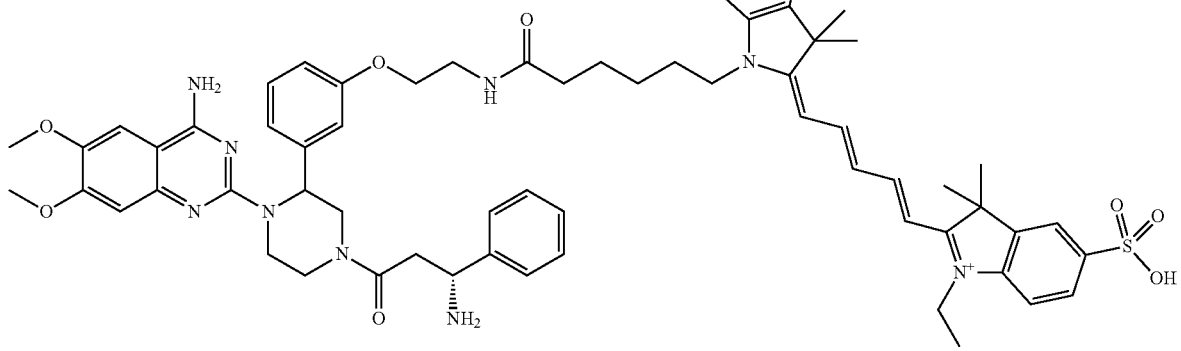

(+) or (−)-2-((1E,3E,5E)-5-(1-(6-((2-(3-(1-(4-amino-6,7-dimethoxyquinazolin-2-yl)-4-((R)-3-((tert-butoxycarbonyl)amino)-3-phenylpropanoyl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (4 mg, 3.05 μmol) was dissolved in 4N HCl in dioxane (3 ml) and stirred for 1 hr at rt. The crude mixture was purified by preparative HPLC (Waters Sunfire™ C18 OBD, CH$_3$CN/H$_2$O (0.1% TFA)) to give the title compound. Fractions were combined and evaporated to dryness. The residue was dissolved in a minimum amount of CH$_3$CN and 1M aqueous HCl solution (3 ml, 3.00 mmol) was added. Mixture was then evaporated to give the title compound as HCl salt. $^1$H NMR (HCl salt, 400 MHz, METHANOL-d$_4$) d ppm 8.30 (m, 2 H), 7.90 (s, 1 H), 7.89 (d, J=5.4 Hz, 1 H), 7.86 (d, J=5.6 Hz, 1 H), 7.72 (dd, J=8.1, 37 Hz, 1 H) , 7.55 (d, J=7.2 Hz, 1 H) , 7.37-7.47 (m, 5 H) , 7.07-7.28 (m, 4 H) , 6.86-6.95 (m, 3 H) , 6.68 (t, J=12.5 Hz, 1 H) , 6.38 (dd, J=4.5, 18.4 Hz, 1 H) , 6.31 (d, J=13.9 Hz, 1 H) , 5.95 (br. s, 1 H) , 4.76-4.84 (m, 1 H) , 4.68-4.71 (m, 1 H) , 4.46-4.57 (m, 1 H), 4.18-4.31 (m, 3 H) , 4.05-4.11 (m, 3 H) , 3.80-4.00 (m, 8 H) , 3.41-3.60 (m, 3 H) , 3.06-3.09 (m, 2 H) , 2.84 (dd, J=3.8, 22.5 Hz, 1 H) , 2.12-2.22 (m, 2 H) , 1.75-1.86 (m, 2 H) , 1.73 (s, 6 H) , 1.70 (s, 6 H) , 1.59-1.69 (m, 2 H) , 1.39 (t, J=7.3 Hz, 3 H) , 1.29-1.37 (m, 2 H). UPLC-MS (ESI+) m/z 606.1 (M/2); Instrument: Waters UPLC Acquity; column: Acquity HSS T3 1.8 μm 2.1×50 mm at 50° C., eluent A: water+0.05% HCOOH+3.75 mM ammonium acetate, B: CH$_3$CN+0.04% HCOOH, Gradient: 5 to 98% B in 1.4 min, flow: 1.0 ml/min; Retention time: 0.64 min.

BIOLOGICAL EXAMPLE 2.7

Recombinant human factor B (expressed in *drosophila* cells and purified using standard methods) labeled with biotin (10 nM), europium-labeled streptavidin (5 nM) and (+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (Biological Example 2.6, 240 nM activity against factor B when tested using the assay of Biological Example 1) (75 nM) were incubated with test compound at various concentrations up to 2 hours at room temperature in 20 mM Tris/HCl, pH 7.4, 0.005% (v/v) Tween20.

The time-gated decrease in fluorescence intensity related to the competition between labeled and unlabeled factor B ligands was recorded at both 620 nm and 665 nm, 70 μs after excitation at 337 nm using a microplate spectrofluorimeter. IC$_{50}$ values were calculated from percentage of inhibition of complement factor B-(+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (Biological Example 2.6, 240 nM activity against factor B when tested using the assay of Biological Example 1) displacement as a function of test compound concentration.

The following Examples, while representing preferred embodiments of the invention, serve to illustrate the invention without limiting its scope.

ABBREVIATIONS

Ac acetyl
AcOH acetic acid
app apparent
aq. aqueous
atm atmosphere
Boc tertiary butyl carboxy
br. broad
BuOH butanol
calcd. calculated
CHAPS 3-[(3-cholamidopropyl)dimethylammonio]-1-propanesulfonate
CVF Cobra Venom Factor
Cy5 2-((1E,3E,5E)-5-(1-(6-((2,5-dioxopyrrolidin-1-yl)oxy)-6-oxohexyl)-3,3-dimethyl-5-sulfoindolin-2-ylidene)penta-1,3-dien-1-yl)-1-ethyl-3,3-dimethyl-3H-indol-1-ium-5-sulfonate
d doublet
DBU 1,8-diazabicyclo[5.4.0]undec-7-ene
dd doublet of doublets
DCM dichloromethane
DEA diethylamine
DIBAL-H diisobutylaluminium hydride
DIPEA N,N-diisopropylethylamine
DMAP 4,4-dimethylaminopyridine
DME 1,4-dimethoxyethane
DMF N,N-dimethylformamide
Dess-Martin Periodinane Dess-Martin reagent; 1,1,1-Triacetoxy-1,1-dihydro-1,2-benziodoxol-3(1H)-one
DMSO dimethylsulfoxide
ESI electrospray ionization
EtOAc, AcOEt ethyl acetate
Et ethyl
EtOH ethanol
FCC flash column chromatography
g grams
h hour(s)
HATU 2-(1H-7-azabenzotriazol-1-yl)-1,1,3,3-tetramethyl uronium hexafluorophosphate methanaminium
HC HPLC condition
HFIP 1,1,1,3,3,3-hexafluoro-2-propanol
HPLC high performance liquid chromatography
IPA 2-propanol
IR infrared spectroscopy
L litter(s)
LDA lithium diisopropyl amide
TMP 2,2',6,6'-tetramethylpiperidine, 2,2',6,6'-tetramethylpiperidyl
M molar
MHz mega Herts
m multiplet
Me methyl
MeI iodomethane
MeOH methanol
mg milligram(s)
mm millimeter (s)
min minutes
mL milliliter(s)
mmol millimoles
MS mass spectrometry
Ms$_2$O methanesulfonyl anhydride
m/z mass to charge ratio
N normal
NMR nuclear magnetic resonance
PBS phosphate buffered saline
Pd/C palladium on carbon
Ph phenyl
ppm parts per million
PyBOP benzotriazol-1-yloxytripyrrolidinophosphonium hexafluorophosphate rac racemic
RP- reverse phase
rt room temperature
t_r retention time
s singlet
sat. saturated
SEM 2-(trimethylsilyl)ethoxymethyl
SFC Supercritical Fluid Chromatography
t triplet
TBAF tetra-n-butylammonium fluoride
TBSCl tert-butyldimethylsilyl chloride
TEA, Et$_3$N triethylamine
tert- tertiary
TFA trifluoroacetic acid
THF tetrahydrofuran
TIPS triethylsilyl
TMS trimethylsilyl
Ts p-toluenesulfonyl
TsOH p-toluenesulfonic acid
v/v volume per volume
w/v weight per volume The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

Multiple parent ion masses are reported for mass spectroscopy data when the compound of the invention contains one or more bromine atoms. Bromine exists as an approximately 1:1 molar ratio of $^{79}$Br:$^{81}$Br. Thus, a compound with a single bromine atom will exhibit two parent mass ions having a difference of 2 amu.

Following preparation methods were used for RP-HPLC.
HC-A:
Stationary phase: Waters SunFire™ Prep C18 OBD™ 5 μm, 30×100 mm
Mobile phase: gradient, water with 0.1% TFA/acetonitrile
HC-B
Stationary phase: Gemini® NX 5μ C18 110A 100×30 mm
Mobile phase: gradient, water with 0.1% (28% ammonium hydroxide)/acetonitrile

EXAMPLE 1

Intermediate 1. 3-((2-(Trimethylsilyl)ethoxy)methyl)-3H-imidazo[4,5-b]pyridine-6-carbonitrile

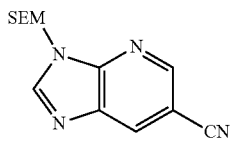 [SMILES: C[Si](C)(C)CCOCn1cnc2cc(C#N)cnc21]

To a solution of 3H-imidazo[4,5-b]pyridine-6-carbonitrile (CAS 517918-95-5, 2.5 g, 17.35 mmol) in DMF (100 ml) at 0° C., was added sodium hydride (0.832 g, 60% in oil, 20.81 mmol). The reaction was stirred at 0° C. for 20 min, then (2-(chloromethoxy)ethyl) trimethylsilane (3.33 g, 19.95 mmol) was added. The reaction was stirred at 0° C. for 15 min, then at room temperature for 30 min. The reaction mixture was cooled to 0° C. and quenched with saturated aqueous NH$_4$Cl slowly. The mixture was extracted with a mixed solvent of ethyl acetate and heptanes (1/1) three times. The combined organic layers were washed by brine and dried over Na$_2$SO$_4$, filtered and concentrated. The resulting residue was purified by FCC (ethyl acetate/heptanes=0 to 100%) to give title compound. MS (ESI+) m/z 275.1 (M+H).

EXAMPLE 2

Intermediate 2

Example 2-A

7-Methyl-1H-indol-5-ol

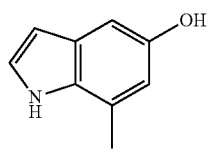

Potassium nitrosodisulfonate (46.1 g, 172 mmol) was added to a 0.1 M aqueous solution of sodium phosphate at pH=7 (1 L) at room temperature. 7-Methylindoline (CAS #: 65673-86-1) (10.4 g, 78 mmol) was dissolved in 100 mL of acetone and added to the reaction in one portion at room temperature. After 30 minutes the reaction was diluted with ethyl acetate and the organic layer was separated. The aqueous layer was then extracted with ethyl acetate. The organic layers were combined, dried over magnesium sulfate, filtered and concentrated. The resulting residue was absorbed onto silica and then purified by silica gel flash chromatography (0-50% ethyl acetate in heptanes) to provide the title compound. MS (ESI+) m/z 148.1 (M+H).

EXAMPLE 2-B 5-(Allyloxy)-7-methyl-1H-indole

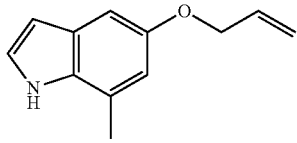

7-Methyl-1H-indol-5-ol (5.2 g, 35.3 mmol) (Example 2-A) was dissolved in toluene (221 mL) and prop-2-en-1-ol (2.42 mL, 35.3 mmol) was added followed by cyanomethylenetributyl-phosphorane (21.32 g, 88 mmol). The reaction was heated at 100° C. After 1 hour the reaction was cooled to room temperature, concentrated and purified by silica gel flash chromatography (0:100 EA:heptanes) to provide the title compound. MS (ESI+) m/z 188.1 (M+H).

EXAMPLE 2-C

4-Allyl-7-methyl-1H-indol-5-ol

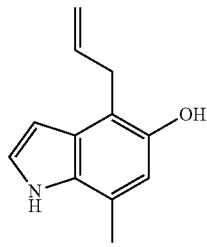

5-(Allyloxy)-7-methyl-1H-indole (2.02 g, 8.43 mmol) (Example 2-B) was heated neat at 230° C. for 6 min. The reaction was then cooled in an ice bath. The reaction was then dissolved in methanol and absorbed onto silica and then purified by silica gel flash chromatography (100% methylene chloride) to provide the title compound. MS (ESI+) m/z 188.1 (M+H).

EXAMPLE 3

Intermediate 3

EXAMPLE 3-A

4-Allyl-5-methoxy-7-methyl-1H-indole

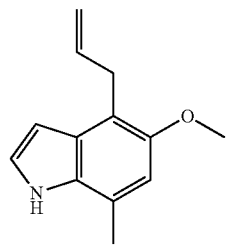

4-Allyl-7-methyl-1H-indol-5-ol (Example 2-C) (2.77 g, 14.79 mmol) was dissolved in toluene (74.0 mL) and methanol (0.599 mL, 14.79 mmol) was added followed by cyanomethylenetributylphosphorane (8.93 g, 37.0 mmol). The reaction was heated at 110° C. for 1 hour. The reaction was cooled to room temperature and then concentrated. The residue was then absorbed onto silica and purified by silica gel flash chromatography (0-50% ethyl acetate/heptanes) to provide the title compound. MS (ESI+) m/z 202.2 (M+H).

EXAMPLE 3-B tert-Butyl 4-allyl-5-methoxy-7-methyl-1H-indole-1-carboxylate

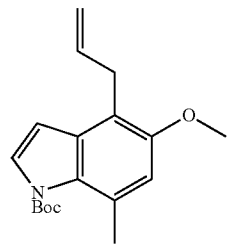 [SMILES: C=CCc1c(OC)cc(C)c2c1ccn2C(=O)OC(C)(C)C]

4-Allyl-5-methoxy-7-methyl-1H-indole (6.4 g, 31.8 mmol) (Example 3-A) was dissolved in Acetonitrile (106 mL) and then Boc$_2$O (11.07 mL, 47.7 mmol) was added followed by DMAP (0.039 g, 0.318 mmol). The reaction was then stirred at room temperature overnight. The reaction was concentrated and absorbed onto silica and then purified by silica gel flash chromatography (0-50% ethyl acetate/heptanes) to provide the title compound. MS (ESI+) m/z 302.2 (M+H).

EXAMPLE 3-C tert-Butyl 5-methoxy-7-methyl-4-(prop-1-en-1-yl)-1H-indole-1-carboxylate

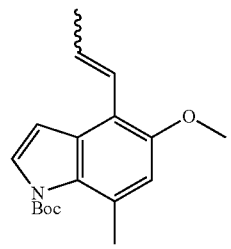

To a solution of tert-Butyl 4-allyl-5-methoxy-7-methyl-1H-indole-1-carboxylate (9.8 g, 32.5 mmol) (Example 3-B) in 1,1,1,3,3,3-hexafluoro-propanol (HFIPA) (40.6 mL) was added to palladium(II) acetate (0.073 g, 0.325 mmol) in 4 mL of HFIPA. The reaction was stirred at room temperature for 4 hours. The reaction was concentrated and absorbed onto silica and then purified by silica gel flash chromatography (0-30% ethyl acetate/heptanes) to provide the title compound. MS (ESI+) m/z 302.2 (M+H).

EXAMPLE 3-D tert-Butyl 4-formyl-5-methoxy-7-methyl-1H-indole-1-carboxylate

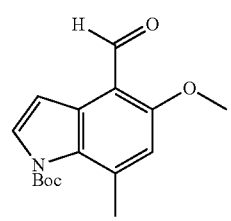 [SMILES: COc1cc(C)c2c(ccn2C(=O)OC(C)(C)C)c1C=O]

tert-Butyl 5-methoxy-7-methyl-4-(prop-1-en-1-yl)-1H-indole-1-carboxylate (0.29 g, 0.97 mmol) (Example 3-C) was dissolved in dioxane (7.27 mL) and water (2.4 mL) and 2,6-lutidine (0.23 mL, 1.94 mmol) was added followed by osmium tetroxide (0.24 mL, 0.019 mmol) and sodium periodate (0.83 g, 3.88 mmol) at 0° C. The reaction was removed from the ice bath and let stir at room temperature for 1 hour. The reaction was diluted with methylene chloride and water. The organic layer was separated, dried over sodium sulfate and then concentrated. The resulting residue was absorbed onto silica and then purified by silica gel flash chromatography (0-50% ethyl acetate/heptanes) to provide the title compound. MS (ESI+) m/z 290.1 (M+H).

EXAMPLE 4

Intermediate 4

EXAMPLE 4-A (±)-tert-Butyl 5-methoxy-7-methyl-4-(2,2,2-trifluoro-1-hydroxyethyl)-1H-indole-1-carboxylate

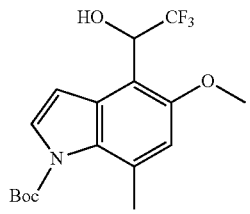 [SMILES: COc1cc(C)c2c(ccn2C(=O)OC(C)(C)C)c1C(O)C(F)(F)F]

To a solution of tert-butyl 4-formyl-5-methoxy-7-methyl-1H-indole-1-carboxylate (0.44 g, 1.52 mmol) (Example 3-D) in THF (7.24 mL), trimethyl(trifluoromethyl)silane (0.71 mL, 4.56 mmol) and then TBAF (1 M in THF, 4.56 mL, 4.56 mmol) were added at 0° C., and the reaction was stirred at room temperature. After 20 minutes the reaction mixture was diluted with aq. NH₄Cl and brine, extracted with EtOAc, and the organic extract was dried over MgSO₄, filtered and concentrated. The resulting residue was purified by flash chromatography (0-70% EtOAc in heptanes) to provide the title compound. MS (ESI+) m/z 360.1 (M+H).

EXAMPLE 4-B tert-Butyl 5-methoxy-7-methyl-4-(2,2,2-trifluoro-acetyl)-1H-indole-1-carboxylate

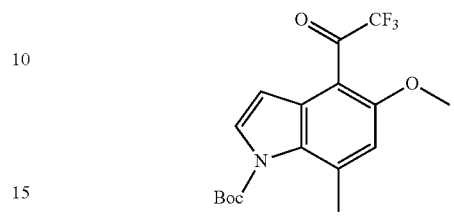

To a solution of (±)-tert-butyl 5-methoxy-7-methyl-4-(2,2,2-trifluoro-1-hydroxyethyl)-1H-indole-1-carboxylate (0.46 g, 1.28 mmol) (Example 4-A) in DCM (13 mL), Dess-Martin periodinane (0.814 g, 1.920 mmol) was added, and the reaction was stirred at room temperature. After 10 minutes the reaction mixture was quenched with aq. NaHCO₃ and aq. sodium thiosulfate. The layers were separated and the aqueous layer was extracted with DCM. The combined organic extracts were dried over MgSO₄, filtered and concentrated. The resulting residue was purified by flash chromatography (0-50% EtOAc in heptanes) to provide the title compound. MS (ESI+) m/z 358.3 (M+H).

EXAMPLE 4-C (±)-tert-Butyl 4-(1-((tert-butylsulfinyl)imino)-2,2,2-trifluoroethyl)-5-methoxy-7-methyl-1H-indole-1-carboxylate

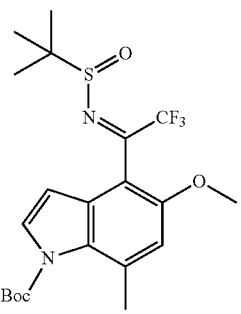 [SMILES: COc1cc(C)c2c(ccn2C(=O)OC(C)(C)C)c1/C(=N/S(=O)C(C)(C)C)C(F)(F)F]

To a solution of tert-butyl 5-methoxy-7-methyl-4-(2,2,2-trifluoroacetyl)-1H-indole-1-carboxylate (0.45 g, 1.26 mmol) (Example 4-B) and 2-methyl-2-propanesulfinamide (0.46 g, 3.78 mmol) in toluene (12.6 mL), Zr(O-t-Bu)₄ (2.52 mL, 6.30 mmol) was added at room temperature, and the reaction was heated to 100° C. After 15 minutes the reaction mixture was cooled to room temperature and diluted with EtOAc and sat. aq. brine. The resulting mixture was filtered and the layers separated. The aqueous layer was extracted with EtOAc. The combined organic extracts were dried over MgSO₄, filtered and concentrated. The resulting residue was purified by flash chromatography (0-50% EtOAc in heptanes) to provide the title compound. MS (ESI+) m/z 461.3 (M+H).

EXAMPLE 5

EXAMPLE 5-A (±)-tert-Butyl 4-(1-(6-cyano-3-((2-(trimethylsilyl)ethoxy)methyl)-3H-imidazo[4,5-b]pyridin-2-yl)-1-(1,1-dimethylethylsulfinamido)-2,2,2-trifluoroethyl)-5-methoxy-7-methyl-1H-indole-1-carboxylate

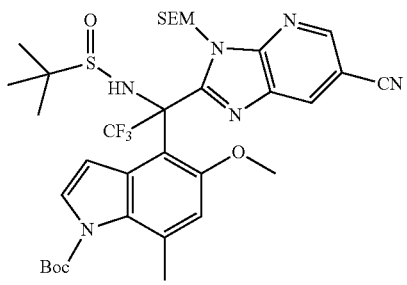 [SMILES: COc1cc(C)c2c(ccn2C(=O)OC(C)(C)C)c1C(NS(=O)C(C)(C)C)(c1nc2cc(C#N)cnc2n1COCC[Si](C)(C)C)C(F)(F)F]

To a solution of 3-((2-(trimethylsilylethoxy)methyl)-3H-imidazo[4,5-b]pyridine-6-carbonitrile (Example 1) (519 mg, 1.890 mmol) in THF (9 ml) at −78° C. under a nitrogen atmosphere, was added 2N LDA in THF (1.1 ml, 2.2 mmol). The reaction mixture was stirred at −78° C. for 15 minutes, then a solution of (±)-tert-butyl 4-(1-((tert-butylsulfinyl)imino)-2,2,2-trifluoroethyl)-5-methoxy-7-methyl-1H-indole-1-carboxylate (Example 4-C) (512 mg, 1.112 mmol) in 2 ml of THF was added. The reaction mixture was stirred at −78° C. for 15 min, then warmed to room temperature. The reaction mixture was quenched with sat. NH$_4$Cl. The reaction mixture was extracted with ethyl acetate three times. The combined organic layers were dried over Na$_2$SO$_4$. Filtration and concentration afforded the title compound without the need for further purification. MS (ESI+) m/z 735.5 (M+H).

EXAMPLE 5-B a) (±)-2-(1-Amino-2,2,2-trifluoro-1-(5-methoxy-7-methyl-1H-indol-4-yl)ethyl)-3H-imidazo[4,5-b]pyridine-6-carbonitrile

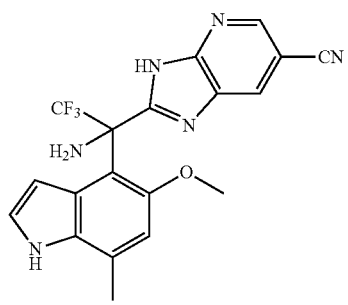 [SMILES: COc1cc(C)c2[nH]ccc2c1C(N)(c1nc2cc(C#N)cnc2[nH]1)C(F)(F)F]

A solution of 1.25N HCl in methanol (10 ml) was added to (±)-tert-butyl 4-(1-(6-cyano-3-((2-(trimethylsilylpethoxy)methyl)-3H-imidazo[4,5-b]pyridin-2-yl)-1-(1,1-dimethylethylsulfinamido)-2,2,2-trifluoroethyl)-5-methoxy-7-methyl-1H-indole-1-carboxylate (Example 5-A) (453 mg, 0.616 mmol). The reaction mixture was stirred at room temperature for 30 min. The reaction mixture was heated to 50° C. for 2 h, and then the temperature was increased to 70° C. and heated for 3.5 h. The reaction mixture was then cooled to 0° C. and basified with 7N ammonia in methanol solution (5 ml). The reaction mixture was evaporated to remove volatiles and the resulting residue was purified by FCC (methanol/DCM=0 to 7%) to give the title compound. $^1$H NMR (400 MHz, METHANOL-d$_4$) ppm 8.62 (d, J=1.64 Hz, 1H) 8.28 (d, J=1.52 Hz, 1H) 7.10 (d, J=3.28 Hz, 1H) 6.79 (s, 1H) 6.20 (d, J=2.91 Hz, 1H) 3.54 (s, 3H) 2.51 (s, 3H). HRMS calcd. for C$_{19}$H$_{15}$F$_3$N$_6$O (M+H)$^+$ 401.1338. found 401.1336.

b) (+) and (−)-2-(1-Amino-2,2,2-trifluoro-1-(5-methoxy-7-methyl-1H-indol-4-yl)ethyl)-3H-imidazo[4,5-b]pyridine-6-carbonitrile Resolution of the enantiomers (±)-2-(1-amino-2,2,2-trifluoro-1-(5-methoxy-7-methyl-1H-indol-4-yl)ethyl)-3H-imidazo[4,5-b]pyridine-6-carbonitrile was achieved by chiral SFC using a AS-H column with 35% MeOH in CO$_2$ to give (+)-2-(1-amino-2,2,2-trifluoro-1-(5-methoxy-7-methyl-1H-indol-4-yl)ethyl)-3H-imidazo[4,5-b]pyridine-6-carbonitrile (t$_r$=1.4 min) and (−)-2-(1-amino-2,2,2-trifluoro-1-(5-methoxy-7-methyl-1H-indol-4-yl)ethyl)-3H-imidazo[4,5-b]pyridine-6-carbonitrile (t$_r$=3.1 min).

EXAMPLE 6

EXAMPLE 6-A (±)-tert-Butyl 4-((6-cyano-3-((2-(trimethylsilyl)ethoxy)methyl)-3H-imidazo[4,5-b]pyridin-2-yl)(hydroxy)methyl)-5-methoxy-7-methyl-1H-indole-1-carboxylate

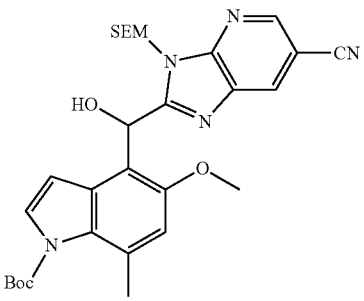 [SMILES: COc1cc(C)c2c(ccn2C(=O)OC(C)(C)C)c1C(O)c1nc2cc(C#N)cnc2n1COCC[Si](C)(C)C]

To a solution of 3-((2-(trimethylsilylpethoxy)methyl)-3H-imidazo[4,5-b]pyridine-6-carbonitrile (Example 1) (1.200 g, 4.37 mmol) in THF (30 ml) at −78° C. under nitrogen atmosphere, 2N LDA in THF (2.47 ml, 4.94 mmol) was added. The reaction mixture was stirred at −78° C. for 15 min, then the solution of tert-butyl 4-formyl-5-methoxy-7-methyl-1H-indole-1-carboxylate (Example 3-D) (1.1 g, 3.8 mmol) in 5 ml of THF was added. The reaction mixture was stirred at −78° C. for 30 min, then warmed to rt. The reaction mixture was then quenched with saturated aqueous NH$_4$Cl and extracted with ethyl acetate three times. The combined organic layers were dried over Na$_2$SO$_4$. Filtration and concentration furnished the title compound without the need for further purification. MS (ESI+) m/z 564.3 (M+H).

EXAMPLE 6-B (±)-tert-Butyl 4-((6-cyano-3H-imidazo[4,5-b]pyridin-2-yl)(hydroxy)methyl)-5-methoxy-7-methyl-1H-indole-1-carboxylate

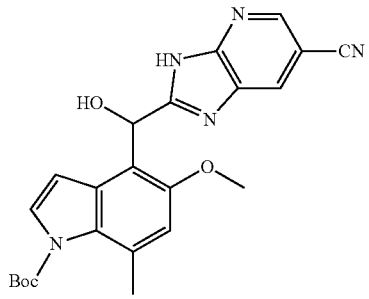 [SMILES: COc1cc(C)c2c(ccn2C(=O)OC(C)(C)C)c1C(O)c1nc2cc(C#N)cnc2[nH]1]

A solution of (±)-tert-butyl 4-((6-cyano-3-((2-(trimethylsilyl)ethoxy)methyl)-3H-imidazo[4,5-b]pyridin-2-yl)(hydroxy)methyl)-5-methoxy-7-methyl-1H-indole-1-carboxylate (Example 6-A) (320 mg, 0.568 mmol) in 1N HCl in methanol solution (4 ml) was stirred at room temperature for 16 h. The reaction mixture was then diluted with $CH_2Cl_2$. The mixture was then washed successively with water and brine, then dried over $Na_2SO_4$, filtered, and concentrated to provide the title compound. MS (ESI+) m/z 434.2 (M+H).

EXAMPLE 6-C a) (±)-2-(Hydroxy(5-methoxy-7-methyl-1H-indol-4-yl)methyl)-1H-imidazo[4,5-b]pyridine-6-carbonitrile

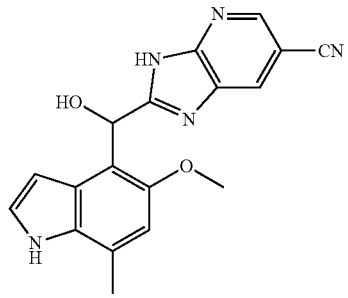 [SMILES: COc1cc(C)c2[nH]ccc2c1C(O)c1nc2cc(C#N)cnc2[nH]1]

To a suspension of tert-butyl 4-((6-cyano-3H-imidazo[4,5-b]pyridin-2-yl)(hydroxy)-methyl)-5-methoxy-7-methyl-1H-indole-1-carboxylate (Example 6-B) (246 mg, 0.568 mmol) in methanol (4 ml) was added $Cs_2CO_3$ (1 g, 3.07 mmol), and the mixture was stirred at 60° C. for 5 h. The reaction mixture was then cooled to room temperature and absorbed onto silica gel and purified by FCC (dichloromethane/2M $NH_3$ in MeOH=93/7, isocratic) to give the title compound. MS (ESI+) m/z 334.1 (M+H).

b) (+) and (−)-2-(Hydroxy(5-methoxy-7-methyl-1H-indol-4-yl)methyl)-1H-imidazo[4,5-b]pyridine-6-carbonitrile Resolution of the enantiomers (±)-2-(hydroxy(5-methoxy-7-methyl-1H-indol-4-yl)methyl)-1H-imidazo[4,5-b]pyridine-6-carbonitrile was achieved by chiral SFC using a AD-H column with 35% MeOH (plus 5 mM $NH_4OH$) in $CO_2$ to give (−)-2-(hydroxy(5-methoxy-7-methyl-1H-indol-4-yl)methyl)-1H-imidazo[4,5-b]pyridine-6-carbonitrile ($t_r$=3.1 min) and (+)-2-(hydroxy(5-methoxy-7-methyl-1H-indol-4-yl)methyl)-1H-imidazo[4,5-b]pyridine-6-carbonitrile ($t_r$=5.1 min). Each of them was further purified by acidic HPLC (ACN/water with 0.1% TFA=10% to 40%) to give corresponding TFA salt. The first eluting enantiomer ($t_r$=3.1 min) data: $^1$H NMR (400 MHz, ACETONITRILE-d3) δ 9.20 (br. s., 1H), 8.58 (d, J=1.77 Hz, 1H), 8.12 (d, J=1.70 Hz, 1H), 7.16 (t, J=2.80 Hz, 1H), 6.76 (s, 1H), 6.58 (s, 1H), 6.26-6.36 (m, 1H), 3.76 (s, 3H), 2.44 (s, 3H); HRMS calcd. for $C_{18}H_{15}N_5O_2$ (M+H)$^+$334.1304. found 334.1306. The second eluting enantiomer ($t_r$=5.1 min) data: 1H NMR (400 MHz, ACETONITRILE-d3) δ 9.20 (br. s., 1H), 8.59 (d, J=1.90 Hz, 1H), 8.09 (d, J=1.90 Hz, 1H), 7.15 (td, J=2.80, 3.00 Hz, 1H), 6.74 (s, 1H), 6.57 (s, 1H), 6.31 (dd, J=2.02, 3.03 Hz, 1H), 3.75 (s, 3H), 2.42 (s, 3H); HRMS calcd. for $C_{18}H_{16}N_5O_2$ (M+H)$^+$334.1304. found 334.1312.

EXAMPLE 7

EXAMPLE 7-A tert-Butyl 4-(6-cyano-3-((2-(trimethylsilyl)ethoxy)methyl)-3H-imidazo[4,5-b]pyridine-2-carbonyl)-5-methoxy-7-methyl-1H-indole-1-carboxylate

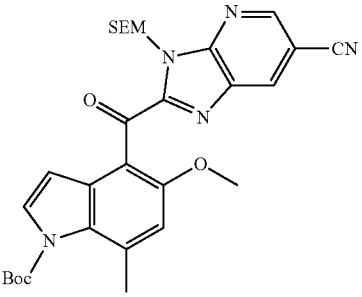 [SMILES: COc1cc(C)c2c(ccn2C(=O)OC(C)(C)C)c1C(=O)c1nc2cc(C#N)cnc2n1COCC[Si](C)(C)C]

To a solution of (±)-tert-butyl 4-((6-cyano-3-((2-(trimethylsilyl)ethoxy)methyl)-3H-imidazo[4,5-b]pyridin-2-yl)(hydroxy)methyl)-5-methoxy-7-methyl-1H-indole-1-carboxylate (Example 6-A) (2.142 g, 3.8 mmol) in DCM (50 ml) was added $MnO_2$ (6.61 g, 76 mmol). The reaction was stirred at room temperature for 16 h. The reaction mixture was then filtered through a pad of Celite®. After concentration of the filtrate, the resulting residue was purified by FCC (ethyl acetate/heptanes=0 to 30%) to give the title compound. MS (ESI+) m/z 562.2 (M+H).

EXAMPLE 7-B (±)-tert-Butyl 4-(1-(6-cyano-3-((2-(trimethylsilyl)ethoxy)methyl)-3H-imidazo[4,5-b]pyridin-2-yl)-1-hydroxyethyl)-5-methoxy-7-methyl-1H-indole-1-carboxylate

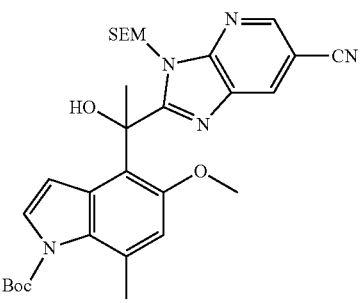

To a solution of tert-butyl 4-(6-cyano-3-((2-(trimethylsilyl)ethoxy)methyl)-3H-imidazo[4,5-b]pyridin-2-carbonyl)-5-methoxy-7-methyl-1H-indole-1-carboxylate (Example 7-A) (560 mg, 0.997 mmol) in THF (10 ml) at −40° C. was added 3N MeMgI in THF (0.665 ml, 1.994 mmol) slowly. The reaction was stirred at −40° C. for 15 min and then was quenched with saturated aqueous NH₄Cl solution and extracted with ethyl acetate three times. The combined organic layers were dried over Na₂SO₄, filtered and concentrated. The resulting residue was purified by FCC (ethyl acetate/heptanes=0 to 80%) to give the title compound. MS (ESI+) m/z 578.5 (M+H).

EXAMPLE 7-C (±)-tert-Butyl 4-(1-(6-cyano-3H-imidazo[4,5-b]pyridin-2-yl)-1-hydroxyethyl)-5-methoxy-7-methyl-1H-indole-1-carboxylate

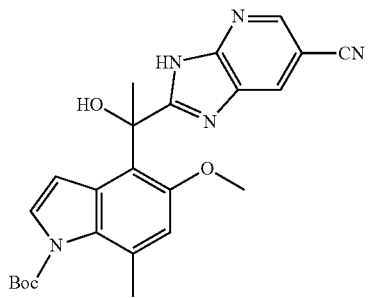 [SMILES: COc1cc(C)c2c(ccn2C(=O)OC(C)(C)C)c1C(C)(O)c1nc2cc(C#N)cnc2[nH]1]

(±)-Tert-butyl 4-(1-(6-cyano-3-((2-(trimethylsilyl)ethoxy)methyl)-3H-imidazo[4,5-b]pyridin-2-yl)-1-hydroxyethyl)-5-methoxy-7-methyl-1H-indole-1-carboxylate (Example 7-B) (490 mg, 0.848 mmol) was added to a solution of 1N TBAF in THF (42.4 mL, 42.4 mmol) followed by 0.5 ml of ethylenediamine. The reaction was heated to 60° C. for 40 min. The reaction mixture was diluted with brine and ethyl acetate. After separation, the aqueous layer was extracted with ethyl acetate three times. The combined organic layers were dried over Na₂SO₄, filtered and concentrated. The resulting residue was purified by FCC (ethyl acetate/heptanes=0 to 80%) to give the title compound. MS (ESI+) m/z 448.2 (M+H).

EXAMPLE 7-D a) (±)-2-(1-Hydroxy-1-(5-methoxy-7-methyl-1H-indol-4-yl)ethyl)-3H-imidazo[4,5-b]pyridine-6-carbonitrile

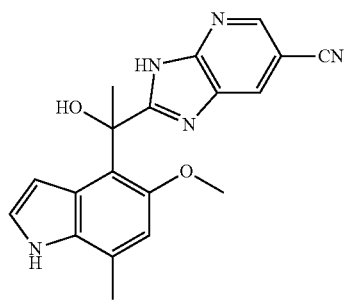

To a solution of tert-butyl 4-(1-(6-cyano-3H-imidazo[4,5-b]pyridin-2-yl)-1-hydroxyethyl)-5-methoxy-7-methyl-1H-indole-1-carboxylate (300 mg, 0.670 mmol) (Example 7-C) in methanol (7 ml) was added K₂CO₃ (927 mg, 6.70 mmol). The reaction was heated to 45° C. for 30 min. The reaction mixture was then diluted with brine and extracted with ethyl acetate three times. The combined organic layers were dried over Na₂SO₄, filtered and concentrated. The resulting residue was purified by FCC (ethyl acetate/DCM=0 to 100%) to give the title compound. ¹H NMR (400 MHz, METHANOL-d₄) δ ppm 8.61 (s, 1 H), 8.22 (br. s., 1 H), 7.21 (d, J=3.2 Hz, 1 H), 6.53-6.80 (m, 2 H), 3.42 (s, 3 H), 2.49 (s, 3 H), 2.18 (s, 3 H). HRMS calcd. for $C_{19}H_{17}N_5O_2$ (M+H)⁺ 348.1461. found 348.1457.

b) (+) and (−)-2-(1-Hydroxy-1-(5-methoxy-7-methyl-1H-indol-4-yl)ethyl)-3H-imidazo[4,5-b]pyridine-6-carbonitrile Resolution of the enantiomers (±)-2-(1-hydroxy-1-(5-methoxy-7-methyl-1H-indol-4-yl)ethyl)-3H-imidazo[4,5-b]pyridine-6-carbonitrile was achieved by chiral SFC using a IA-H column with 30% isopropanol (plus 10 mM NH₄OH) in CO₂ to give (+)-2-(1-hydroxy-1-(5-methoxy-7-methyl-1H-indol-4-yl)ethyl)-3H-imidazo[4,5-b]pyridine-6-carbonitrile (t_r=4.6 min) and (−)-2-(1-hydroxy-1-(5-methoxy-7-methyl-1H-indol-4-yl)ethyl)-3H-imidazo[4,5-b]pyridine-6-carbonitrile (t_r=8.0 min).

EXAMPLE 8

EXAMPLE 8-A (±)-tert-Butyl 4-(1-(6-cyano-3-((2-(trimethylsilyl)ethoxy)methyl)-3H-imidazo[4,5-b]pyridin-2-yl)-1-methoxyethyl)-5-methoxy-7-methyl-1H-indole-1-carboxylate

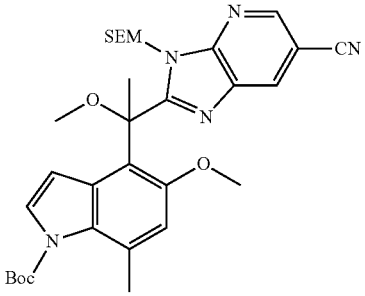 [SMILES: COc1cc(C)c2c(ccn2C(=O)OC(C)(C)C)c1C(C)(OC)c1nc2cc(C#N)cnc2n1COCC[Si](C)(C)C]

To a solution (±)-tert-butyl 4-(1-(6-cyano-3-((2-(trimethylsilyl)ethoxy)methyl)-3H-imidazo[4,5-b]pyridin-2-yl)-1-hydroxyethyl)-5-methoxy-7-methyl-1H-indole-1-carboxylate (Example 7-B) (280 mg, 0.485 mmol) in DMF (6 ml) at 0° C. was added NaH (60% suspension in oil) (38.8 mg, 0.969 mmol). The reaction was stirred at room temperature for 15 min, and then MeI (0.152 ml, 2.423 mmol) was added. The reaction was stirred at room temperature for 2 h and then was quenched with sat. NH₄Cl aqueous solution and extracted with diethyl ether three times. The combined organic layers were washed with brine and dried over Na₂SO₄. After filtration and concentration, the resulting residue was purified by FCC (ethyl acetate/heptanes=0 to 60%) to give the title compound. MS (ESI+) m/z 592.2 (M+H).

EXAMPLE 8-B a) (±)-2-(1-Methoxy-1-(5-methoxy-7-methyl-1H-indol-4-yl)ethyl)-3H-imidazo[4,5-b]pyridine-6-carbonitrile

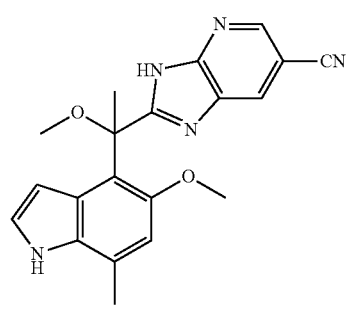 [SMILES: COc1cc(C)c2[nH]ccc2c1C(C)(OC)c1nc2cc(C#N)cnc2[nH]1]

(±)-Tert-butyl 4-(1-(6-cyano-3-((2-(trimethylsilyl)ethoxy)methyl)-3H-imidazo[4,5-b]pyridin-2-yl)-1-methoxyethyl)-5-methoxy-7-methyl-1H-indole-1-carboxylate (Example 8-A) (206 mg, 0.348 mmol) and 1N TBAF in THF (10 ml, 10.00 mmol) were mixed and heated to 65° C. for 48 h. The reaction mixture was cooled to room temperature and diluted with ethyl acetate and water. After separation of the layers, the aqueous layer was extracted with ethyl acetate three times. The combined organic layers were dried over Na₂SO₄. After filtration and concentration, the resulting residue was purified by FCC (ethyl acetate/DCM=0 to 100%) to give the title compound. ¹H NMR (400 MHz, DMSO-d₆) δ ppm 13.14 (br. s., 1 H), 10.89 (br. s., 1 H), 8.34 (br. s., 1 H), 7.26 (t, J=2.8 Hz, 1 H), 6.72 (dd, J=3.0, 2.0 Hz, 1 H), 6.66 (s, 1 H), 3.20 (s, 3 H), 3.07 (s, 3 H), 2.44 (s, 3 H), 2.01 (s, 3 H). HRMS calcd. for C₂₀H₁₉N₅O₂ (M+H)⁺ 362.1610. found 362.1608.

b) (+) and (−)-2-(1-Methoxy-1-(5-methoxy-7-methyl-1H-indol-4-yl)ethyl)-3H-imidazo[4,5-b]pyridine-6-carbonitrile Resolution of the enantiomers (±)-2-(1-methoxy-1-(5-methoxy-7-methyl-1H-indol-4-yl)ethyl)-3H-imidazo[4,5-b]pyridine-6-carbonitrile was achieved by chiral SFC using a Chiralpak® IB column with MeOH (plus 5 mM NH₄OH) gradient from 25% to 55% in CO₂ to give (+)-2-(1-methoxy-1-(5-methoxy-7-methyl-1H-indol-4-yl)ethyl)-3H-imidazo[4,5-b]pyridine-6-carbonitrile (t₍r₎=3.18 min) and (−)-2-(1-methoxy-1-(5-methoxy-7-methyl-1H-indol-4-yl)ethyl)-3H-imidazo[4,5-b]pyridine-6-carbonitrile (t₍r₎=6.25 min).

EXAMPLE 9

EXAMPLE 9-A (±)-tert-Butyl 4-(1-(6-cyano-3-((2-(trimethylsilyl)ethoxy)methyl)-3H-imidazo[4,5-b]pyridin-2-yl)-2,2,2-trifluoro-1-hydroxyethyl)-5-methoxy-7-methyl-1H-indole-1-carboxylate

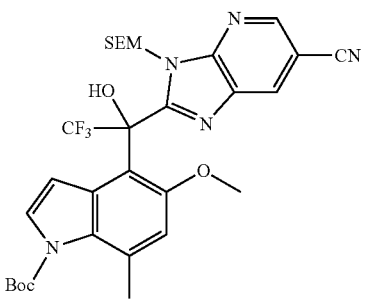 [SMILES: COc1cc(C)c2c(ccn2C(=O)OC(C)(C)C)c1C(O)(c1nc2cc(C#N)cnc2n1COCC[Si](C)(C)C)C(F)(F)F]

To a solution of (±)-tert-butyl 4-(6-cyano-3-((2-(trimethylsilyl)ethoxy)methyl)-3H-imidazo[4,5-b]pyridine-2-carbonyl)-5-methoxy-7-methyl-1H-indole-1-carboxylate (Example 7-A) (500 mg, 0.890 mmol) in THF (10 ml) at 0° C., was added CsF (13.52 mg, 0.089 mmol) followed by trimethyl-(trifluoromethyl)silane (0.417 ml, 2.67 mmol). The reaction was stirred at 0° C. for 15 minutes, then at rt for 30 minutes. Then a 1N solution of TBAF in THF (2 mL) was added and the reaction was stirred for an additional 15 minutes. The reaction mixture was then quenched with sat. aqueous solution of NaHCO₃ and extracted with ethyl acetate three times. The combined organic layers were washed with brine and dried over Na₂SO₄. After filtration and concentration, the resulting residue was purified by FCC (ethyl acetate/heptanes=0 to 30%) to give the title compound. MS (ESI+) m/z 632.3 (M+H).

EXAMPLE 9-B (±)-tert-Butyl 4-(1-(6-cyano-3H-imidazo[4,5-b]pyridin-2-yl)-2,2,2-trifluoro-1-hydroxyethyl)-5-methoxy-7-methyl-1H-indole-1-carboxylate

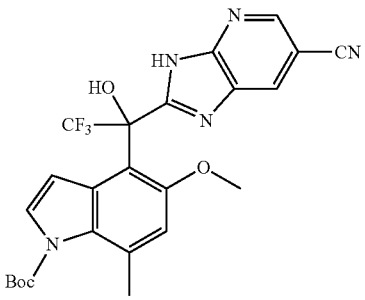 [SMILES: COc1cc(C)c2c(ccn2C(=O)OC(C)(C)C)c1C(O)(c1nc2cc(C#N)cnc2[nH]1)C(F)(F)F]

A 1.25M solution of HCl in methanol (15 mL, 18.75 mmol) was added to (±)-tert-butyl 4-(1-(6-cyano-3-((2-(trimethylsilyl)ethoxy)methyl)-3H-imidazo[4,5-b]pyridin-2-yl)-2,2,2-trifluoro-1-hydroxyethyl)-5-methoxy-7-methyl-1H-indole-1-carboxylate (Example 9-A) (0.562 g, 0.89 mmol). The reaction was stirred at 40° C. for 1.5 h. The reaction mixture then was cooled to 0° C. and diluted with water and neutralized by slow addition of solid NaHCO$_3$. The organics product were extracted with ethyl acetate three times. The combined organic layers were washed with brine and dried over Na$_2$SO$_4$. After filtration and concentration, the resulting residue was purified by FCC (ethyl acetate/ heptanes=0 to 50%) to give the title compound. MS (ESI+) m/z 502.1 (M+H).

EXAMPLE 9-C (±)-tert-Butyl 4-(1-(6-cyano-3H-imidazo[4,5-b]pyridin-2-yl)-2,2,2-trifluoro-1-(methylamino)ethyl)-5-methoxy-7-methyl-1H-indole-1-carboxylate

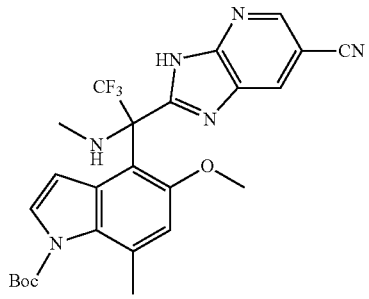 [SMILES: CNC(c1nc2cc(C#N)cnc2[nH]1)(c1c(OC)cc(C)c2c1ccn2C(=O)OC(C)(C)C)C(F)(F)F]

To a solution of (±)-tert-butyl 4-(1-(6-cyano-3H-imidazo[4,5-b]pyridin-2-yl)-2,2,2-trifluoro-1-hydroxyethyl)-5-methoxy-7-methyl-1H-indole-1-carboxylate (Example 9-B) (320 mg, 0.638 mmol) in CHCl$_3$ (10 ml) was added one drop (~10 µL) of DMF. Then thionyl chloride (466 µL, 6.38 mmol) was added. The reaction was heated to 75° C. for 30 min, and then cooled to 0° C. A 33% solution of methylamine in ethanol (5 ml) was then added very carefully and slowly to the reaction mixture. After addition, the reaction was stirred at room temperature for 15 min and diluted with ethyl acetate and brine. After separation of the layers, the aqueous layer was extracted with ethyl acetate three times. The combined organic layers were dried over Na$_2$SO$_4$. Filtration and concentration furnished the title compound without the need for further purification. MS (ESI+) m/z 515.0 (M+H).

EXAMPLE 9-D a) (±)-2-(2,2,2-Trifluoro-1-(5-methoxy-7-methyl-1H-indol-4-yl)-1-(methylamino)ethyl)-3H-imidazo[4,5-b]pyridine-6-carbonitrile

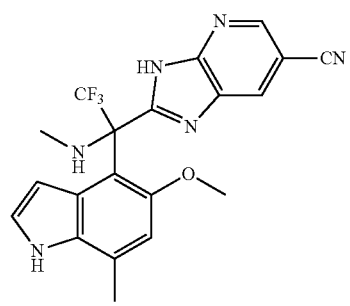 [SMILES: CNC(c1nc2cc(C#N)cnc2[nH]1)(c1c(OC)cc(C)c2[nH]ccc12)C(F)(F)F]

To a solution (±)-tert-butyl 4-(1-(6-cyano-3H-imidazo[4,5-b]pyridin-2-yl)-2,2,2-trifluoro-1-(methylamino)ethyl)-5-methoxy-7-methyl-1H-indole-1-carboxylate (Example 9-C) in methanol (5 ml) was added K$_2$CO$_3$ (403 mg, 2.92 mmol). The reaction was heated to 40° C. for 45 minutes. The reaction mixture was diluted with brine and ethyl acetate. After separation of the layers, the aqueous layer was extracted with ethyl acetate three times.

The combined organic layers were dried over Na$_2$SO$_4$. After filtration and concentration, the resulting residue was purified by FCC (ethyl acetate/heptane=0 to 100%) to give the title compound. $^1$H NMR (400 MHz, METHANOL-d$_4$) δ ppm 8.67 (br. s., 1 H) 8.39 (br. s., 1 H) 7.18 (d, J=3.28 Hz, 1 H) 6.74 (s, 1 H) 6.64 (d, J=2.40 Hz, 1 H) 3.34 (s, 3H) 2.50 (s, 3 H) 2.23 (s, 3 H). HRMS calcd. for C$_{20}$H$_{17}$F$_3$N$_6$O (M+H)$^+$ 415.1494. found 415.1485.

b) (+) and (−)-2-(2,2,2-Trifluoro-1-(5-methoxy-7-methyl-1H-indol-4-yl)-1-(methylamino)ethyl)-3H-imidazo[4,5-b]pyridine-6-carbonitrile Resolution of the enantiomers (±)-2-(2,2,2-trifluoro-1-(5-methoxy-7-methyl-1H-indol-4-yl)-1-(methylamino)ethyl)-3H-imidazo[4,5-b]pyridine-6-carbonitrile was achieved by chiral SFC using a IA-H column with 30% MeOH (plus 5 mM NH$_4$OH) in CO$_2$ to give (+)-2-(2,2,2-trifluoro-1-(5-methoxy-7-methyl-1H-indol-4-yl)-1-(methylamino)ethyl)-3H-imidazo[4,5-b]pyridine-6-carbonitrile (t$_r$=1.9 min) and (−)-2-(2,2,2-trifluoro-1-(5-methoxy-7-methyl-1H-indol-4-yl)-1-(methylamino)ethyl)-3H-imidazo[4,5-b]pyridine-6-carbonitrile (t$_r$=3.8 min).

EXAMPLE 10

EXAMPLE 10-A (±)-tert-Butyl 4-(1-(6-cyano-3-((2-(trimethylsilyl) ethoxy)methyl)-3H-imidazo[4,5-b]pyridin-2-yl)-1-(2-(trimethylsilyl)ethylsulfonamido)ethyl)-5-methoxy-7-methyl-1H-indole-1-carboxylate

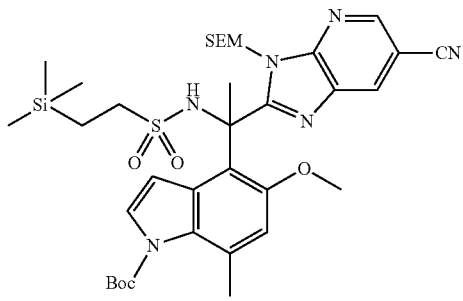 [SMILES: COc1cc(C)c2c(ccn2C(=O)OC(C)(C)C)c1C(C)(NS(=O)(=O)CC[Si](C)(C)C)c1nc2cc(C#N)cnc2n1COCC[Si](C)(C)C]

A 0.5 N stock solution of Zr(O-t-Bu)$_4$ in toluene was initially prepared. To a mixture of tert-butyl 4-(6-cyano-3-((2-(trimethylsilyl)ethoxy)methyl)-3H-imidazo[4,5-b]pyridine-2-carbonyl)-5-methoxy-7-methyl-1H-indole-1-carboxylate (Example 7-A) (820 mg, 1.460 mmol) and 2-(trimethylsilyl)ethanesulfonamide (397 mg, 2.190 mmol) under nitrogen, was added the 0.5 N Zr(O-t-Bu)$_4$ toluene stock solution (6.6 mL, 3.28 mmol). The reaction was stirred at 100° C. for 3 h. The reaction mixture was then cooled to room temperature. Additional 2-(trimethylsilyl)ethanesulfonamide (264 mg, 1.46 mmol) was then added, followed by the additional 0.5 N Zr(O-t-Bu)₄ toluene stock solution (4.4 mL, 2.190 mmol). The reaction was stirred and heated at 100° C. for an additional 2 h. Then the reaction mixture was cooled to −40° C. and a 3 M solution of MeMgI in THF (3.0 mL, 9.0 mmol) was added dropwise very slowly via syringe. After the addition was complete, the reaction was quenched via successive slow addition of methanol, and 1 N HCl. The reaction mixture was then diluted with DCM and water and brought to pH ~7 by addition of solid NaHCO₃ solid. Celite® was then added and the mixture stirred for 30 minutes, at which time the heterogeneous mixture was filtered, through a Celite® pad, which was washed with DCM. The filtrate separation was portioned and the aqueous layer was extracted with DCM twice. The combined organic layers were dried over Na₂SO₄. After filtration and concentration, the resulting residue was purified by FCC ((30% ethyl acetate in DCM)/heptanes=0 to 100%) to give the title compound. MS (ESI+) m/z 741.6 (M+H).

EXAMPLE 10B a) (±)-2-(1-Amino-1-(5-methoxy-7-methyl-1H-indol-4-yl)ethyl)-3H-imidazo[4,5-b]pyridine-6-carbonitrile

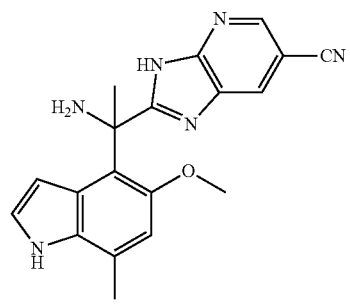 [SMILES: COc1cc(C)c2[nH]ccc2c1C(C)(N)c1nc2cc(C#N)cnc2[nH]1]

A 1 N solution of TBAF in THF (3.5 mL, 3.50 mmol) was added to (±)-tert-butyl 4-(1-(6-cyano-3-((2-(trimethylsilylpethoxy)methyl)-3H-imidazo[4,5-b]pyridin-2-yl)-1-(2-(trimethylsilyl)ethylsulfonamido)ethyl)-5-methoxy-7-methyl-1H-indole-1-carboxylate (Example 10-A) and the mixture was heated to reflux for 48 h. The reaction mixture was then cooled to room temperature and diluted with water and ethyl acetate. After separation, the aqueous layer was extracted with ethyl acetate three times. The combined organic layers were dried over Na₂SO₄. After filtration and concentration, the resulting residue was purified by FCC (ethyl acetate/heptanes=0 to 100%) and further purified by acidic HPLC (acetonitrile/0.1% TFA in water=20% to 50%) to give the title compound as a TFA salt. ¹H NMR (400 MHz, METHANOL-d₄) δ ppm 8.70 (d, J=1.8 Hz, 1 H), 8.31 (br. s., 1 H), 7.38 (d, J=3.3 Hz, 1 H), 6.87 (s, 1 H), 6.48 (d, J=3.3 Hz, 1 H), 3.53 (s, 3 H), 2.57 (s, 3 H), 2.48 (s, 3 H). MS (ESI+) m/z 347.2 (M+H). HRMS calcd. for C₁₉H₁₈N₆O (M-NH₂)⁺ 330.1355. found 330.1357.

b) (+) and (−)-2-(1-Amino-1-(5-methoxy-7-methyl-1H-indol-4-yl)ethyl)-3H-imidazo[4,5-b]pyridine-6-carbonitrile Resolution of the enantiomers (±)-2-(1-amino-1-(5-methoxy-7-methyl-1H-indol-4-yl)ethyl)-3H-imidazo[4,5-b]pyridine-6-carbonitrile was achieved by chiral SFC using a AS-H column with 35% isopropanol (plus 5 mM NH₄OH) in CO₂ to give (−)-2-(1-amino-1-(5-methoxy-7-methyl-1H-indol-4-yl)ethyl)-3H-imidazo[4,5-b]pyridine-6-carbonitrile (t_r=2.0 min) give (+)-2-(1-amino-1-(5-methoxy-7-methyl-1H-indol-4-yl)ethyl)-3H-imidazo[4,5-b]pyridine-6-carbonitrile (t_r=3.8 min).

EXAMPLE 11

EXAMPLE 11A (±)-tert-Butyl 4-(1-(6-cyano-3-((2-(trimethylsilyl)ethoxy)methyl)-3H-imidazo[4,5-b]pyridin-2-yl)-1-(N-methyl-2-(trimethylsilyl)ethylsulfonamido)ethyl)-5-methoxy-7-methyl-1H-indole-1-carboxylate

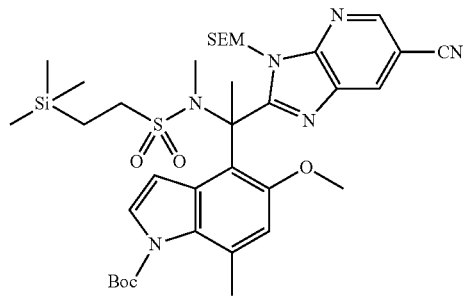 [SMILES: COc1cc(C)c2c(ccn2C(=O)OC(C)(C)C)c1C(C)(c1nc2cc(C#N)cnc2n1COCC[Si](C)(C)C)N(C)S(=O)(=O)CC[Si](C)(C)C]

To a solution of (±)-tert-butyl 4-(1-(6-cyano-3-((2-(trimethylsilyl)ethoxy)methyl)-3H-imidazo[4,5-b]pyridin-2-yl)-1-(2-(trimethylsilyl)ethylsulfonamido)ethyl)-5-methoxy-7-methyl-1H-indole-1-carboxylate (Example 10-A) (420 mg, 0.567 mmol) in acetone (15 ml), was added K₂CO₃ (783 mg, 5.67 mmol) followed by MeI (0.709 ml, 11.34 mmol). The reaction was stirred and heated to 65° C. for 16 h. The reaction mixture was then brought to room temperature, diluted with water and extracted with ethyl acetate three times. The combined organic layers were dried over Na₂SO₄. After filtration and concentration, the resulting residue was purified by FCC ((30% ethyl acetate in DCM)/heptane=0 to 100%) to give the title compound. MS (ESI+) m/z 755.3 (M+H).

EXAMPLE 11B a) (±)-2-(1-(5-Methoxy-7-methyl-1H-indol-4-yl)-1-(methylamino)ethyl)-3H-imidazo[4,5-b]pyridine-6-carbonitrile

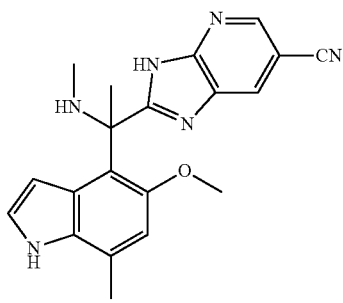 [SMILES: CNC(C)(c1nc2cc(C#N)cnc2[nH]1)c1c(OC)cc(C)c2[nH]ccc12]

(±)-Tert-Butyl 4-(1-(6-cyano-3-((2-(trimethylsilyl)ethoxy)methyl)-3H-imidazo[4,5-b]pyridin-2-yl)-1-(N-methyl-2-(trimethylsilyl)ethylsulfonamido)ethyl)-5-methoxy-7-methyl-1H-indole-1-carboxylate (Example 11-A) (380 mg, 0.503 mmol) and a 1N solution of TBAF in THF (10 ml, 10.00 mmol) were mixed and heated to 75° C. for 16 h. The reaction mixture was cooled to room temperature and diluted with ethyl acetate and water. The resulting layers were separated and aqueous layer was extracted with ethyl acetate three times. The combined organic layers were dried over Na$_2$SO$_4$. After filtration and concentration, the resulting residue was purified by FCC (ethyl acetate/DCM=0 to 100%) to give the title compound. $^1$H NMR (400 MHz, METHANOL-d$_4$) δ ppm 8.53 (d, J=1.9 Hz, 1 H), 8.14 (d, J=2.0 Hz, 1 H), 7.15 (d, J=3.3 Hz, 1 H), 6.76 (s, 1 H), 6.18 (d, J=3.3 Hz, 1 H), 3.46 (s, 3 H), 2.49 (s, 3 H), 2.32 (s, 3 H), 2.18 (s, 3 H). HRMS calcd. for C$_{20}$H$_{20}$N$_6$O (M+H)$^+$ 361.1777. found 361.1778.

b) (+) and (−)-2-(1-(5-Methoxy-7-methyl-1H-indol-4-yl)-1-(methylamino)ethyl)-3H-imidazo[4,5-b]pyridine-6-carbonitrile Resolution of the enantiomers (±)-2-(1-(5-methoxy-7-methyl-1H-indol-4-yl)-1-(methylamino)ethyl)-3H-imidazo[4,5-b]pyridine-6-carbonitrile was achieved by chiral SFC using a OD-H column with 15% ethanol (plus 0.2% diethylamine) in CO$_2$ to give (−)-2-(1-(5-methoxy-7-methyl-1H-indol-4-yl)-1-(methylamino)ethyl)-3H-imidazo[4,5-b]pyridine-6-carbonitrile (t$_r$=7.1 min) and (+)-2-(1-(5-methoxy-7-methyl-1H-indol-4-yl)-1-(methylamino)ethyl)-3H-imidazo[4,5-b]pyridine-6-carbonitrile (t$_r$=9.2 min).

EXAMPLE 12

EXAMPLE 12-A 2-(5-Methoxy-7-methyl-1H-indole-4-carbonyl)-3-((2-(trimethylsilyl)ethoxy)methyl)-3H-imidazo[4,5-b]pyridine-6-carbonitrile

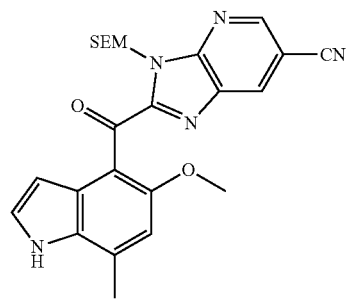 [SMILES: COc1cc(C)c2[nH]ccc2c1C(=O)c1nc2cc(C#N)cnc2n1COCC[Si](C)(C)C]

To a solution of tert-butyl 4-(6-cyano-3-((2-(trimethylsilyl)ethoxy)methyl)-3H-imidazo[4,5-b]pyridine-2-carbonyl)-5-methoxy-7-methyl-1H-indole-1-carboxylate (Example 7-A) (430 mg, 0.766 mmol) in isopropanol (10 ml) was added K$_2$CO$_3$ (1058 mg, 7.66 mmol). The reaction was heated to 65° C. for 2 h. The reaction mixture was then brought to room temperature and diluted with water and extracted with ethyl acetate twice. The combined organic layers were dried over Na$_2$SO$_4$. After filtration and concentration, the resulting residue afforded the title compound without the need for further purification. MS (ESI+) m/z 462.2 (M+H).

EXAMPLE 12B 2-(5-Methoxy-7-methyl-1-tosyl-1H-indole-4-carbonyl)-3-((2-(trimethylsilyl)ethoxy)methyl)-3H-imidazo[4,5-b]pyridine-6-carbonitrile

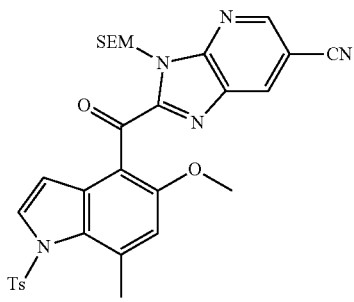 [SMILES: COc1cc(C)c2c(ccn2S(=O)(=O)c2ccc(C)cc2)c1C(=O)c1nc2cc(C#N)cnc2n1COCC[Si](C)(C)C]

To a solution of 2-(5-methoxy-7-methyl-1H-indole-4-carbonyl)-3-((2-(trimethylsilyl) ethoxy)methyl)-3H-imidazo[4,5-b]pyridine-6-carbonitrile (Example 12-A) (270 mg, 0.585 mmol) in DMF (5 ml) at 0° C. was added NaH (60% suspension in oil) (46.8 mg, 1.170 mmol). The reaction was stirred at 0° C. for 15 min and then placed at room temperature for 15 min, then p-toluenesulfonyl chloride (167 mg, 0.877 mmol) was added and the mixture stirred for 1 h. The mixture was then quenched by the addition of an aqueous solution of 28% NH$_4$OH (3 ml) and further diluted with 10 ml of water. The reaction mixture was extracted with mixed solvent (ethyl acetate/heptanes=1/1) three times. The combined organic layers were washed with brine and dried over Na$_2$SO$_4$. After filtration and concentration, the resulting residue was purified by FCC (ethyl acetate/DCM=0 to 60%) to give the title compound. $^1$H NMR (400 MHz, DICHLOROMETHANE-d$_2$) δ ppm 8.84 (d, J=1.89 Hz, 1 H) 8.39 (d, J=1.89 Hz, 1 H) 7.92 (d, J=3.79 Hz, 1 H) 7.31 (d, J=8.08 Hz, 2 H) 7.57 (d, J=8.34 Hz, 2 H) 7.10 (d, J=3.79 Hz, 1 H) 6.71 (s, 1 H) 5.87 (s, 2 H) 3.53-3.60 (m, 2 H) 3.47 (s, 3 H) 2.63 (s, 3 H) 2.39 (s, 3 H) 0.86-0.94 (m, 2 H) −0.07-0.02 (s, 9H).

EXAMPLE 12-C 2-(2-(5-Methoxy-7-methyl-1-tosyl-1H-indol-4-yl)propan-2-yl)-3H-imidazo[4,5-b]pyridine-6-carbonitrile

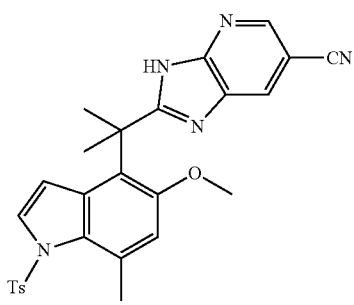 [SMILES: COc1cc(C)c2c(ccn2S(=O)(=O)c2ccc(C)cc2)c1C(C)(C)c1nc2cc(C#N)cnc2[nH]1]

A 100 ml round-bottom flask was charged with 1N TiCl4 in DCM (1.46 mL, 1.462 mmol) and DCM (10 ml) and placed at 0° C. A 1 N heptane solution of Zn(CH₃)₂ (1.46 mL, 1.462 mmol) was then added. The reaction was then placed at room temperature and stirred for 15 minutes, then re-cooled to −40° C. and then a solution of 2-(5-methoxy-7-methyl-1-tosyl-1H-indole-4-carbonyl)-3-((2-(trimethylsilyl)ethoxy)methyl)-3H-imidazo[4,5-b]pyridine-6-carbonitrile (Example 12-B) (150 mg, 0.244 mmol) in DCM (3 mL) was added. The reaction mixture was stirred at −40° C. for 15 min, then was slowly warmed to room temperature. The reaction was stirred at room temperature for 16 h, and then was quenched with water and extracted with ethyl acetate three times. The combined organic layers were dried over MgSO₄. After filtration and concentration, the resulting residue was purified by FCC (EtOAc/heptanes=0 to 80%) to give the title compound. MS (ESI+) m/z 500.4 (M+H).

EXAMPLE 12-D 2-(2-(5-Methoxy-7-methyl-1H-indol-4-yl)propan-2-yl)-3H-imidazo[4,5-b]pyridine-6-carbonitrile

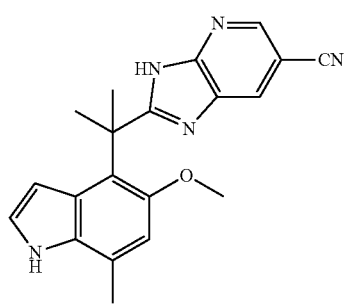 [SMILES: COc1cc(C)c2[nH]ccc2c1C(C)(C)c1nc2cc(C#N)cnc2[nH]1]

A microwave vial was charged with 2-(2-(5-methoxy-7-methyl-1-tosyl-1H-indol-4-yl)propan-2-yl)-3H-imidazo[4,5-b]pyridine-6-carbonitrile (Example 12-C) (22 mg, 0.044 mmol), potassium hydroxide (49.4 mg, 0.881 mmol), 3-methylbutan-1-amine (154 mg, 1.761 mmol) and MeOH (2 ml). The reaction mixture was heated under microwave irradiation at 100° C. for 2 h and at 110° C. for an additional 1.5 hr. The reaction mixture was then cooled to room temperature and diluted with water and acidified by 1N aqueous solution of hydrochloride and then neutralized by the addition of solid NaHCO₃. The mixture was extracted with ethyl acetate three times. The combined organic layers were dried over Na₂SO₄. After filtration and concentration, the resulting residue was purified by FCC (ethyl acetate/DCM=0 to 100%) to give the title compound. ¹H NMR (400 MHz, METHANOL-d₄) δ ppm 8.65 (d, J=1.8 Hz, 1 H), 8.19 (d, J=1.8 Hz, 1 H), 7.23 (d, J=3.3 Hz, 1 H), 6.72 (s, 1 H), 6.51 (d, J=3.3 Hz, 1 H), 3.38 (s, 3 H), 2.49 (s, 3 H), 2.04 (s, 6 H). HRMS calcd. for C₂₀H₁₉N₅O (M+H)⁺ 346.1668. found 346.1668.

EXAMPLE 13

Intermediate 5

EXAMPLE 13-A

5-Bromo-7-methyl-1H-indole-4-carbonitrile

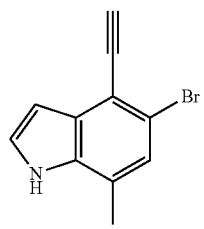

To a suspension of 1 M vinylmagnesium bromide in THF (249 ml, 249 mmol) was added dropwise 2-bromo-4-methyl-5-nitro-benzonitrile (CAS#1202858-65-8, 15 g, 62.2 mmol) in THF (100 ml) below −20° C. After completion of the addition, the mixture was placed at room temperature and stirred at for 1.5 h. The reaction mixture was then cooled to below −20° C. and quenched with MeOH while maintaining the internal reaction temperature below 0° C. To the mixture was added Celite®, and 5% aq. NaHCO₃ (50 mL). The mixture was diluted with CH₂Cl₂, and filtered through a SiO₂ pad. The SiO₂ cake was washed with 1:1 mixture of CH₂Cl₂/EtOAc. The filtrate was concentrated to give the title compound, which was used in the next reaction without the need for further purification. MS (ESI+) m/z 235.0, 237.0 (M+H).

EXAMPLE 13-B

5-Bromo-7-methyl-1-tosyl-1H-indole-4-carbonitrile

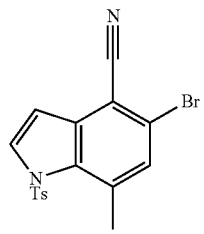 [SMILES: Cc1ccc(S(=O)(=O)n2ccc3c(C#N)c(Br)cc(C)c32)cc1]

To a suspension of 5-bromo-7-methyl-1H-indole-4-carbonitrile (Example 13-A) (11.99 g, 51 mmol), TsCl (14.58 g, 77 mmol), and triethylbenzylammonium chloride (1.162 g, 5.10 mmol) in CH₂Cl₂ (300 ml) was added NaOH (3.06 g, 77 mmol), and then the mixture was stirred at room temperature for 19 h. The reaction mixture was quenched with H₂O, and the mixture was vigorously stirred for 1 h. The mixture was further diluted with CH₂Cl₂ and the mixture was successively washed with H₂O and brine, and the organic layer then dried over Na₂SO₄, filtered, and concentrated. The resulting residue was triturated with MeOH and the solid was collected by filtration to afford the title compound which was used in the next reaction without the need for further purification. MS (ESI+) m/z 387.0, 389.0 (M−H).

EXAMPLE 14

EXAMPLE 14-A

5-Ethyl-7-methyl-1-tosyl-1H-indole-4-carbonitrile

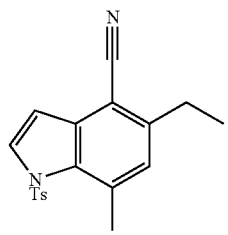 [SMILES: CCc1cc(C)c2c(ccn2S(=O)(=O)c2ccc(C)cc2)c1C#N]

To a solution of 5-bromo-7-methyl-1-tosyl-1H-indole-4-carbonitrile (Example 13-B) (7 g, 17.98 mmol) in THF (80 ml) was added a 1 M solution of $ZnEt_2$ in hexanes (25 ml, 25.00 mmol), followed by $Pd[(t-Bu)_3P]_2$ (500 mg, 0.978 mmol). The mixture was then stirred at room temperature for 3 h and then quenched with MeOH under $N_2$ atmosphere. The mixture was stirred for 1 h. The reaction was poured into a mixture EtOAc/Celite®/half satd. aq. $KHSO_4$. The resulting heterogeneous mixture was filtered through a pad of Celite®. The filtrate was then partitioned and the organic phase was washed successively with $H_2O$, and brine, dried over $Na_2SO_4$, filtered, and concentrated. The resulting residue was used in the next reaction without the need for further purification MS (ESI+) m/z 337.1 (M–H).

EXAMPLE 14B

5-Ethyl-7-methyl-1-tosyl-1H-indole-4-carbaldehyde

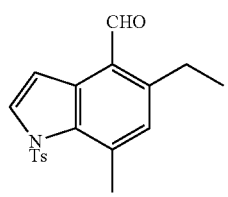 [SMILES: CCc1cc(C)c2c(ccn2S(=O)(=O)c2ccc(C)cc2)c1C=O]

To a solution of 5-ethyl-7-methyl-1-tosyl-1H-indole-4-carbonitrile (Example 14-A) (5.6 g, 16.55 mmol) in toluene (250 ml) at −78° C. was added a 1 M solution of DIBAL-H in toluene (21.51 ml, 21.51 mmol). The mixture was then stirred at −78° C. for ca. 1 h. The reaction was then quenched with MeOH at −78° C. To the mixture was added 5N aq. HCl (50 mL), and the reaction mixture was then placed at room temperature and stirred for ca. 1 h. Next Na+/K+ tartrate (Rochelle's salt) and $H_2O$ (200 mL) was added. The mixture was then vigorously stirred at room temperature. for ~12 h. The mixture was then diluted with EtOAc and filtered through a pad of Celite®. The filtrate was portioned and the organic layer was washed successively washed with 5% aq. $NaHCO_3$, $H_2O$, and brine, dried over $Na_2SO_4$, filtered, and concentrated to furnish the title compounds without the need for further purification. MS (ESI+) m/z 342.0 (M+H).

EXAMPLE 14-C

5-Ethyl-7-methyl-1H-indole-4-carbaldehyde

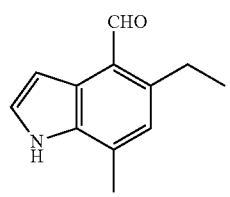

A mixture 5-ethyl-7-methyl-1-tosyl-1H-indole-4-carbaldehyde (Example 14-B) (5.63 g, 16.5 mmol) and KOH (4.63 g, 83 mmol) in EtOH (50 ml) was stirred at 100° C. for 5 h under the microwave irradiation. The reaction mixture was then diluted with $CH_2Cl_2$ and filtered through $SiO_2$ pad. The $SiO_2$ pad was washed with $CH_2Cl_2$/MeOH (c.a. 6/1). The filtrate was concentrated to give the title compound without the need for further purification. MS (ESI+) m/z 188.1 (M+H).

EXAMPLE 14-D tert-Butyl 5-ethyl-4-formyl-7-methyl-1H-indole-1-carboxylate

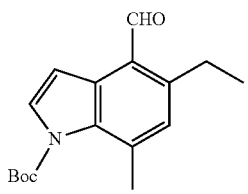 [SMILES: CCc1cc(C)c2c(ccn2C(=O)OC(C)(C)C)c1C=O]

To a solution of 5-ethyl-7-methyl-1H-indole-4-carbaldehyde (Example 14-C) (3.09 g, 16.5 mmol), $Boc_2O$ (3.83 ml, 16.50 mmol) and $Et_3N$ (2.300 ml, 16.50 mmol) in $CH_3CN$ (100 ml) was added DMAP (2.016 g, 16.50 mmol), and then the mixture was stirred at room temperature. After ca. 4 h the reaction was quenched with $H_2O$. The whole mixture was vigorously stirred at room temperature for ca. 18 h. The mixture was then diluted with $CH_2Cl_2$ and the organic phase was then washed successively with $H_2O$ and brine, dried over $Na_2SO_4$, filtered, and concentrated. The resulting residue was purified by silica gel flash column chromatography [heptane/30% EtOAc in $CH_2Cl_2$=82/18] to give the title compound. MS (ESI+) m/z 288.1 (M+H).

EXAMPLE 14-E (±)-tert-Butyl 4-((6-cyano-3-((2-(trimethylsilyl)ethoxy)methyl)-3H-imidazo[4,5-b]pyridin-2-yl)(hydroxy)methyl)-5-ethyl-7-methyl-1H-indole-1-carboxylate

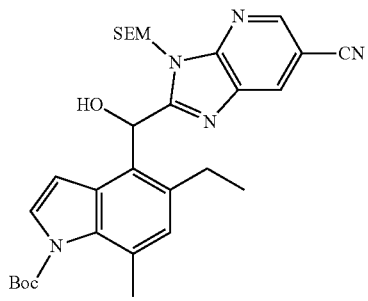 [SMILES: CCc1cc(C)c2c(ccn2C(=O)OC(C)(C)C)c1C(O)c1nc2cc(C#N)cnc2n1COCC[Si](C)(C)C]

To a solution of 3-((2-(trimethylsilyl)ethoxy)methyl)-3H-imidazo[4,5-b]pyridine-6-carbonitrile (Example 1) (1.2 g, 4.37 mmol) in THF (20 ml) at −78° C. under a nitrogen atmosphere, was added 2N LDA in THF (2.84 ml, 5.69 mmol). The reaction mixture was stirred at −78° C. for 15 min, then a solution of tert-butyl 5-ethyl-4-formyl-7-methyl-1H-indole-1-carboxylate (Example 14-D) (1.320 g, 4.59 mmol) in THF (10 mL) was added. The reaction mixture was stirred at −78° C. for 15 min, and then warmed to room temperature. The reaction mixture was quenched then with sat. aqueous solution of NH$_4$Cl. The mixture was extracted with ethyl acetate twice. The combined organic layers were dried over Na$_2$SO$_4$. After filtration and concentration, the resulting residue was purified by FCC (ethyl acetate/heptanes=0 to 100%) to give the title compound. MS (ESI+) m/z 562.47 (M+H).

EXAMPLE 14-F tert-Butyl 4-(6-cyano-3-((2-(trimethylsilyl)ethoxy)methyl)-3H-imidazo[4,5-b]pyridine-2-carbonyl)-5-ethyl-7-methyl-1H-indole-1-carboxylate

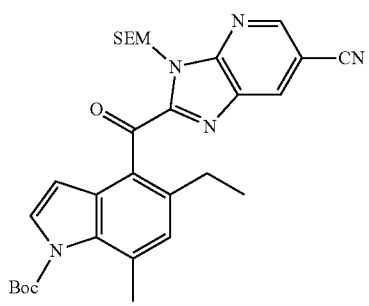 [SMILES: CCc1cc(C)c2c(ccn2C(=O)OC(C)(C)C)c1C(=O)c1nc2cc(C#N)cnc2n1COCC[Si](C)(C)C]

To a solution of (±)-tert-butyl 4-((6-cyano-3-((2-(trimethylsilyl)ethoxy)methyl)-3H-imidazo[4,5-b]pyridin-2-yl)(hydroxy)methyl)-5-ethyl-7-methyl-1H-indole-1-carboxylate (Example 14-E) (2 g, 3.56 mmol) in DCM (30 ml) was added MnO$_2$ (6.19 g, 71.2 mmol). The reaction was stirred at rt for 16 h. The reaction mixture was then filtered through a Celite® pad, washed with DCM. The collected organic layers were concentrated to give the title compound. MS (ESI+) m/z 560.33 (M+H).

EXAMPLE 14-G (±)-tert-Butyl 4-(1-(6-cyano-3-((2-(trimethylsilyl)ethoxy)methyl)-3H-imidazo[4,5-b]pyridin-2-yl)-2,2,2-trifluoro-1-hydroxyethyl)-5-ethyl-7-methyl-1H-indole-1-carboxylate

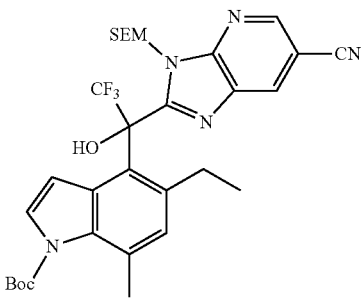 [SMILES: CCc1cc(C)c2c(ccn2C(=O)OC(C)(C)C)c1C(O)(c1nc2cc(C#N)cnc2n1COCC[Si](C)(C)C)C(F)(F)F]

To a suspension of tert-butyl 4-(6-cyano-3-((2-(trimethylsilyl)ethoxy)methyl)-3H-imidazo[4,5-b]pyridine-2-carbonyl)-5-ethyl-7-methyl-1H-indole-1-carboxylate (Example 14-F) (660 mg, 1.179 mmol) and CsF (17.91 mg, 0.118 mmol) in THF (10 ml) at 0° C. was added trimethyl(trifluoro-methyl)silane (0.553 ml, 3.54 mmol). After addition, the reaction was stirred at 0° C. for 15 min, then at rt for 2 h. Next, a 1N solution of TBAF in THF (4.72 mL, 4.72 mmol) was added and the reaction mixture which was then stirred at rt for 30 min, then brine was added to quench the reaction. The mixture was extracted with DCM three times. The combined organic layers were dried over Na$_2$SO$_4$. After filtration and concentration, the resulting residue was purified by FCC (ethyl acetate/heptanes=0 to 40%) to give the title compound. MS (ESI+) m/z 630.30 (M+H).

EXAMPLE 14-H (±)-tert-Butyl 4-(1-(6-cyano-3H-imidazo[4,5-b]pyridin-2-yl)-2,2,2-trifluoro-1-hydroxyethyl)-5-ethyl-7-methyl-1H-indole-1-carboxylate

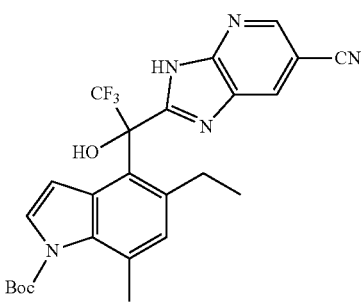 [SMILES: CCc1cc(C)c2c(ccn2C(=O)OC(C)(C)C)c1C(O)(c1nc2cc(C#N)cnc2[nH]1)C(F)(F)F]

To a 1.25 N solution of HCl in methanol (10 ml, 12.50 mmol) was added to (±)-tert-butyl 4-(1-(6-cyano-3-((2-(trimethylsilyl)ethoxy)methyl)-3H-imidazo[4,5-b]pyridin-2-yl)-2,2,2-trifluoro-1-hydroxyethyl)-5-ethyl-7-methyl-1H-indole-1-carboxylate (Example 14-G) (650 mg, 1.032 mmol). The reaction was stirred at 40° C. for 1.5 hr. The reaction mixture was cooled to 0° C. and diluted with water and neutralized by NaHCO$_3$ solid slowly. The reaction mixture was extracted with ethyl acetate twice. The combined organic layers were dried over Na$_2$SO$_4$. Filtration and concentration, afforded the title compound without the need for further purification. MS (ESI+) m/z 500.30 (M+H).

EXAMPLE 14-I a) (±)-2-(1-(5-Ethyl-7-methyl-1H-indol-4-yl)-2,2,2-trifluoro-1-hydroxyethyl)-3H-imidazo[4,5-b]pyridine-6-carbonitrile

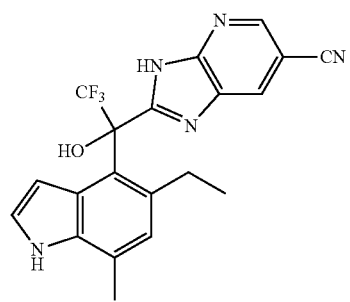 [SMILES: CCc1cc(C)c2[nH]ccc2c1C(O)(c1nc2cc(C#N)cnc2[nH]1)C(F)(F)F]

To a solution of tert-butyl (±)-4-(1-(6-cyano-3H-imidazo[4,5-b]pyridin-2-yl)-2,2,2-trifluoro-1-hydroxyethyl)-5-ethyl-7-methyl-1H-indole-1-carboxylate (220 mg, 0.440 mmol) (Example 14-H) in methanol (10 ml) was added potassium carbonate (609 mg, 4.40 mmol). The reaction was stirred at 45° C. for 30 min. The reaction mixture was cooled to rt and diluted with water and extracted with ethyl acetate. After separation of layers, the aqueous layer was extracted with ethyl acetate twice. The combined organic layers were dried over Na$_2$SO$_4$. After filtration and concentration, the resulting residue was purified by FCC (ethyl acetate/DCM=0 to 100%) to give title compound. $^1$H NMR (400 MHz, METHANOL-d$_4$) δ ppm 8.68 (br. s., 1 H), 8.36 (br. s., 1 H), 6.96 (d, J=3.3 Hz, 1 H), 6.88 (s, 1 H), 5.97 (d, J=2.0 Hz, 1 H), 2.94-3.11 (m, 1 H), 2.52-2.66 (m, 1 H), 2.47 (s, 3 H), 1.13 (t, J=7.3 Hz, 3 H). HRMS calcd. for C$_{20}$H$_{16}$F$_3$N$_5$O (M+H)$^+$ 400.1385. found 400.1378.

b) (+) and (−)-2-(1-(5-Ethyl-7-methyl-1H-indol-4-yl)-2,2,2-trifluoro-1-hydroxyethyl)-3H-imidazo[4,5-b]pyridine-6-carbonitrile Resolution of the enantiomers (±)-2-(1-(5-ethyl-7-methyl-1H-indol-4-yl)-2,2,2-trifluoro-1-hydroxyethyl)-3H-imidazo[4,5-b]pyridine-6-carbonitrile (Example 14-I) was achieved by chiral SFC using a OD-H column with 10% ethanol (plus 0.2% diethylamine) in CO$_2$ to give (+)-2-(1-(5-ethyl-7-methyl-1H-indol-4-yl)-2,2,2-trifluoro-1-hydroxyethyl)-3H-imidazo[4,5-b]pyridine-6-carbonitrile (t$_r$=10.46 min) give (−)-2-(1-(5-ethyl-7-methyl-1H-indol-4-yl)-2,2,2-trifluoro-1-hydroxyethyl)-3H-imidazo[4,5-b]pyridine-6-carbonitrile (t$_r$=15.44 min).

EXAMPLE 15

EXAMPLE 15-A (±)-tert-Butyl 4-(1-(6-cyano-3-((2-(trimethylsilyl)ethoxy)methyl)-3H-imidazo[4,5-b]pyridin-2-yl)-1-(2-(trimethylsilyl)ethylsulfonamido)ethyl)-5-ethyl-7-methyl-1H-indole-1-carboxylate

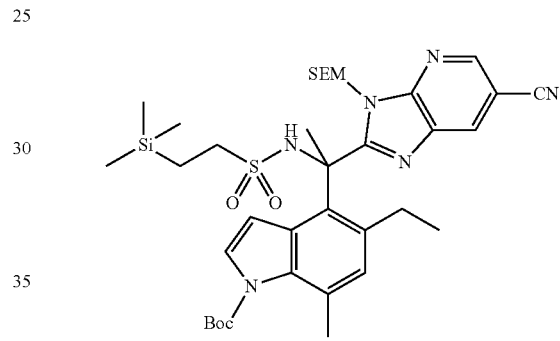

To the mixture of tert-butyl 4-(6-cyano-3-((2-(trimethylsilyl)ethoxy)methyl)-3H-imidazo[4,5-b]pyridine-2-carbonyl)-5-ethyl-7-methyl-1H-indole-1-carboxylate (Example 14-F) (810 mg, 1.45 mmol) and 2-(trimethylsilyl)-ethanesulfonamide (394 mg, 2.17 mmol) under nitrogen, was added 0.5 M stock solution of Zr(O-t-Bu)$_4$ in toluene (6.52 mL, 3.26 mmol). The reaction was stirred and heated at 100° C. for 3 hr. The reaction was then cooled to rt and additional 2-(trimethylsilyl)ethanesulfonamide (262 mg, 1.45 mmol) was added, followed by additional 0.5 M Zr(O-t-Bu)$_4$ in toluene stock solution (4.34 mL, 2.17 mmol). The reaction was stirred and heated at 100° C. for 2 hrs. Then the reaction mixture was cooled to −40° C. and a 3 M solution of MeMgI in THF (3.0 mL, 9.0 mmol) was added dropwise very slowly via syringe. After the addition was complete, the reaction was quenched via successive slow addition of methanol, and 1 N HCl. The reaction mixture was then diluted with DCM and water and brought to pH ~7 by addition of solid NaHCO$_3$ solid till pH>7. Celite® was then added and the mixture stirred for 30 minutes, at which time the heterogeneous mixture was filtered, through a Celite® pad, which was washed with DCM. The filtrate separation was portioned and the aqueous layer was extracted with DCM twice. The combined organic layers were dried over Na$_2$SO$_4$. After filtration and concentration, the resulting residue was purified by FCC ((30% ethyl acetate in DCM)/heptanes=0 to 100%) to give the title compound. MS (ESI+) m/z 739.49 (M+H).

EXAMPLE 15-B (±)-tert-Butyl 4-(1-(6-cyano-3-((2-(trimethylsilyl)ethoxy)methyl)-3H-imidazo[4,5-b]pyridin-2-yl)-1-(N-methyl-2-(trimethylsilyl)ethylsulfonamido)ethyl)-5-ethyl-7-methyl-1H-indole-1-carboxylate

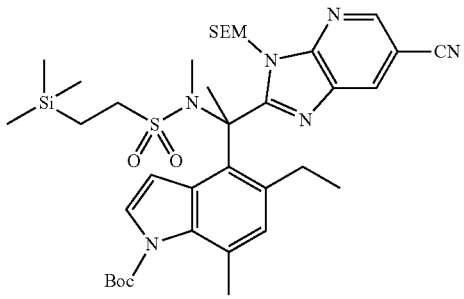 [SMILES: CCc1cc(C)c2c(ccn2C(=O)OC(C)(C)C)c1C(C)(c1nc2cc(C#N)cnc2n1COCC[Si](C)(C)C)N(C)S(=O)(=O)CC[Si](C)(C)C]

To a suspension of (±)-tert-butyl 4-(1-(6-cyano-3-((2-(trimethylsilyl)ethoxy)methyl)-3H-imidazo[4,5-b]pyridin-2-yl)-1-(2-(trimethylsilyl)ethylsulfonamido)ethyl)-5-ethyl-7-methyl-1H-indole-1-carboxylate (Example 15-A) (300 mg, 0.406 mmol) and potassium carbonate (561 mg, 4.06 mmol) in acetone (15 ml) was added iodomethane (254 µl, 4.06 mmol). The reaction was heated to 65° C. and stirred for 20 h. The reaction mixture was cooled to rt and diluted with water. The mixture was extracted with ethyl acetate three times. The combined organic layers were dried over Na₂SO₄. After filtration and concentration, the resulting residue was used to next step without purification. MS (ESI+) m/z 753.45 (M+H).

EXAMPLE 15-C (±)-tert-Butyl 4-(1-(6-cyano-3-((2-(trimethylsilyl)ethoxy)methyl)-3H-imidazo[4,5-b]pyridin-2-yl)-1-(methylamino)ethyl)-5-ethyl-7-methyl-1H-indole-1-carboxylate

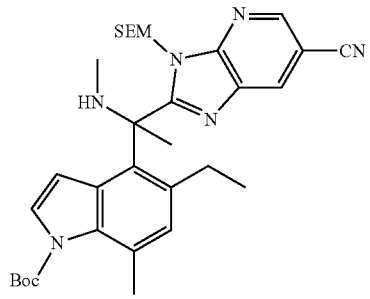 [SMILES: CCc1cc(C)c2c(ccn2C(=O)OC(C)(C)C)c1C(C)(NC)c1nc2cc(C#N)cnc2n1COCC[Si](C)(C)C]

To a solution of (±)-tert-butyl 4-(1-(6-cyano-3-((2-(trimethylsilyl)ethoxy)methyl)-3H-imidazo[4,5-b]pyridin-2-yl)-1-(N-methyl-2-(trimethylsilyl)ethylsulfonamido)ethyl)-5-ethyl-7-methyl-1H-indole-1-carboxylate (Example 15-B) (440 mg, 0.584 mmol) in DMF (4 ml), was added CsF (887 mg, 5.84 mmol). The reaction is heated to 100° C. for 3 h. The reaction mixture was then diluted with water (10 ml) and extracted with 20 ml of a mixed solution of ethyl acetate and heptanes (1/1). The organic layer was separated and aqueous layer was extracted with ethyl acetate-heptanes (1/1) solution twice. The combined organic layers were washed with brine and dried over Na₂SO₄. After filtration and concentration, the resulting residue was purified by FCC (ethyl acetate/DCM=0 to 50%) to give the title compound. MS (ESI+) m/z 589.3 (M+H).

EXAMPLE 15-D (±)-2-(1-(5-Ethyl-7-methyl-1H-indol-4-yl)-1-(methylamino)ethyl)-3H-imidazo[4,5-b]pyridine-6-carbonitrile

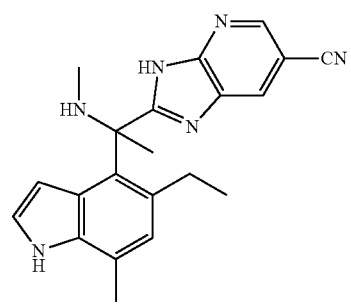 [SMILES: CCc1cc(C)c2[nH]ccc2c1C(C)(NC)c1nc2cc(C#N)cnc2[nH]1]

To a 1.25 N solution of HCl in methanol (6.25 mL, 7.81 mmol) was added to (±)-tert-butyl 4-(1-(6-cyano-3-((2-(trimethylsilyl)ethoxy)methyl)-3H-imidazo[4,5-b]pyridin-2-yl)-1-(methylamino)ethyl)-5-ethyl-7-methyl-1H-indole-1-carboxylate (Example 15-C) (230 mg, 0.391 mmol). The reaction was stirred at 40° C. for 0.5 h and then the reaction mixture was cooled to 0° C. and diluted with methanol (10 ml), and then slowly charged with solid potassium carbonate (2.7 g, 19.54 mmol) to basicify the mixture. Then, the reaction mixture was heated at 45° C. for 1 h. The reaction mixture was then cooled to rt and diluted with water and extracted with ethyl acetate twice. The combined organic layers were washed with brine and dried over Na₂SO₄. After filtration and concentration, the resulting residue was purified by FCC (ethyl acetate/DCM=0 to 100%). The product was further purified by acidic HPLC (acetonitrile/0.1% TFA in water=20% to 80%) to give the title compound as TFA salt. $^1$H NMR (400 MHz, METHANOL-d₄) δ ppm 8.63-8.90 (m, 1 H), 8.06-8.63 (m, 1 H), 7.28 (br. s., 1 H), 7.02 (s, 1 H), 6.30 (br. s., 1 H), 2.67-2.79 (m, 1 H), 2.55-2.64 (m, 4 H), 2.54 (s, 3 H), 2.52 (s, 3 H), 1.05 (t, J=7.4 Hz, 3 H). HRMS calcd. for C₂₀H₂₂N₆ (M-NHMe)⁺ 328.1562. found 328.2563. MS (ESI+) m/z 359.2 (M+H).

EXAMPLE 16

EXAMPLE 16-A

5-Bromo-7-methyl-1-tosyl-1H-indole-4-carbaldehyde

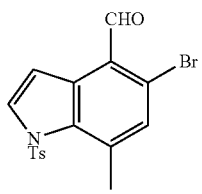 [SMILES: Cc1ccc(S(=O)(=O)n2ccc3c(C=O)c(Br)cc(C)c32)cc1]

To a solution of 5-bromo-7-methyl-1-tosyl-1H-indole-4-carbonitrile (Example 13-B) (10 g, 25.7 mmol) in toluene (500 ml) at −78° C. was added 1 M DIBAL-H (38.5 ml, 38.5 mmol) in toluene over 10 min. The mixture was then stirred at −78° C. for ca. 75 minutes.

The reaction was then quenched with MeOH at −78° C. To the mixture was then added 5 N aq. HCl (100 mL), and the reaction mixture was then placed at room temperature for 2 h at which time an excess of solid Na+/K+ tartrate (Rochelle's Salt) was added followed by $H_2O$ (100 mL The mixture was then vigorously stirred at room temperature for ca. 3 h and then diluted with EtOAc. The mixture was filtered through Celite® pad and the filtrate was partitioned. The organic phase was successively washed with 5% aq. $NaHCO_3$, $H_2O$, and brine, dried over $Na_2SO_4$, filtered, and concentrated to furnish the title compound without the need for further purification need for further purification. MS (ESI+) m/z 392.0, 394.0 (M+H).

EXAMPLE 16-B

5-Bromo-7-methyl-1H-indole-4-carbaldehyde

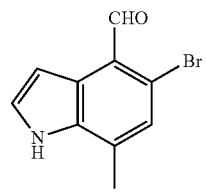

To a solution of 5-bromo-7-methyl-1-tosyl-1H-indole-4-carbaldehyde (Example 16-A) (6.5 g, 16.57 mmol) in 1,4-dioxane (50 ml)/$H_2O$ (5 ml) was added KOH (2 g, 35.6 mmol). The mixture was stirred at 100° C. for ca. 3 h. The reaction mixture was then diluted with $CH_2Cl_2$, and the mixture was washed with $H_2O$ and brine, and the organic layer dried over $Na_2SO_4$, filtered, and concentrated to afford the title compound without the need for further purification. MS (ESI+) m/z 237.9, 239.9 (M+H).

EXAMPLE 16-C tert-Butyl 5-bromo-4-formyl-7-methyl-1H-indole-1-carboxylate

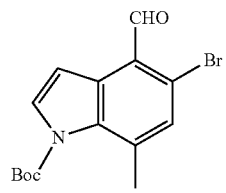

To a solution of 5-bromo-7-methyl-1H-indole-4-carbaldehyde (Example 16-B) (3.6 g, 15.12 mmol) in $CH_3CN$ was added $Boc_2O$ (7.02 ml, 30.2 mmol), followed by DMAP (0.185 g, 1.512 mmol). The mixture was stirred at room temperature for ca. 1 h. Then the reaction was quenched with $H_2O$. The whole mixture was vigorously stirred for 0.5 h. The mixture was then diluted with $CH_2Cl_2$. The organic phase was then washed successively with $H_2O$ and brine, dried over $Na_2SO_4$, filtered, and concentrated. The resulting residue was purified by silica gel flash column chromatography [heptane/30% EtOAc in CH2Cl2=85/15] to give the title compound. MS (ESI+) m/z 338.0, 340.0 (M+H).

EXAMPLE 16-D tert-Butyl 5-cyclopropyl-4-formyl-7-methyl-1H-indole-1-carboxylate

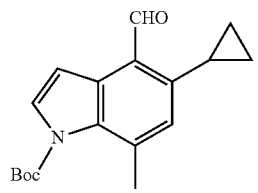 [SMILES: Cc1cc(C2CC2)c(C=O)c2ccn(C(=O)OC(C)(C)C)c12]

To a suspension of tert-butyl 5-bromo-4-formyl-7-methyl-1H-indole-1-carboxylate (Example 16-C) (9.5 g, 14.05 mmol) in toluene (50 ml)/$H_2O$ (20 ml) at room temperature was added $Cs_2CO_3$ (27.5 g, 84 mmol), potassium cyclopropyltetrafluoroborate (4.16 g, 28.1 mmol), and Ru-Phos (CAS#; 787618-22-8) (2.62 g, 5.62 mmol), followed by and $Pd(OAc)_2$ (0.631 g, 2.81 mmol). The whole mixture was then stirred at 100° C. for 2 h. The reaction mixture was cooled down to room temperature and diluted with $CH_2Cl_2$. The organic layer was washed successively with $H_2O$ and brine, dried over $Na_2SO_4$, filtered and concentrated. The resulting residue was purified by silica gel flash column chromatography [heptane/(30% EtOAc in $CH_2Cl_2$)=82/18] the resulting solid was triturated with heptane, and then the heptane layer was decanted out to furnish the title compound. MS (ESI+) m/z 300.1 (M+H).

EXAMPLE 16-E (±)-tert-Butyl 4-((6-cyano-3-((2-(trimethylsilyl)ethoxy)methyl)-3H-imidazo[4,5-b]pyridin-2-yl)(hydroxy)methyl)-5-cyclopropyl-7-methyl-1H-indole-1-carboxylate

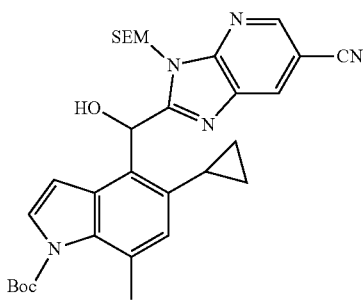 [SMILES: Cc1cc(C2CC2)c(C(O)c2nc3cc(C#N)cnc3n2COCC[Si](C)(C)C)c2ccn(C(=O)OC(C)(C)C)c12]

To a solution of 3-((2-(trimethylsilyl)ethoxy)methyl)-3H-imidazo[4,5-b]pyridine-6-carbonitrile (1.567 g, 5.71 mmol) (Example 1) in THF (20 ml) at −78° C. under nitrogen atmosphere, was added a 1.8 M solution of LDA in THF (4.34 ml, 7.82 mmol). The reaction mixture is stirred at −78° C. for 15 min, then a solution of tert-butyl 5-cyclopropyl-4-formyl-7-methyl-1H-indole-1-carboxylate (Example 16-D) (1.8 g, 6.01 mmol) in THF (10 mL) was added. The reaction mixture was stirred at −78° C. for 15 min, then warmed to rt. The reaction mixture was quenched with sat. aqueous NH₄Cl solution. The mixture was extracted with ethyl acetate twice. The combined organic layers were dried over Na₂SO₄. After filtration and concentration, the resulting residue was purified by FCC (ethyl acetate/heptanes=0 to 80%) to give the title compound. MS (ESI+) m/z 574.4 (M+H).

EXAMPLE 16-F (±)-tert-Butyl 4-((6-cyano-3H-imidazo[4,5-b]pyridin-2-yl)(hydroxy)methyl-5-cyclopropyl-7-methyl-1H-indole-1-carboxylate

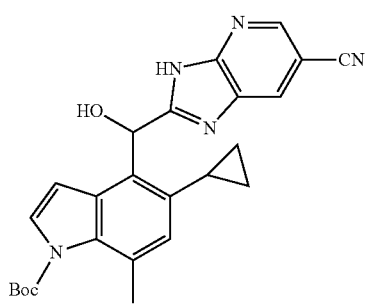 [SMILES: Cc1cc(C2CC2)c(C(O)c2nc3cc(C#N)cnc3[nH]2)c2ccn(C(=O)OC(C)(C)C)c12]

A 1N solution of HCl in methanol (10 mL, 10 mmol) was added to (±)-tert-butyl 4-((6-cyano-3-((2-(trimethylsilypethoxy)methyl)-3H-imidazo[4,5-b]pyridin-2-yl)(hydroxy)methyl)-5-cyclopropyl-7-methyl-1H-indole-1-carboxylate (Example 16-E) (345 mg, 0.601 mmol). The reaction was stirred at 40° C. for 3 h. The reaction mixture was then cooled to 0° C. and diluted with DCM. The reaction mixture was washed with water and brine and dried over Na₂SO₄. After filtration and concentration, the resulting residue was purified by FCC (DCM/2M ammonia in MeOH=96/4, isocratic) to give the title compound. MS (ESI+) m/z 444.1 (M+H).

EXAMPLE 16-G (±)-2-((5-Cyclopropyl-7-methyl-1H-indol-4-yl)(hydroxy)methyl)-3H-imidazo[4,5-b]pyridine-6-carbonitrile

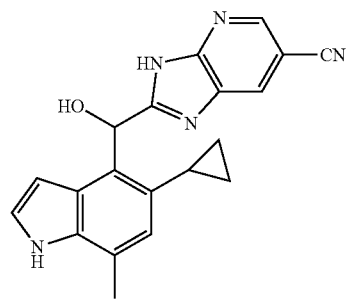 [SMILES: Cc1cc(C2CC2)c(C(O)c2nc3cc(C#N)cnc3[nH]2)c2cc[nH]c12]

A suspension of (±)-tert-butyl 4-((6-cyano-3H-imidazo[4,5-b]pyridin-2-yl)(hydroxy)methyl)-5-cyclopropyl-7-methyl-1H-indole-1-carboxylate (Example 16-F) (220 mg, 0.496 mmol) and Cs₂CO₃ (323 mg, 0.992 mmol) in MeOH (5 mL) was stirred at 60° C. for 4 h. The reaction mixture was then cooled to rt and absorbed onto silica gel and purified by FCC (CH₂Cl₂/2M NH₃ in MeOH=96/4, isocratic) to give the title compound. ¹H NMR (400 MHz, CD3CN with 5 μL TFA) δ ppm 9.32 (br. s., 1 H), 8.78 (d, J=1.90 Hz, 1 H), 8.39 (d, J=1.89 Hz, 1 H), 7.16 (dd, J=2.80, 2.90 Hz, 1 H), 7.05 (s, 1 H), 6.82 (s, 1 H), 6.20-6.23 (m, 1 H), 2.46 (d, J=0.76 Hz, 3 H), 2.11-2.18 (m, 1 H), 0.74-0.94 (m, 3 H), 0.51-0.57 (m, 1 H). HRMS calcd. for C₂₀H₁₇N₅O (M+H)⁺344.1506. found 344.1468.

EXAMPLE 17

EXAMPLE 17-A tert-Butyl 4-(6-cyano-3-((2-(trimethylsilyl)ethoxy)methyl)-3H-imidazo[4,5-b]pyridine-2-carbonyl)-5-cyclopropyl-7-methyl-1H-indole-1-carboxylate

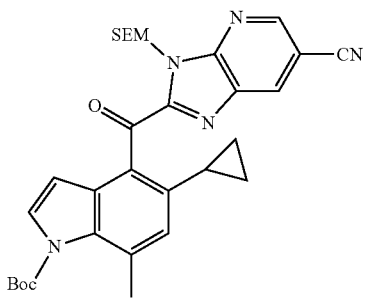 [SMILES: Cc1cc(C2CC2)c(C(=O)c2nc3cc(C#N)cnc3n2COCC[Si](C)(C)C)c2ccn(C(=O)OC(C)(C)C)c12]

To a solution of (±)-tert-butyl 4-((6-cyano-3-((2-(trimethylsilyl)ethoxy)methyl)-3H-imidazo[4,5-b]pyridin-2-yl)(hydroxy)methyl)-5-cyclopropyl-7-methyl-1H-indole-1-carboxylate (3.02 g, 5.26 mmol) (Example 16-E) in DCM (100 ml) was added MnO₂ (9.15 g, 105 mmol). The reaction was stirred at rt for 16 h. The reaction mixture was filtered through a Celite® pad. DCM was used to wash the pad. The collected filtrate was concentrated to give the title compound. MS (ESI+) m/z 572.5 (M+H).

EXAMPLE 17-B (±)-tert-Butyl 4-(1-(6-cyano-3-((2-(trimethylsilyl)ethoxy)methyl)-3H-imidazo[4,5-b]pyridin-2-yl)-1-hydroxyethyl)-5-cyclopropyl-7-methyl-1H-indole-1-carboxylate

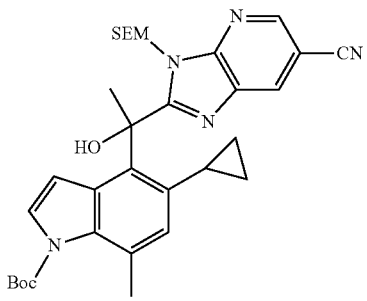 [SMILES: Cc1cc(C2CC2)c(C(C)(O)c2nc3cc(C#N)cnc3n2COCC[Si](C)(C)C)c2ccn(C(=O)OC(C)(C)C)c12]

To a solution of tert-butyl 4-(6-cyano-3-((2-(trimethylsilyl)ethoxy)methyl)-3H-imidazo[4,5-b]pyridine-2-carbonyl)-5-cyclopropyl-7-methyl-1H-indole-1-carboxylate (Example 17-A) (600 mg, 1.049 mmol) in THF (10 ml) at −20° C., was added a 3 M solution of CH₃MgI in THF (1.049 ml, 3.15 mmol). The reaction was stirred at −20° C. for 10 min, and then stirred at rt for 10 min. The reaction was quenched with sat. aqueous NH₄Cl and extracted with ethyl acetate twice. The combined organic layers were dried over Na2SO4. Filtration and concentration afforded the title compound without the need for further purification. MS (ESI+) m/z 588.2 (M+H).

EXAMPLE 17-C (±)-2-(1-(5-Cyclopropyl-7-methyl-1H-indol-4-yl)-1-hydroxyethyl)-3H-imidazo[4,5-b]pyridine-6-carbonitrile To the mixture of 1N TBAF in THF (20.08 mL, 20.08 mmol) and (±)-tert-butyl 4-(1-(6-cyano-3-((2-(trimethylsilypethoxy)methyl)-3H-imidazo[4,5-b]pyridin-2-yl)-1-hydroxyethyl)-5-cyclopropyl-7-methyl-1H-indole-1-carboxylate (Example 17-B) (590 mg, 1.004 mmol) was added 1 ml of ethylenediamine. The reaction mixture was heated to 45° C. for 30 min and then the reaction mixture was concentrated. The resulting residue was taken up in MeOH (15 mL) and charged with K₂CO₃ (2775 mg, 20.08 mmol). The reaction mixture was heated to 60° C. for 1.5 h. The reaction mixture was then cooled to rt and diluted with water and extracted with ethyl acetate twice. The combined organic layers were dried over Na₂SO₄. After filtration and concentration, the resulting residue was purified by FCC (ethyl acetate/DCM=0 to 100% at 70%) to give the title compound. ¹H NMR (400 MHz, METHANOL-d₄) δ ppm 8.51-8.78 (m, 1 H), 8.02-8.41 (m, 1 H), 7.15 (d, J=3.3 Hz, 1 H), 6.74 (d, J=14.1 Hz, 1 H), 6.54 (s, 1 H), 2.43 (s, 3 H), 2.31 (br. s., 3 H), 1.71-1.91 (m, 1 H), 0.46-0.72 (m, 2 H), 0.40 (dd, J=8.0, 5.7 Hz, 1 H), 0.14-0.27 (m, 1 H). HRMS calcd. for C₂₁H₁₉N₅O (M+H)⁺358.1668, found 358.1663.

EXAMPLE 17-D (±)-tert-Butyl 4-(1-(6-cyano-3-((2-(trimethylsilyl) ethoxy)methyl)-3H-imidazo[4,5-b]pyridin-2-yl)-2,2, 2-trifluoro-1-hydroxyethyl)-5-cyclopropyl-7-methyl-1H-indole-1-carboxylate

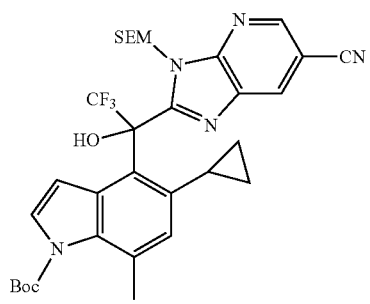 [SMILES: Cc1cc(C2CC2)c(C(O)(c2nc3cc(C#N)cnc3n2COCC[Si](C)(C)C)C(F)(F)F)c2ccn(C(=O)OC(C)(C)C)c12]

To a suspension of tert-butyl 4-(6-cyano-3-((2-(trimethylsilyl)ethoxy)methyl)-3H-imidazo[4,5-b]pyridine-2-carbonyl)-5-cyclopropyl-7-methyl-1H-indole-1-carboxylate (1.1 g, 1.924 mmol) (Example 17-A) and CsF (0.058 g, 0.385 mmol) in THF (15 ml) at 0° C., was added trimethyl (trifluoromethyl)silane (0.752 ml, 4.81 mmol). After addition, the reaction was stirred at 0° C. for 15 min, then at rt for 2 h. Then a 1N solution of TBAF in THF (9.62 ml, 9.62 mmol) was added and the reaction mixture was stirred at rt for an additional 30 min. the mixture was then quenched with brine and extracted with DCM three times. The combined organic layers were dried over Na₂SO₄. After filtration and concentration, the resulting residue was purified by FCC (ethyl acetate/heptanes=0 to 40%) to give the title compound. MS (ESI+) m/z 642.2 (M+H).

EXAMPLE 17-E (±)-tert-Butyl 4-(1-(6-cyano-3H-imidazo[4,5-b]pyridin-2-yl)-2,2,2-trifluoro-1-hydroxyethyl)-5-cyclopropyl-7-methyl-1H-indole-1-carboxylate

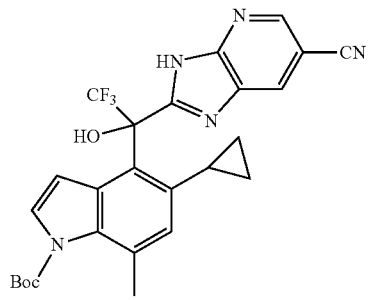 [SMILES: Cc1cc(C2CC2)c(C(O)(c2nc3cc(C#N)cnc3[nH]2)C(F)(F)F)c2ccn(C(=O)OC(C)(C)C)c12]

The mixture of 1.25 N HCl solution in MeOH (22.4 mL, 28.0 mmol) and (±)-tert-butyl 4-(1-(6-cyano-3-((2-(trimethylsilyl)pethoxy)methyl)-3H-imidazo[4,5-b]pyridin-2-yl)-2, 2,2-trifluoro-1-hydroxyethyl)-5-cyclopropyl-7-methyl-1H-indole-1-carboxylate (Example 17-D) (900 mg, 1.402 mmol) was stirred at 40° C. for 1 h. The reaction mixture was cooled to 0° C. and diluted with water and neutralized by NaHCO₃ solid slowly. The reaction mixture was extracted with ethyl acetate twice. The combined organic layers were dried over Na₂SO₄. After filtration and concentration, the resulting residue was used to next step without purification. MS (ESI+) m/z 512.3 (M+H).

EXAMPLE 17-F (±)-tert-Butyl 4-(1-amino-1-(6-cyano-3H-imidazo[4, 5-b]pyridin-2-yl)-2,2,2-trifluoroethyl)-5-cyclopropyl-7-methyl-1H-indole-1-carboxylate

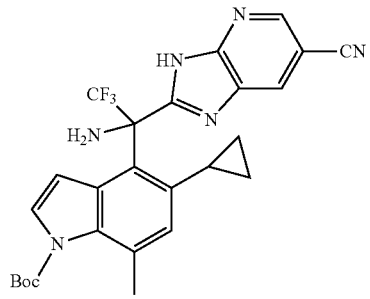 [SMILES: Cc1cc(C2CC2)c(C(N)(c2nc3cc(C#N)cnc3[nH]2)C(F)(F)F)c2ccn(C(=O)OC(C)(C)C)c12]

To a solution of (±)-tert-butyl 4-(1-(6-cyano-3H-imidazo [4,5-b]pyridin-2-yl)-2,2,2-trifluoro-1-hydroxyethyl)-5-cyclopropyl-7-methyl-1H-indole-1-carboxylate (Example 17-E) (250 mg, 0.489 mmol) in CHCl$_3$ (5 ml) was added one drop of DMF (~10 µL). Then thionyl chloride (357 µL, 4.89 mmol) was added. The reaction was heated to 75° C. for 30 min, and then cooled to 0° C. A 7 N solution ammonia in methanol (3 mL) was then added carefully and slowly to the reaction mixture. After addition, the reaction was stirred at rt for 15 min and then diluted with ethyl acetate and brine. The resulting layers were separated and the aqueous layer was extracted with ethyl acetate three times. The combined organic layers were dried over Na$_2$SO$_4$. After filtration and concentration, the resulting residue was purified by FCC (ethyl acetate/heptanes=0 to 100%) to give the title compound. MS (ESI+) m/z 511.2 (M+H).

EXAMPLE 17-G (±)-2-(1-Amino-1-(5-cyclopropyl-7-methyl-1H-indol-4-yl)-2,2,2-trifluoroethyl)-3H-imidazo[4,5-b]pyridine-6-carbonitrile

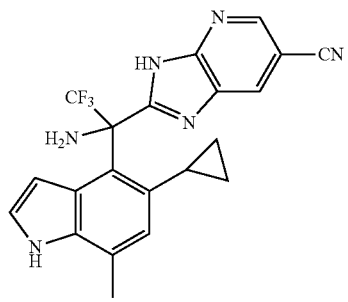 [SMILES: Cc1cc(C2CC2)c(C(N)(c2nc3cc(C#N)cnc3[nH]2)C(F)(F)F)c2cc[nH]c12]

To a solution of (±)-tert-butyl 4-(1-amino-1-(6-cyano-3H-imidazo[4,5-b]pyridin-2-yl)-2,2,2-trifluoroethyl)-5-cyclopropyl-7-methyl-1H-indole-1-carboxylate (Example 17-F) (26 mg, 0.051 mmol) in methanol (2 ml) was added K$_2$CO$_3$ (70.4 mg, 0.509 mmol). The reaction was heated to 45° C. for 1 h. The reaction mixture was then diluted with brine and ethyl acetate. After separation of the resulting layers, the aqueous layer was extracted with ethyl acetate three times. The combined organic layers were dried over Na$_2$SO$_4$. After filtration and concentration, the resulting residue was purified by FCC (ethyl acetate/heptane=0 to 100%) and further purified by acidic HPLC (ACN/water with 0.1% TFA=20% to 60%) to give the title compound as TFA salt. $^1$H NMR (400 MHz, METHANOL-d$_4$) δ ppm 8.66 (d, J=1.9 Hz, 1 H), 8.32 (d, J=1.6 Hz, 1 H), 7.10 (d, J=3.3 Hz, 1 H), 6.58 (s, 1 H), 6.50 (br. s., 1 H), 2.46 (s, 2 H), 2.46 (s, 3 H), 2.13-2.28 (m, 1 H), 0.78-0.86 (m, 1 H), 0.66-0.76 (m, 1 H), 0.46-0.55 (m, 1 H), 0.11-0.24 (m, 1 H). HRMS calcd. for C$_{21}$H$_{17}$F$_3$N$_6$ (M+H)$^+$411.1545, found 411.1546.

Compounds of invention are active on factor B inhibition. Data on Table 1 collected using the assay of Biological Example 2.7.

TABLE 1

| Example number | IC$_{50}$ (nM) |
|---|---|
| 5-B b) (+) | 290 |
| 5-B b) (−) | 140 |
| 6-C b) (−) | 90 |
| 6-C b) (+) | 700 |
| 7-D b) (+) | 50 |
| 7-D b) (−) | 130 |

TABLE 1-continued

| Example number | IC$_{50}$ (nM) |
|---|---|
| 8-B b) (+) | 720 |
| 8-B b) (−) | 30 |
| 9-D b) (+) | 1525 |
| 9-D b) (−) | 30 |
| 10-B b) (−) | 40 |
| 10-B b) (+) | 1380 |
| 11-B b) (−) | 295 |
| 11-B b) (+) | 3135 |
| 12-D | 40 |
| 14-I b) (+) | 2350 |
| 14-I b) (−) | 100 |
| 15-D | 540 |
| 16-G | 460 |
| 17-C | 60 |
| 17-G | 90 |

What is claimed is:

1. A compound, or salt or a tautomer thereof, according to Formula (I):

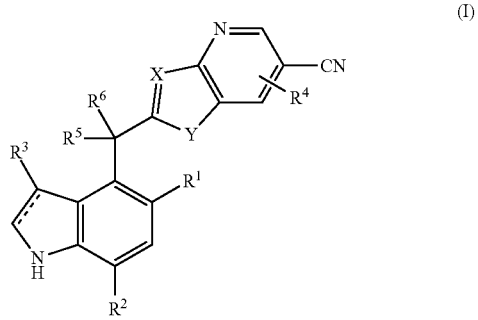

Wherein

 is a single or double bond;

X is N or CH;

Y is N(H), O or S;

R$^1$ is halogen, C$_1$-C$_6$alkyl, C$_2$-C$_6$alkenyl, C$_3$-C$_6$cycloalkyl, C$_1$-C$_6$alkoxy, haloC$_1$-C$_6$alkyl, hydroxyC$_1$-C$_6$alkyl, aminoC$_1$-C$_6$alkyl, C$_1$-C$_6$alkoxyC$_1$-C$_6$alkyl, C$_1$-C$_6$alkoxyC$_1$-C$_6$alkoxy, C$_3$-C$_6$cycloalkylC$_1$-C$_5$alkoxy, haloC$_1$-C$_6$alkoxy, S(O)$_p$C$_1$-C$_6$alkyl, CH$_2$NHC(O)C$_1$-C$_4$alkyl or OCH$_2$C(O)R$^7$, p is 0, 1, or 2;

R$^2$ is C$_1$-C$_6$alkyl, C$_1$-C$_6$alkoxy, hydroxyC$_1$-C$_6$alkyl or halogen;

R$^3$ is hydrogen, halogen, cyano, C$_1$-C$_4$alkyl, haloC$_1$-C$_4$alkyl, CH$_2$C(O)R$^7$, phenyl or 5 or 6 member heteroaryl having 1, 2 or 3 ring heteroatoms independently selected from N, O or S, wherein the phenyl or heteroaryl is optionally substituted with 0, 1, or 2 C$_1$-C$_4$alkyl groups, and wherein alkyl and haloalkyl optionally substituted with 0 or 1 hydroxy;

R$^4$ is 0, 1, or 2 substitutents independently selected at each occurrence from halogen and C$_1$-C$_6$alkyl;

R$^5$ is hydrogen, C$_1$-C$_6$alkyl, haloC$_1$-C$_6$alkyl, C$_3$-C$_6$cycloalkyl, phenyl or 5 or 6 member heteroaryl having 1, 2 or 3 ring heteroatoms independently selected from N, O or S;

or R$^3$ and R$^5$ taken in combination form a divalent —CH$_2$—CH$_2$— or —CH$_2$—N(H)— group;

R$^6$ is hydrogen, hydroxy, amino, C$_1$-C$_6$alkyl, C$_1$-C$_6$alkoxy, C$_1$-C$_6$alkoxyC$_1$-C$_6$alkoxy, mono- and di-$C_1$-$C_4$alkylamino, amino $C_1$-$C_6$alkylamino, $[CR^A{}_2]_nR^{10}$, $O[CR^A{}_2]_nR^7$, NHC(O)$C_1$-$C_6$alkyl, NHS$(O_2)C_1$-$C_6$alkyl, $CH_2R^9$, $OCH_2R^9$, $O[CR^A{}_2]_nR^7$, N(H)$[CR^A{}_2]_nR^7$, C(O)$R^7$ or N(H) $[CR^A{}_2]_nC(O)R^7$;

or $CR^5R^6$, taken in combination, form a divalent carbonyl group, a divalent =$CH_2$ group or cyclopropyl which cyclopropyl is optionally substituted by $CO_2H$ or $CH_2OH$;

or when $R^5$ is hydrogen, then $R^6$ may also be selected from $[CR^A{}_2]_nR^7$ or $[CR^A{}_2]_nC(O)R^7$;

n is 1, 2, or 3;

$R^A$ is independently selected at each occurrence from hydrogen, halogen or $C_1$-$C_4$alkyl;

$R^7$ is hydroxy, $C_1$-$C_4$alkoxy, amino, or mono- and di-$C_1$-$C_4$alkylamino;

$R^8$ is hydrogen or halogen;

$R^9$ is a 5 member heteroaryl having 1 to 4 ring heteroatoms selected from N, O or S and optionally substituted with 0, 1, or 2 $C_1$-$C_4$alkyl groups; and $R^{10}$ is amino or mono- and di-$C_1$-$C_4$alkylamino.

2. The compound of claim 1, or salt or tautomer thereof, according to Formula (Ia):

(Ia)

3. The compound of claim 1, or salt or tautomer thereof, wherein $R^4$ is absent.

4. The compound of claim 1, or salt or tautomer thereof, wherein $R^3$ is hydrogen, chloro or phenyl.

5. The compound of claim 1, or salt or tautomer thereof, wherein $R^3$ is hydrogen.

6. The compound of claim 1, or a salt or tautomer thereof, wherein $R^2$ is methyl.

7. The compound of claim 1, or a salt or tautomer thereof, wherein $R^1$ is halogen, $C_1$-$C_4$alkyl, vinyl, cyclopropyl, $C_1$-$C_4$alkoxy, hydroxy$C_1$-$C_4$alkyl, $C_1$-$C_4$alkoxy$C_1$-$C_4$alkyl, $C_1$-$C_4$alkoxy$C_1$-$C_4$alkoxy, cyclopropyl$C_1$-$C_4$alkoxy, halo$C_1$-$C_4$alkoxy or S(O)$_2C_1$-$C_4$alkyl.

8. The compound of claim 1, or salt or tautomer thereof, wherein $R^1$ is $C_1$-$C_4$alkyl, $C_1$-$C_4$alkoxy, cyclopropyl, bromo or difluoromethoxy.

9. The compound of claim 1, or a salt or tautomer thereof, wherein $R^5$ is hydrogen, methyl, ethyl cyclopropyl or trifluoromethyl.

10. The compound of claim 1, or a salt or tautomer thereof, wherein $R^6$ is hydrogen, hydroxy, methoxy, amino, mono- and di-methylamino or $CH_2R^{10}$;

or when $R^5$ is hydrogen, then $R^6$ may also be selected from $CH_2R^7$ or $CH_2C(O)R^7$, $[CH_2]_2R^7$ or $[CH_2]_2C(O)R^7$;

$R^7$ is hydroxy, amino, N(H)$CH_3$ or N($CH_3$)$_2$; and $R^{10}$ is amino, N(H)$CH_3$ or N($CH_3$)$_2$.

11. The compound of claim 1, or a salt or tautomer thereof, wherein $R^5$ is methyl or trifluoromethyl;

$R^6$ is hydroxy, methoxy, amino, methylamino or $CH_2R^7$; and $R^7$ is amino, N(H)$CH_3$ or N($CH_3$)$_2$.

12. The compound of claim 2, salt or tautomer thereof, wherein $R^1$ is $C_1$-$C_4$alkyl, $C_1$-$C_4$alkoxy, or cyclopropyl;

$R^2$ is methyl;

$R^3$ and $R^4$ are hydrogen;

$R^5$ is hydroxyl, amino, mono- and di-$C_1$-$C_2$alkylamino, $C_1$-$C_2$alkyl, or $C_1$-$C_2$alkoxy; and $R^6$ is hydrogen, $C_1$-$C_2$alkyl, or trifluoromethyl.

13. The compound of claim 1, or a salt or tautomer thereof, which compound is selected from the group consisting of (+)-2-(1-amino-2,2,2-trifluoro-1-(5-methoxy-7-methyl-1H-indol-4-yl)ethyl)-3H-imidazo[4,5-b]pyridine-6-carbonitrile;

(−)-2-(1-amino-2,2,2-trifluoro-1-(5-methoxy-7-methyl-1H-indol-4-yl)ethyl)-3H-imidazo[4,5-b]pyridine-6-carbonitrile;

(+)-2-(hydroxy(5-methoxy-7-methyl-1H-indol-4-yl)methyl)-1H-imidazo[4,5-b]pyridine-6-carbonitrile;

(−)-2-(hydroxy(5-methoxy-7-methyl-1H-indol-4-yl)methyl)-1H-imidazo[4,5-b]pyridine-6-carbonitrile;

(+)-2-(1-hydroxy-1-(5-methoxy-7-methyl-1H-indol-4-yl)ethyl)-3H-imidazo[4,5-b]pyridine-6-carbonitrile;

(−)-2-(1-hydroxy-1-(5-methoxy-7-methyl-1H-indol-4-yl)ethyl)-3H-imidazo[4,5-b]pyridine-6-carbonitrile;

(+)-2-(1-methoxy-1-(5-methoxy-7-methyl-1H-indol-4-yl)ethyl)-3H-imidazo[4,5-b]pyridine-6-carbonitrile;

(−)-2-(1-methoxy-1-(5-methoxy-7-methyl-1H-indol-4-yl)ethyl)-3H-imidazo[4,5-b]pyridine-6-carbonitrile;

(+)-2-(2,2,2-trifluoro-1-(5-methoxy-7-methyl-1H-indol-4-yl)-1-(methylamino)ethyl)-3H-imidazo[4,5-b]pyridine-6-carbonitrile;

(−)-2-(2,2,2-trifluoro-1-(5-methoxy-7-methyl-1H-indol-4-yl)-1-(methylamino)ethyl)-3H-imidazo[4,5-b]pyridine-6-carbonitrile;

(+)-2-(1-amino-1-(5-methoxy-7-methyl-1H-indol-4-yl)ethyl)-3H-imidazo[4,5-b]pyridine-6-carbonitrile;

(−)-2-(1-amino-1-(5-methoxy-7-methyl-1H-indol-4-yl)ethyl)-3H-imidazo[4,5-b]pyridine-6-carbonitrile;

(+)-2-(1-(5-methoxy-7-methyl-1H-indol-4-yl)-1-(methylamino)ethyl)-3H-imidazo[4,5-b]pyridine-6-carbonitrile;

(−)-2-(1-(5-methoxy-7-methyl-1H-indol-4-yl)-1-(methylamino)ethyl)-3H-imidazo[4,5-b]pyridine-6-carbonitrile;

2-(2-(5-methoxy-7-methyl-1H-indol-4-yl)propan-2-yl)-3H-imidazo[4,5-b]pyridine-6-carbonitrile;

(+)-2-(1-(5-ethyl-7-methyl-1H-indol-4-yl)-2,2,2-trifluoro-1-hydroxyethyl)-3H-imidazo[4,5-b]pyridine-6-carbonitrile;

(−)-2-(1-(5-ethyl-7-methyl-1H-indol-4-yl)-2,2,2-trifluoro-1-hydroxyethyl)-3H-imidazo[4,5-b]pyridine-6-carbonitrile;

(±)-2-(1-(5-ethyl-7-methyl-1H-indol-4-yl)-1-(methylamino)ethyl)-3H-imidazo[4,5-b]pyridine-6-carbonitrile;

(±)-2-((5-cyclopropyl-7-methyl-1H-indol-4-yl)(hydroxy)methyl)-3H-imidazo[4,5-b]pyridine-6-carbonitrile;

(±)-2-(1-(5-cyclopropyl-7-methyl-1H-indol-4-yl)-1-hydroxyethyl)-3H-imidazo[4,5-b]pyridine-6-carbonitrile;

(±)-2-(1-amino-1-(5-cyclopropyl-7-methyl-1H-indol-4-yl)-2,2,2-trifluoroethyl)-3H-imidazo[4,5-b]pyridine-6-carbonitrile; and salts and tautomers thereof.

14. A pharmaceutical composition comprising one or more pharmaceutically acceptable carriers and a therapeutically effective amount of a compound of claim 1.

* * * * *